(12) United States Patent
Zhang et al.

(10) Patent No.: US 10,618,943 B2
(45) Date of Patent: Apr. 14, 2020

(54) UBIQUITIN VARIANT MODULATORS OF HECT E3 LIGASES AND THEIR USES

(71) Applicant: The Governing Council of the University of Toronto, Toronto (CA)

(72) Inventors: Wei Zhang, Mississauga (CA); Sachdev Sidhu, Toronto (CA)

(73) Assignees: Sachdev Sidhu, Toronto (CA); Wei Zhang, Toronto (CA)

( * ) Notice: Subject to any disclaimer, the term of this patent is extended or adjusted under 35 U.S.C. 154(b) by 46 days.

(21) Appl. No.: 15/436,399

(22) Filed: Feb. 17, 2017

(65) Prior Publication Data

US 2017/0275341 A1 Sep. 28, 2017

Related U.S. Application Data

(60) Provisional application No. 62/296,265, filed on Feb. 17, 2016.

(51) Int. Cl.
| | | |
|---|---|---|
| *C07K 14/47* | (2006.01) | |
| *C07H 21/04* | (2006.01) | |
| *C12N 9/10* | (2006.01) | |
| *C12N 9/00* | (2006.01) | |
| *G01N 30/02* | (2006.01) | |
| *G01N 30/00* | (2006.01) | |

(52) U.S. Cl.
CPC ............ *C07K 14/47* (2013.01); *C07H 21/04* (2013.01); *C12N 9/10* (2013.01); *C12N 9/104* (2013.01); *C12N 9/93* (2013.01); *C12Y 603/02019* (2013.01); *G01N 30/02* (2013.01); *G01N 30/00* (2013.01); *G01N 2030/022* (2013.01); *G01N 2030/027* (2013.01)

(58) Field of Classification Search
CPC ......... C07H 21/04; C07K 14/00; C07K 14/47
See application file for complete search history.

(56) References Cited

U.S. PATENT DOCUMENTS

2013/0225436 A1* 8/2013 Sidhu ..................... C07K 14/47
506/9

OTHER PUBLICATIONS

Adams et al., "Phenix: a comprehensive Python-based system for macromolecular structure solution," Acta Crystallogr D Biol Crystallogr 66(Pt 2):213-21 (2010).
Alfano et al., "RhoB regulates uPAR signalling," J Cell Sci. 125(Pt 10):2369-80 (2012).
Bencsath et al., "Identification of a multifunctional binding site on Ubc9p required for Smt3p conjugation," J Biol Chem. 277(49):47938-45 (2002).
Cao et al., "Selective small molecule compounds increase BMP-2 responsiveness by inhibiting Smurf1-mediated Smad1/5 degradation," Sci Rep. 4:4965 (11 pages) (2014).
Castillo-Lluva et al.,"The tumour suppressor HACE1 controls cell migration by regulating Rac1 degradation," Oncogene. 32(13):1735-42 (2013).
Chen et al., "MolProbity: all-atom structure validation for macromolecular crystallography," Acta Crystallogr D Biol Crystallog. 66(Pt 1):12-21 (2010).

(Continued)

*Primary Examiner* — Jeremy C Flinders
(74) *Attorney, Agent, or Firm* — Clark & Elbing LLP; Susan M. Michaud

(57) ABSTRACT

The invention provides ubiquitin variants that specifically bind to HECT E3 ligases, and methods of using these variants to modulate the activity of HECT E3 ligases.

7 Claims, 12 Drawing Sheets

Specification includes a Sequence Listing.

(56) References Cited

OTHER PUBLICATIONS

Cohen et al., "Will the ubiquitin system furnish as many drug targets as protein kinases?" Cell. 143(5):686-93 (2010).

David et al., "Smurf2 E3 ubiquitin ligase modulates proliferation and invasiveness of breast cancer cells in a CNKSR2 dependent manner," Cell Div. 9:2 (2014) (18 pages).

Deng et al., "E3 ubiquitin ligases in regulating stress fiber, lamellipodium, and focal adhesion dynamics," Cell Adh Migr. 8(1):49-54 (2014).

Doye et al., "Assessing ubiquitylation of Rho GTPases in mammalian cells," Methods Mol Biol. 827:77-86 (2012).

Duc et al., "Cell-specific expression of epithelial sodium channel alpha, beta, and gamma subunits in aldosterone-responsive epithelia from the rat: localization by in situ hybridization and immunocytochemistry," J Cell Biol. 127(6 Pt 2):1907-21 (1994).

Emsley et al., "Features and development of Coot," Acta Crystallogr D Biol Crystallogr. 66(Pt 4):486-501 (2010).

Ernst et al., "A strategy for modulation of enzymes in the ubiquitin system," Science. 339(6119):590-5 (2013).

Escobedo et al., "Structural basis of the activation and degradation mechanisms of the E3 ubiquitin ligase Nedd4L," Structure. 22(10):1446-57 (2014).

French et al., "Regulation of the RSP5 ubiquitin ligase by an intrinsic ubiquitin-binding site," J Biol Chem. 284(18):12071-9 (2009).

Gallagher et al., "Activation of the E3 ubiquitin ligase Itch through a phosphorylation-induced conformational change," Proc Natl Acad Sci USA. 103(6):1717-22 (2006).

Herrador et al., "A mechanism for protein monoubiquitination dependent on a trans-acting ubiquitin-binding domain," J Biol Chem. 288(23):16206-11 (2013).

Huang et al., "Structure of an E6AP-UbcH7 complex: insights into ubiquitination by the E2-E3 enzyme cascade," Science. 286(5443):1321-6 (1999).

Hubbard, "NACCESS," Computer Program, Department of Biochemistry and Molecular Biology, University College London. <http://wolf.bms.umist.ac.uk/naccess/> 1993 (1 page).

Huibregtse et al., "A family of proteins structurally and functionally related to the E6-AP ubiquitin-protein ligase," Proc Natl Acad Sci USA. 92(7):2563-7 (1995).

Inoue et al., "Mule/Huwe1/Arf-BP1 suppresses Ras-driven tumorigenesis by preventing c-Myc/Miz1-mediated downregulation of p21 and p15," Genes Dev. 27(10):1101-14 (2013).

Jin et al., "Smad ubiquitination regulatory factor 2 promotes metastasis of breast cancer cells by enhancing migration and invasiveness," Cancer Res. 69(3):735-40 (2009).

Kamadurai et al., "Insights into ubiquitin transfer cascades from a structure of a UbcH5B~ubiquitin-HECT(NEDD4L) complex," Mol Cell. 36(6):1095-102 (2009).

Kamadurai et al., "Mechanism of ubiquitin ligation and lysine prioritization by a HECT E3," Elife. 2:e00828 (26 pages) (2013).

Kamynina et al., "Distinct characteristics of two human Nedd4 proteins with respect to epithelial Na(+) channel regulation," Am J Physiol Renal Physiol. 281(3):F469-77 (2001).

Kathman et al., "A small molecule that switches a ubiquitin ligase from a processive to a distributive enzymatic mechanism," J Am Chem Soc. 137(39):12442-5 (2015).

Kay et al., "High-throughput biotinylation of proteins," Methods Mol Biol. 498:185-98 (2009).

Kim et al., "Polyubiquitination by HECT E3s and the determinants of chain type specificity," Mol Cell Biol. 29(12):3307-18 (2009).

Kim et al., "Structure and function of a HECT domain ubiquitin-binding site," EMBO Rep. 12(4):334-41 (2011).

Kimura et al., "Deletion of the ubiquitin ligase Nedd4L in lung epithelia causes cystic fibrosis-like disease," Proc Natl Acad Sci USA. 108(8):3216-21 (2011).

Kirkpatrick et al., "The absolute quantification strategy: a general procedure for the quantification of proteins and post-translational modifications," Methods. 35(3):265-73 (2005).

Krissinel et al., "Inference of macromolecular assemblies from crystalline state," J Mol Biol. 372(3):774-97 (2007).

Lifton et al., "Molecular mechanisms of human hypertension," Cell. 104(4):545-56 (2001).

Lin et al., "Crystal structures of two bacterial HECT-like E3 ligases in complex with a human E2 reveal atomic details of pathogen-host interactions," Proc Natl Acad Sci USA. 109(6):1925-30 (2012).

Lu et al., "The PY motif of ENaC, mutated in Liddle syndrome, regulates channel internalization, sorting and mobilization from subapical pool," Traffic. 8(9):1246-64 (2007).

MacLean et al., "Skyline: an open source document editor for creating and analyzing targeted proteomics experiments," Bioinformatics. 26(7):966-8 (2010).

Maddika et al., "WWP2 is an E3 ubiquitin ligase for PTEN," Nat Cell Biol. 13(6):728-33 (2011) (13 pages).

Mak et al., "A lentiviral functional proteomics approach identifies chromatin remodeling complexes important for the induction of pluripotency," Mol Cell Proteomics. 9(5):811-23 (2010).

Mari et al., "Structural and functional framework for the autoinhibition of Nedd4-family ubiquitin ligases," Structure. 22(11):1639-49 (2014).

Maspero et al., "Structure of the HECT:ubiquitin complex and its role in ubiquitin chain elongation," EMBO Rep. 12(4):342-9 (2011).

Maspero et al., "Structure of a ubiquitin-loaded HECT ligase reveals the molecular basis for catalytic priming," Nat Struct Mol Biol. 20(6):696-701 (2013) (8 pages).

McCoy et al., "Phaser crystallographic software," J Appl Crystallog. 40(Pt 4):658-74 (2007).

Mund et al., "Peptide and small molecule inhibitors of HECT-type ubiquitin ligases," Proc Natl Acad Sci USA. 111(47):16736-41 (2014).

Murshudov et al., "Refinement of macromolecular structures by the maximum-likelihood method," Acta Crystallogr D Biol Crystallogr. 53(Pt 3):240-55 (1997).

Nalepa et al., "Drug discovery in the ubiquitin-proteasome system," Nat Rev Drug Discov. 5(7):596-613 (2006).

Ogunjimi et al., "The ubiquitin binding region of the Smurf HECT domain facilitates polyubiquitylation and binding of ubiquitylated substrates," J Biol Chem. 285(9):6308-15 (2010).

Ordureau et al., "Defining roles of PARKIN and ubiquitin phosphorylation by PINK1 in mitochondrial quality control using a ubiquitin replacement strategy," Proc Natl Acad Sci USA. 112(21):6637-42 (2015).

Ordureau et al., "Quantifying ubiquitin signaling," Mol Cell. 58(4):660-76 (2015).

Ordureau et al., "Quantitative proteomics reveal a feedforward mechanism for mitochondrial PARKIN translocation and ubiquitin chain synthesis," Mol Cell. 56(3):360-75 (2014).

Otwinowski et al., "Processing of X-ray diffraction data collected in oscillation mode," Methods Enzymol. 276:307-26 (1997).

Persaud et al., "Tyrosine phosphorylation of NEDD4 activates its ubiquitin ligase activity," Sci Signal. 7(346):ra95 (2014) (11 pages).

Petroski, "The ubiquitin system, disease, and drug discovery," BMC Biochem. 9(Suppl 1):S7 (15 pages) (2009).

Phillips et al. "Conformational dynamics control ubiquitin-deubiquitinase interactions and influence in vivo signaling," Proc Natl Acad Sci USA. 110(28):11379-84 (2013).

Phu et al., "Improved quantitative mass spectrometry methods for characterizing complex ubiquitin signals," Mol Cell Proteomics. 10(5):M110.003756 (19 pages) (2011).

Riling et al., "Itch WW domains inhibit its E3 ubiquitin ligase activity by blocking E2-E3 ligase trans-thiolation," J Biol Chem. 290(39):23875-87 (2015).

Rohde et al., "Type III secretion effectors of the IpaH family are E3 ubiquitin ligases," Cell Host Microbe. 1(1):77-83 (2007).

Ronchi et al., "E6AP/UBE3A ubiquitin ligase harbors two E2~ubiquitin binding sites," J Biol Chem. 288(15):10349-60 (2013).

Ronzaud et al., "Renal tubular NEDD4-2 deficiency causes NCC-mediated salt-dependent hypertension," J Clin Invest. 123(2):657-65 (2013).

Rossi et al., "High throughput screening for inhibitors of the HECT ubiquitin E3 ligase ITCH identifies antidepressant drugs as regulators of autophagy," Cell Death Dis. 5:e1203 (12 pages) (2014).

(56) References Cited

OTHER PUBLICATIONS

Rotin et al., "Physiological functions of the HECT family of ubiquitin ligases," Nat Rev Mol Cell Biol. 10(6):398-409 (2009).

Sato et al., "Growing self-organizing mini-guts from a single intestinal stem cell: mechanism and applications," Science. 340(6137):1190-4 (2013).

Scheffner et al., "Mammalian HECT ubiquitin-protein ligases: biological and pathophysiological aspects," Biochim Biophys Acta. 1843(1):61-74 (2014).

Sheng et al., "A human ubiquitin conjugating enzyme (E2)-HECT E3 ligase structure-function screen," Mol Cell Proteomics. 11(8):329-41 (2012).

Simpson et al., "Identification of genes that regulate epithelial cell migration using an siRNA screening approach," Nat Cell Biol. 10(9):1027-38 (2008) (27 pages).

Tonikian et al., "Identifying specificity profiles for peptide recognition modules from phage-displayed peptide libraries," Nat Protoc. 2(6):1368-86 (2007).

Torrino et al., "The E3 ubiquitin-ligase HACE1 catalyzes the ubiquitylation of active Rac1," Dev Cell. 21(5):959-65 (2011).

Verdecia et al., "Conformational flexibility underlies ubiquitin ligation mediated by the WWP1 HECT domain E3 ligase," Mol Cell. 11(1):249-59 (2003).

Wang et al., "ATR/Chk1/Smurf1 pathway determines cell fate after DNA damage by controlling RhoB abundance," Nat Commun. 5:4901 (13 pages) (2014).

Wang et al., "Regulation of cell polarity and protrusion formation by targeting RhoA for degradation," Science. 302(5651):1775-9 (2003).

Wiesner et al., "Autoinhibition of the HECT-type ubiquitin ligase Smurf2 through its C2 domain," Cell. 130(4):651-62 (2007).

Wilson et al., "Human hypertension caused by mutations in WNK kinases," Science. 293(5532):1107-12 (2001).

Winn et al., "Overview of the CCP4 suite and current developments," Acta Crystallogr D Biol Crystallogr. 67(Pt 4):235-42 (2011).

Zhang et al., "Conformational stabilization of ubiquitin yields potent and selective inhibitors of USP7," Nat Chem Biol. 9(1):51-8 (2013) (12 pages).

* cited by examiner

A

B

C

D

E

F

G

H

I

J

UBIQUITIN VARIANT MODULATORS OF HECT E3 LIGASES AND THEIR USES

FIELD OF THE INVENTION

This invention relates to ubiquitin variants that specifically bind to HECT E3 ligases, and use of these variants to modulate the activity of HECT E3 ligases.

BACKGROUND OF THE INVENTION

Ubiquitination mediated by E1-E2-E3 multi-enzyme cascades rivals phosphorylation as a predominant mechanism regulating myriad protein functions (Cohen and Tcherpakov, 2010; Nalepa et al., 2006). Repeated catalytic cycles result in substrates modified on multiple lysines with various polyubiquitin chains, which alter protein functions in an extraordinary variety of ways. Because E3 ligases control substrate specificity and the topology of ubiquitination, they represent attractive targets for therapeutic intervention (Nalepa et al., 2006; Petroski, 2008). Yet, identifying the diversity of mechanisms regulating E3 ligases, as well as generation of tools for their manipulation, has lagged behind deciphering regulation and developing therapeutics for kinases (Cohen and Tcherpakov, 2010; Nalepa et al., 2006). The first family of E3 ligases discovered (Huibregtse et al., 1995), HECT (Homologous to E6AP C-Terminus) E3s, have been directly implicated in cancer, hypertension, neurological disorders, and other diseases (see Table 2, below) (Rotin and Kumar, 2009; Scheffner and Kumar, 2014). Moreover, some pathogenic bacteria have evolved HECT-like E3s as virulence factors to manipulate host cell signaling (Lin et al., 2012; Rohde et al., 2007). Therefore, understanding molecular mechanisms of HECT E3 function could greatly advance therapeutic strategies for many diseases.

Development of agents to selectively modulate HECT E3s has been hampered by extreme inter-domain rotations accompanying catalysis, a shallow active site, and dynamic regulation of HECT E3 activity (Escobedo et al., 2014; Gallagher et al., 2006; Huang et al., 1999; Kamadurai et al., 2013; Kamadurai et al., 2009; Mari et al., 2014; Persaud et al., 2014; Ronchi et al., 2013; Verdecia et al., 2003; Wiesner et al., 2007). In principle, recently reported small molecule and peptide inhibitors obtained by high throughput screening for several HECT E3s provide routes to assess functions and mechanisms of HECT E3s in normal and diseased cells (Cao et al., 2014; Kathman et al., 2015; Mund et al., 2014; Rossi et al., 2014). However, existing molecules generally do not conform to a general strategy that could be used to interrogate HECT E3s across the family, fall short in terms of potency and specificity, and generally have had limited utility in probing unknown HECT mechanisms.

The defining feature of HECT E3s is a ~40 kDa C-terminal "HECT domain" containing two flexibly-tethered lobes (N- and C-), with 16-92% amino acid identity across the family. In addition to the catalytic domain, HECT E3 primary sequences reveal various N-terminal domains that may enable substrate binding and dynamic regulation by mediating autoinhibition and influencing subcellular localization (FIG. 1A). The largest and best-characterized class of HECT E3s comprises the NEDD4-family, which display a common architecture consisting of an N-terminal C2 domain, 2-4 central WW-domains distal and proximal to the catalytic domain, and the C-terminal HECT domain (Rotin and Kumar, 2009; Scheffner and Kumar, 2014) (FIG. 1A).

Studies of E3s in the NEDD4-family revealed that the HECT domain interacts with Ub at multiple sites. For example, in complex with E2~Ub or in the E3~Ub intermediate, the HECT "C-lobe" binds the Ub to be transferred, and a separate C-lobe interaction with the acceptor Ub is implied from biochemical studies (Kamadurai et al., 2013; Kamadurai et al., 2009; Kim and Huibregtse, 2009; Maspero et al., 2013). In addition to interactions made by the active-site-bound Ub, a weak Ub-binding "exosite" has been reported in the HECT "N-lobe" of various NEDD4-family E3s (French et al., 2009; Kim et al., 2011; Maspero et al., 2011; Ogunjimi et al., 2010).

SUMMARY OF THE INVENTION

In a first aspect, the invention provides ubiquitin variant (Ubv) polypeptides that include one or more substitution in one or more region of a ubiquitin polypeptide, wherein the region is selected from the group consisting of:

(a) region 1 (amino acids 2-14 of SEQ ID NO:1) wherein the polypeptide comprises the structure:

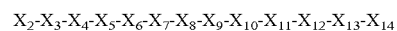

wherein $X_2$ is selected from the group consisting of A, D, E, H, K, L, P, Q, R, S, T, and Y;

$X_4$ is selected from the group consisting of A, C, F, I, L, R, S, V, and Y;

$X_6$ is selected from the group consisting of E, G, H, I, K, N, Q, R, S, V, W, and Y;

$X_8$ is selected from the group consisting of F, G, H, I, L, M, P, R, V, and Y;

$X_9$ is selected from the group consisting of A, F, G, I, K, L, M, N, P, R, S, and T;

$X_{10}$ is selected from the group consisting of A, D, G, L, R, V, and W;

$X_{11}$ is selected from the group consisting of D, E, H, I, K, L, M, N, P, Q, R, T, V, W, and Y;

$X_{12}$ is selected from the group consisting of D, G, I, L, N, P, S, T, V, and Y;

$X_{14}$ is selected from the group consisting of A, C, F, I, K, N, P, R, S, and T; and any X not specified optionally has the amino acid sequence of the corresponding position in SEQ ID NO:1;

(b) region 2 (amino acids 42-49 of SEQ ID NO:1) wherein the polypeptide comprises the structure:

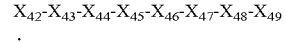

wherein $X_{42}$ is selected from the group consisting of F, G, I, K, L, Q, R, S, T, and V;

$X_{44}$ is selected from the group consisting of F, I, L, T, and V;

$X_{46}$ is selected from the group consisting of A, G, H, L, R, S, T, and V;

$X_{47}$ is selected from the group consisting of A, D, G, R, S, and W;

$X_{48}$ is selected from the group consisting of K, M, N, Q, R, and T;

$X_{49}$ is selected from the group consisting of D, E, H, I, K, N, P, Q, R, and S; and any X not specified optionally has the amino acid sequence of the corresponding position in SEQ ID NO:1; and (c) region 3 (amino acids 62-78 of SEQ ID NO:1) wherein the polypeptide comprises the structure:

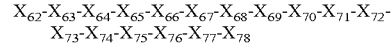

wherein
$X_{62}$ is selected from the group consisting of C, H, K, L, P, Q, R, and Y;
$X_{63}$ is selected from the group consisting of D, E, G, H, K, M, N, Q, R, and Y;
$X_{64}$ is selected from the group consisting of A, D, E, F, G, K, Q, R, T, V, W, and Y;
$X_{66}$ is selected from the group consisting of A, F, H, I, L, N, P, Q, R, S, T, and W;
$X_{68}$ is selected from the group consisting of G, F, H, L, N, R, S, T, W, and Y;
$X_{70}$ is selected from the group consisting of A, I, F, K, L, M, R, V, and W;
$X_{71}$ is selected from the group consisting of F, G, K, L, M, R, V, and Y;
$X_{72}$ is selected from the group consisting of G, I, K, P, Q, R, S, and T;
$X_{73}$ is selected from the group consisting of F, I, L, P, R, and T;
$X_{74}$ is selected from the group consisting of L, H, I, P, R, and V;
$X_{75}$ is selected from the group consisting of A, D, G, I, P, R, V, W, and Y;
$X_{76}$ is selected from the group consisting of A, D, F, G, H, K, L, M, N, P, Q, R, S, T, V, W, and Y;
$X_{77}$ is selected from the group consisting of A, D, E, F, H, I, K, M, N, P, Q, R, S, T, V, and Y, or is absent;
$X_{78}$ is selected from the group consisting of A, D, E, F, H, I, K, L, N, P, Q, R, S, T, V, W, and Y, or is absent; and any X not specified optionally has the amino acid sequence of the corresponding position in SEQ ID NO:1;
wherein any X specified in said Ubv polypeptide optionally has the amino acid sequence of the corresponding position in SEQ ID NO:1; or
a fragment thereof, wherein the sequence of said Ubv polypeptide does not consist of SEQ ID NO:1.

As noted above, any X not specified can optionally have the amino acid sequence of the corresponding position in SEQ ID NO:1 or, alternatively, the sequence of the corresponding position in any of the specific Ubv's listed herein, if different from that of SEQ ID NO:1.

In a first embodiment, the Ubv polypeptide binds to NEDD4 (N4). In this embodiment, the sequence of the Ubv polypeptide can include, for example, a sequence that is at least 90% identical to a sequence selected from the group consisting of SEQ ID NOs:2-4 or a fragment thereof. In specific examples, the sequence of the Ubv polypeptide includes a sequence selected from the group consisting of SEQ ID NOs:2-4.

In a second embodiment, the Ubv polypeptide binds to NEDD4L (NL). In this embodiment, the sequence of the Ubv polypeptide can include, for example, a sequence that is at least 90% identical to a sequence selected from the group consisting of SEQ ID NOs:5-8. In specific examples, the sequence of the Ubv polypeptide includes a sequence selected from the group consisting of SEQ ID NOs:5-8.

In a third embodiment, the Ubv polypeptide binds to ITCH (IT). In this embodiment, the sequence of the Ubv polypeptide can include, for example, a sequence that is at least 90% identical to a sequence selected from the group consisting of SEQ ID NOs:9-12. In specific examples, the sequence of the Ubv polypeptide includes a sequence selected from the group consisting of SEQ ID NOs:9-12.

In a fourth embodiment, the Ubv polypeptide binds to SMURF1 (51). In this embodiment, the sequence of the Ubv polypeptide can include, for example, a sequence that is at least 90% identical to a sequence selected from the group consisting of SEQ ID NOs:13-17. In specific examples, the sequence of the Ubv polypeptide includes a sequence selected from the group consisting of SEQ ID NOs:13-17.

In a fifth embodiment, the Ubv polypeptide binds to SMURF2 (S2). In this embodiment, the sequence of the Ubv polypeptide can include, for example, a sequence that is at least 90% identical to a sequence selected from the group consisting of SEQ ID NOs:18-22. In specific examples, the sequence of the Ubv polypeptide includes a sequence selected from the group consisting of SEQ ID NOs:18-22.

In a sixth embodiment, the Ubv polypeptide binds to WWP1 (P1). In this embodiment, the sequence of the Ubv polypeptide can include, for example, a sequence that is at least 90% identical to a sequence selected from the group consisting of SEQ ID NOs:23-26. In specific examples, the sequence of the Ubv polypeptide includes a sequence selected from the group consisting of SEQ ID NOs:23-26.

In a seventh embodiment, the Ubv polypeptide binds to WWP2 (P2). In this embodiment, the sequence of the Ubv polypeptide can include, for example, a sequence that is at least 90% identical to a sequence selected from the group consisting of SEQ ID NOs:27-30. In specific examples, the sequence of the Ubv polypeptide includes a sequence selected from the group consisting of SEQ ID NOs:27-30.

In an eighth embodiment, the Ubv polypeptide binds to HECW1 (W1). In this embodiment, the sequence of the Ubv polypeptide can include, for example, a sequence that is at least 90% identical to a sequence selected from the group consisting of SEQ ID NOs:31-34. In specific examples, the sequence of the Ubv polypeptide includes a sequence selected from the group consisting of SEQ ID NOs:31-34.

In a ninth embodiment, the Ubv polypeptide binds to HECW2 (W2). In this embodiment, the Ubv polypeptide can include, for example, a sequence that is at least 90% identical to a sequence selected from the group consisting of SEQ ID NOs:35-38. In specific examples, the sequence of the Ubv polypeptide includes a sequence selected from the group consisting of SEQ ID NOs:35-38.

In a tenth embodiment, the Ubv polypeptide binds to RSP5 (R5). In this embodiment, the sequence of the Ubv polypeptide can include, for example, a sequence that is at least 90% identical to a sequence selected from the group consisting of SEQ ID NOs:39-44. In specific examples, the Ubv polypeptide includes a sequence selected from the group consisting of SEQ ID NOs:39-44.

In an eleventh embodiment, the Ubv polypeptide binds to HERC1 (H1). In this embodiment, the sequence of the Ubv polypeptide can include, for example, a sequence that is at least 90% identical to a sequence selected from the group consisting of SEQ ID NOs:45 and 46. In specific examples, the sequence of the Ubv polypeptide includes a sequence selected from the group consisting of SEQ ID NOs:45 and 46.

In a twelfth embodiment, the Ubv polypeptide binds to HERC2 (H2). In this embodiment, the Ubv polypeptide can include, for example, a sequence that is at least 90% identical to a sequence selected from the group consisting of SEQ ID NOs:47 and 48. In specific examples, the sequence of the Ubv polypeptide includes a sequence selected from the group consisting of SEQ ID NOs:47 and 48.

In a thirteenth embodiment, the Ubv polypeptide binds to HERC4 (H4). In this embodiment, the Ubv polypeptide can include, for example, a sequence that is at least 90% identical to a sequence selected from the group consisting of SEQ ID NOs:49-52. In specific examples, the sequence of the Ubv polypeptide includes a sequence selected from the group consisting of SEQ ID NOs:49-52.

In a fourteenth embodiment, the Ubv polypeptide binds to HERC6 (H6). In this embodiment, the sequence of the Ubv polypeptide can include, for example, a sequence that is at least 90% identical to SEQ ID NO:53. In a specific example, the sequence of the Ubv polypeptide includes SEQ ID NO:53.

In a fifteenth embodiment, the Ubv polypeptide binds to HACE1 (HA). In this embodiment, the sequence of the Ubv polypeptide can include, for example, a sequence that is at least 90% identical to a sequence selected from the group consisting of SEQ ID NOs:54-56. In specific examples, the sequence of the Ubv polypeptide includes a sequence selected from the group consisting of SEQ ID NOs:54-56.

In a sixteenth embodiment, the Ubv polypeptide binds to HUWE1 (HU). In this embodiment, the sequence of the Ubv polypeptide can include, for example, a sequence that is at least 90% identical to a sequence selected from the group consisting of SEQ ID NOs:57 and 58. In specific examples, the Ubv polypeptide includes a sequence selected from the group consisting of SEQ ID NOs:57 and 58.

In a seventeenth embodiment, the Ubv polypeptide binds to UBE3C (3C). In this embodiment, the sequence of the Ubv polypeptide can include, for example, a sequence that is at least 90% identical to a sequence selected from the group consisting of SEQ ID NOs:59 and 60. In specific examples, the sequence of the Ubv polypeptide includes a sequence selected from the group consisting of SEQ ID NOs:59 and 60.

In an eighteenth embodiment, the Ubv polypeptide binds to HECTD1 (D1). In this embodiment, the sequence of the Ubv polypeptide can include, for example, a sequence that is at least 90% identical to a sequence selected from the group consisting of SEQ ID NOs:61-64. In specific examples, the sequence of the Ubv polypeptide includes a sequence selected from the group consisting of SEQ ID NOs:61-64.

In a nineteenth embodiment, the Ubv polypeptide binds to EDD1 (ED). In this embodiment, the sequence of the Ubv polypeptide can include, for example, a sequence that is at least 90% identical to a sequence selected from the group consisting of SEQ ID NOs:65 and 66. In specific examples, the sequence of the Ubv polypeptide includes a sequence selected from the group consisting of SEQ ID NOs:65 and 66.

In a twentieth embodiment, the Ubv polypeptide binds to KIAA0317 (KI). In this embodiment, the sequence of the Ubv polypeptide can include, for example, a sequence that is at least 90% identical to a sequence selected from the group consisting of SEQ ID NOs:67-70. In specific examples, the sequence of the Ubv polypeptide is selected from the group consisting of SEQ ID NOs:67-70.

In further embodiments, the Ubv polypeptide includes a fragment of a polypeptide having a sequence identifier noted above or a sequence at least 90% identical thereto.

In another aspect, the invention includes nucleic acid molecules that encode Ubv polypeptides or fragments thereof as described herein. In related aspects, the invention includes recombinant expression vectors that include such nucleic acid molecules, as well as host cells that include such nucleic acid molecules and/or vectors.

In a further aspect, the invention provides methods of obtaining a Ubv polypeptide that modulates an activity or property of a HECT E3 ligase. These methods can include, for example, steps of: (a) randomizing ubiquitin residues to produce a combinatorial library of Ubv polypeptides, and (b) selecting Ubv polypeptides that specifically bind to one or more HECT E3 ligase. In various embodiments, the randomized residues (a) contact the N-lobe exosite of a HECT E3 ligase, (b) contact the E2 site of a HECT E3 ligase, and/or (c) are within region 1 (amino acids 2-14), region 2 (amino acids 42-49), and/or region 3 (amino acids 62-78) of ubiquitin. Furthermore, in various examples, the HECT E3 ligase is selected from the group consisting of NEDD4 (N4), NEDD4L (NL), ITCH (IT), SMURF1 (S1), SMURF2 (S2), WWP1 (P1), WWP2 (P2), HECW1 (W1), HECW2 (W2), RSP5 (R5), HERC1 (H1), HERC2 (H2), HERC3 (H3), HERC4 (H4), HERC5 (H5), HERC6 (H6), HACE1 (HA), HUWE1 (HU), UBE3A (3A), UBE3B (3B), UBE3C (3C), HECTD1 (D1), EDD1 (ED), KIAA0317 (KI), HECTD1, HECTD2, HECTD3, HECTD4, G2E3, and TRIP12. The methods can optionally include one or more steps in which a selected Ubv is assessed for its effects on an activity of a HECT E3 ligase or on a cellular function or activity modulated by a HECT E3 ligase.

In an additional aspect, the invention includes methods of modulating (e.g., increasing or decreasing) an activity or property of a HECT E3 ligase. These methods can optionally include, for example, contacting the HECT E3 ligase with an agent that binds to the N-lobe exosite of the HECT E3 ligase or to the E2 site of the HECT E3 ligase. In various embodiments, the agent includes a Ubv polypeptide, a nucleic acid molecule encoding a Ubv polypeptide, or a fragment thereof. Optionally, the Ubv polypeptide is a Ubv polypeptide as described herein, or a fragment thereof, or the nucleic acid molecule is a nucleic acid molecule as described herein, or a fragment thereof. The agent may have specificity for a particular HECT E3 ligase, or may be active against more than one HECT E3 ligase. In certain embodiments, the HECT E3 ligase is in a cell, which may optionally be within a subject (e.g., a human subject), who optionally has a disease or condition selected from the group consisting of hypertension, inflammation, and cancer. In a related aspect, the invention provides methods of treating hypertension, inflammation, or cancer in a subject (e.g., a human subject), by modulating (e.g., increasing or decreasing) the activity of a HECT E3 ligase in a cell of the subject according to the methods as described herein.

In a further aspect, the invention includes methods of identifying agents that modulate the activity of a HECT E3 ligase. These methods optionally include contacting a complex including a HECT E3 ligase and a Ubv polypeptide that binds to the HECT E3 ligase with a candidate agent (e.g., a small molecule compound or a peptide), and determining whether the agent affects the binding of the Ubv to the HECT E3 ligase or an activity of the complex. In various embodiments, the HECT E3 ligase is selected from the group consisting of NEDD4 (N4), NEDD4L (NL), ITCH (IT), SMURF1 (S1), SMURF2 (S2), WWP1 (P1), WWP2 (P2), HECW1 (W1), HECW2 (W2), RSP5 (R5), HERC1 (H1), HERC2 (H2), HERC3 (H3), HERC4 (H4), HERC5 (H5), HERC6 (H6), HACE1 (HA), HUWE1 (HU), UBE3A (3A), UBE3B (3B), UBE3C (3C), HECTD1 (D1), EDD1 (ED), KIAA0317 (KI), HECTD1, HECTD2, HECTD3, HECTD4, G2E3, and TRIP12. In further embodiments, the Ubv polypeptide is selected from a Ubv polypeptide as described herein, or a fragment thereof.

Other features and advantages of the invention will be apparent from the following detailed description, the drawings, and the claims.

DETAILED DESCRIPTION

Figure 1:
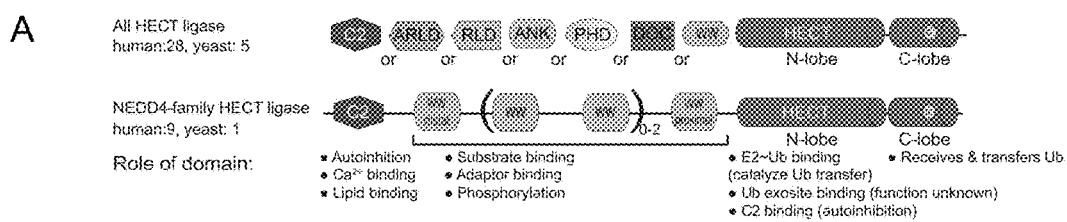
FIG. 1. A panel of high affinity ubiquitin variants (UbVs) that bind selectively across the HECT E3 family. (A) Schematic diagrams of HECT E3 ligases, with variable N-terminal domains and a conserved C-terminal HECT domain comprised of N- and C-lobes. The variable region of the largest HECT family (NEDD4-family) contains an N-terminal C2 domain and 2-4 WW domains. Domain functions are listed. (B) Phage display selection of UbVs binding to HECT E3 ligases, adapted with modification from (Zhang and Sidhu, 2014). See Experimental Procedures for details. (C) The binding specificities of phage-displayed UbVs (x-axis, detailed sequence information in Table 3) are shown across the HECT family (y-axis), as assessed by phage ELISA. Cognate HECT E3s are noted on top of individual graphs. Sub-saturating concentrations of phage were added to immobilized proteins as indicated (20 HECT domains and 4 control proteins, GST, BSA, and NA (neutravidin), and SA (streptavidin)). Bound phage were detected by the addition of anti-M13-HRP and colorimetric development of TMB peroxidase substrate. The mean value of absorbance at 450 nm is shaded in a purple gradient (white=0, black=2.2 or greater signal). (D) Sequence identity matrix shows conservation amongst the 20 HECT domains, but not negative control proteins shown in (C) (white=0 and black=100% identity).
Figure 1:
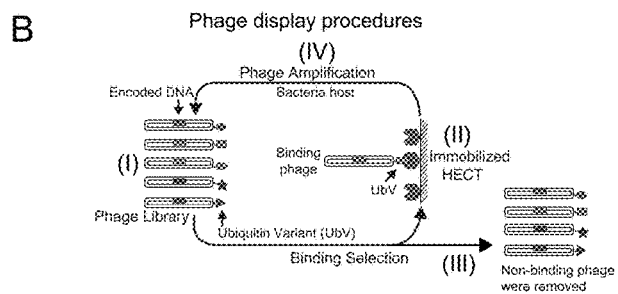
Figure 1:
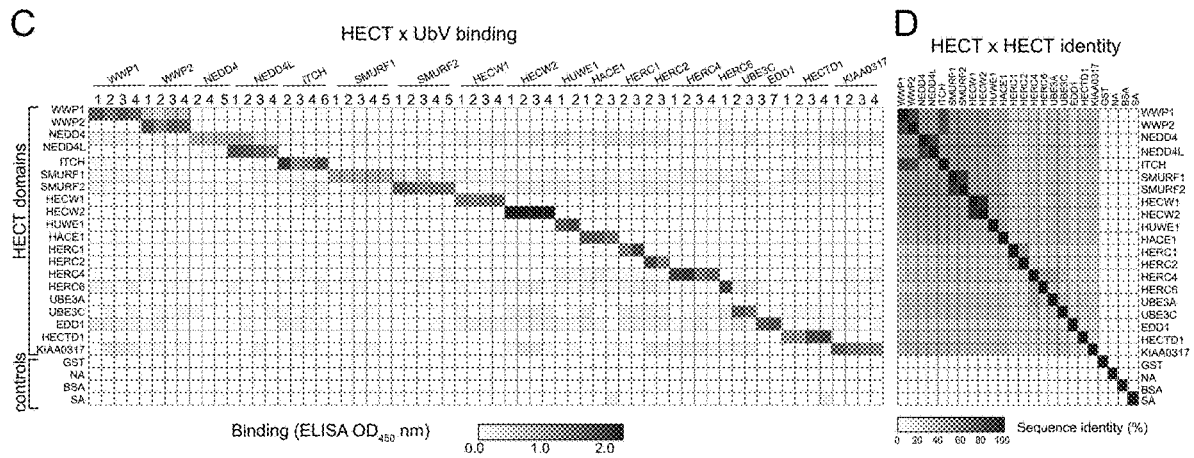

The attachment of ubiquitin (Ub) to target proteins involves the activities of Ub-activating enzymes (E1 enzymes), Ub-conjugating enzymes (E2 enzymes), and Ub ligases (E3 enzymes). Ubiquitination can alter the properties of target proteins in many ways, including directing them to the proteosome for degradation, as well as altering their cellular localization, activities, and/or interactive properties with respect to other proteins. Modification of ubiquitination thus provides an opportunity to modify a very wide variety of different cellular functions, in many contexts.

The present invention provides ubiquitin (Ub) variants, or UbVs, which target a particular family of E3 ligases, HECT E3 ligases. The invention also provides nucleic acid molecules encoding such UbVs, as well as related vectors and cells. In addition, the invention provides methods for identifying and characterizing new HECT E3 ligase-specific UbVs. Furthermore, the invention provides methods of using UbV polypeptides and related molecules. Examples of the latter include, for example, methods of identifying other modulators of HECT E3 ligase activity, as well as therapeutic methods involving HECT E3 ligase activity modulation. These and other aspects of the invention are described further, as follows.

The UbVs of the invention bind to or otherwise impact the activity of one or more HECT E3 ligase. The UbVs of the invention can have broad activity, against a wide range of HECT E3 ligases or, alternatively, may be relatively specific, modulating the activity of a small, related subset of HECT E3 ligases or even only a single, specific HECT E3 ligase. The UbVs modulate the activity of a HECT E3 ligase by, for example, increasing or decreasing the ligase activity. The modulation (increasing or decreasing of activity) can be by direct interaction with a HECT E3 ligase active site. In one example of such an interaction, a UbV binds the active site of a HECT E3 ligase with greater affinity than Ub, resulting in competitive inhibition. In another example, the UbV blocks the active site after an enzymatic reaction, resulting in product inhibition. Alternatively, the modulation may be by an allosteric means, in which the UbV, for example, binds outside of the active site and impacts activity. In addition, the UbVs can function by binding different sites on HECT E3 ligases including, for example, the E2 binding site on HECT E3 ligases and/or the N-lobe exosite of HECT E3 ligases.

HECT E3 ligases that can be targeted by the UbVs of the invention include, for example, the following human HECT E3 ligases: NEDD4 (N4), NEDD4L (NL), ITCH (IT), SMURF1 (S1), SMURF2 (S2), WWP1 (P1), WWP2 (P2), HECW1 (W1), HECW2 (W2), HERC1 (H1), HERC2 (H2), HERC3 (H3), HERC4 (H4), HERC5 (H5), HERC6 (H6), HACE1 (HA), HUWE1 (HU), UBE3A (3A), UBE3B (3B), UBE3C (3C), HECTD1 (D1), EDD1 (ED), KIAA0317 (KI), HECTD2, HECTD3, HECTD4, G2E3, and TRIP12. Additional HECT E3 ligases that can be targeted include HECT E3 ligases from budding yeast (e.g., Rsp5 (R5), Hul4, Hul5, Tom1, and Ufd4) and pathogenic bacteria *Salmonella* (SopA and NleL).

The UbVs of the invention comprise one or more mutation (e.g., substitution, deletion, addition, or modification) within any region or regions of a wild-type Ub. Using the sequence of human ubiquitin as a reference (SEQ ID NO:1), the UbVs can have mutations (e.g., substitutions or deletions) in one or more (e.g., 2, 3, 4, 5, 6, 7, 8, 9, 10, 11, 12, 13, or 14) amino acid in one or more of region 1 (amino acids 2-14), region 2 (42-49), or region 3 (62-78). A wild-type variant having two C-terminal glycines added to the sequence of SEQ ID NO:1 can also serve as a basis for generating UbVs. Furthermore, in addition to human Ub, the invention features UbVs obtained on the basis of Ub from other species and sources.

The sequence of Ub and specific examples of UbVs of the invention are provided in Table 1.

TABLE 1

| SEQ ID NO | UbV Name | Sequence |
| --- | --- | --- |
| 1. | Wild Type Ub | MQIFVKTLTGKTITLEVEPSDTIENVKAKIQDKEGIPPDQQRLIFAGK QLEDGRTLSDYNIQKESTLHLVLRLRGG[GG] |
| 2. | Ubv.IT.2 | MHILVKTLRGKTITLEVEPSDTIENVKAKIQDKEGIPPDQQRLLFGG NKLEDGRTLSDYNIQKESNLYLLLRRLGSKF |
| 3. | Ubv.IT.3 | MQIFVITHTWRTITLEVEPSDTIENVKAKIQDKEGIPPDQQRLLFAR QKLEDGRTLSDYNIQKDSTLHLVLIRRVSKR |
| 4. | Ubv.IT.4 | MQIFVKTLTGLSITTLEVEPSDTIENVKAKIQDKEGIPPDQQ1LIFGG KRLEDGRTLSDYNIQKKSSLYLLMRLRGVSR |
| 5. | Ubv.IT.6 | MPILVQTLRGQSIILEVEPSDTIENVKAKIQDKEGIPPDQQFLIFART HLEDGRTLSDYNIQKGSTLYLLLRFHGTVA |
| 6. | Ubv.N4.2 | MQIFVKTMRRESISLEVEPSDTIENVKAKIQDKEGIPPDQQRLFFTG KQLEDGRTLSDYNIQKESTLHLVKRLPGRQY |
| 7. | Ubv.N4.4 | MQIFVKTLAGWGITLEVEPSDTIENVKAKIQDKEGIPPDQQRLIFAG KQLEDGRTLSDYNIRYDSQLHLVGRLRGGGG |
| 8. | Ubv.N4.5 | MQIYVKTLTRKTITLEVEPSDTIENVKAKIQDKEGIPPDQQRLIFVGK QLEDGRTLSDYNIQKESSLYLVLRLRGGGG |
| 9. | Ubv.NL.1 | MRIFVRTPTRKTITLEVEPSDTIENVKAKIQDKEGIPPDQQVLIFAGN RLEDGRTLSDYNIPKESTLYLFMRLRGLEN |
| 10. | Ubv.NL.2 | MQILVKTPTWQTIFLEVEPSDTIENVKAKIQDKEGIPPDQQVLIFHG KKLEDGRTLSDYNIHHESNLYLFLKLPGLGD |
| 11. | Ubv.NL.3 | MQIFVWTLFRKPIILEVEPSDTIENVKAKIQDKEGIPPDQQRLIFAGK QLEDGRTLSDYNIQKESTLHLVLRLRGGGG |
| 12. | Ubv.NL.4 | MYIYVWTLFRKTITLEVEPSDTIENVKAKIQDKEGIPPDQQRLIFAG KQLEDGRTLSDYNIQKASLLHLVLRLRGGGG |
| 13. | Ubv.S1.1 | MHIFVKTLTGRVITLEVEPSDTIENVKAKIQDKEGIPPDQQTLLFGG KQLEDGRTLSDYNIYKVSTLYLLYRLRGGEL |
| 14. | Ubv.S1.2 | MQIFVQTYTWETITLEVEPSDTIENVKAKIQDKEGIPPDQQRLIFAG QQLEDGRTLSDYNIPKQSSLYLVLRLRGGGG |
| 15. | Ubv.S1.3 | MRIFVQTFTWKTITLEVEPSDTIENVKAKIQDKEGIPPDQQTLIFAG KQLEDGRTLSDYNIQKVSSLYLMFRLRGRSS |
| 16. | Ubv.S1.4 | MQIFVKTLTGKTITLEVEPSDTIENVKAKIQDKEGIPPDQQTLLFSG KQLEDGRTLSDYNIQQVSTLYLLFRLRGLRH |
| 17. | Ubv.S1.5 | MQIFMKTLPGKSIILEVEPSDTIENVKAKIQDKEGIPPDQQTLLFAG KRLEDGRTLSDYNIQNGSTLYLMPRLRGGGG |
| 18. | Ubv.S2.1 | MQIFVKTLTRKTITLEVEPSDTIENVKAKIQDKEGIPPDQQILVFAGK SLEDGRTLSDYNIQKGSSLWLKLRLRGGGG |

TABLE 1-continued

| SEQ ID NO | UbV Name | Sequence |
|---|---|---|
| 19. | Ubv.S2.2 | MQIFVKTPTRKSIALEVEPSDTIENVKAKIQDKEGIPPDQQILIFAGK QLEDGRTLSDYNIQMQSILYLLRRLPRVHA |
| 20. | Ubv.S2.3 | MQICVKTPTRKLINLEVEPSDTIENVKAKIQDKEGIPPDQQRLLFAG KQLEDGRTLSDYNIQQESTLYLVKRLRGGGG |
| 21. | Ubv.S2.4 | MLIFVWTFKGNTITLEVEPSDTIENVKAKIQDKEGIPPDQQRLIFAR KQLEDGRTLSDYNILKESTLLLVRRLRGGGG |
| 22. | Ubv.S2.5 | MQISVKTLSGKNITLEVEPSDTIENVKAKIQDKEGIPPDQQLLIFVGK NLEDGRTLSDYNILKYSTLYLLKGIRGREK |
| 23. | Ubv.P1.1 | MHIFVKTLRGWSITLEVEPSDTIENVKAKIQDKEGIPPDQQILIFARK KLEDGRTLSDYNIQEKSSLYLFLRLLRKSR |
| 24. | Ubv.P1.2 | MEIFVKTLSGKSITLEVEPSDTIENVKAKIQDKEGIPPDQQLLLFGG RQLEDGRTLSDYNIKYESTLSLLFRLRGYKV |
| 25. | Ubv.P1.3 | MRISVYTLPGKTIKLEVEPSDTIENVKAKIQDKEGIPPDQQLLIFAGR QLEDGRTLSDYNIQKESTLHLMLRLRGKAK |
| 26. | Ubv.P1.4 | MPILVKTLRGQSIILEVEPSDTIENVKAKIQDKEGIPPDQQFLIFARK HLEDGRTLSDYNIQKRSTLYLFLRFHGMVA |
| 27. | Ubv.P2.1 | MQIFVKTFTWKTITLEVEPSDTIENVKAKIQDKEGIPPDQQRLIFAG KQLEDGRTLSDYNILNESTLYLILRLPGFSV |
| 28. | Ubv.P2.2 | MLIFVKTFKWITITLEVEPSDTIENVKAKIQDKEGIPPDQQRLIFAGK QLEDGRTLSDYNIKNRSSLHLVLRLPGGRR |
| 29. | Ubv.P2.3 | MQILVKTFTWKTITLEVEPSDTIENVKAKIQDKEGIPPDQQRLIFAG KQLEDGRTLSDYNIKMGSSLYLVLRLPGQRI |
| 30. | Ubv.P2.4 | MQILVKTLTLKTIALEVEPSDTIENVKAKIQDKEGIPPDQQRLFFVG KQLEDGRTLSDYNIHNESTLYLALRLPVNRL |
| 31. | Ubv.W1.1 | MQISVKTLTGLSITLEVEPSDTIENVKAKIQDKEGIPPDQQILIFASK KLEDGRTLSDYNIHKESILHLLRRLPDSHT |
| 32. | Ubv.W1.2 | MQILVRTLTRKTICLEVEPSDTIENVKAKIQDKEGIPPDQQRLIFAGK QLEDGRTLSDYNIQKGSRLHLLKRLPWRRT |
| 33. | Ubv.W1.3 | MTIFVKTLRRTTITLEVEPSDTIENVKAKIQDKEGIPPDQQQLIFGAK KLEDGRTLSDYNIKNQSSLHLLKKLLVTPL |
| 34. | Ubv.W1.4 | MTIFVKTLRRTTITLEVEPSDTIENVKAKIQDKEGIPPDQQQLIFGAK KLEDGRTLSDYNIKNQSSLHLLKKLLVTPL |
| 35. | Ubv.W2.1 | MQIVVGTLTGKPITLEVEPSDTIENVKAKIQDKEGIPPDQQLLIFAGK QLEDGRTLSDYNIRRQSILSLVMRLRGDKP |
| 36. | Ubv.W2.2 | MQILVGTLTGKTITLEVEPSDTIENVKAKIQDKEGIPPDQQRLIFAGK QLEDGRTLSDYNIQNASILTLFLRLRIMTV |
| 37. | Ubv.W2.3 | MQIVVGTLTGKPITLEVEPSDTIENVKAKIQDKEGIPPDQQLLIFAGK QLEDGRTLSDYNIRRQSILSLVMRLRGDKP |
| 38. | Ubv.W2.4 | MPIIVGTLTGKTITLEVEPSDTIENVKAKIQDKEGIPPDQQRLIFAGK NLEDGRTLSDYNIQNESSLTLVLRRHVVRN |
| 39. | Ubv.R5.1 | MQILVKTPAGKTITLEVEPSDTIENVKAKIQDKEGIPPDQQRLIFTGK QLEDGRTLSDYNIQKVSTLHLVKRLPPSVV |
| 40. | Ubv.R5.2 | MRILVKTPTRKTINLEVEPSDTIENVKAKIQDKEGIPPDQQKLIFVGK PLEDGRTLSDYNIQKESTLYLVFRLPVPRK |
| 41. | Ubv.R5.3 | MQIAVKTPTRQTITLEVEPSDTIENVKAKIQDKEGIPPDQQRLIFAG KQLEDGRTLSDYNIQKESTLHLVKRLPGHSD |
| 42. | Ubv.R5.4 | MQIFVKTPTRKSISLEVEPSDTIENVKAKIQDKEGIPPDQQRLIFAG KQLEDGRTLSDYNIQKESTLHLVLRLPGTIK |
| 43. | Ubv.R5.5 | MHIFVKTPTRKTIILEVEPSDTIENVKAKIQDKEGIPPDQQRLIFAGT QLEDGRTLSDYNIQNYSTLHLVRRLPGKSR |
| 44. | Ubv.R5.6 | MQILVKTPLAKDIRLEVEPSDTIENVKAKIQDKEGIPPDQQRLIFLGK QLEDGRTLSDYNIQKASNLYLVRRLPGMKW |

TABLE 1-continued

| SEQ ID NO | UbV Name | Sequence |
|---|---|---|
| 45. | Ubv.H1.2 | MLIFVNTFMRYPITLEVEPSDTIENVKAKIQDKEGIPPDQQRLIFSG KQLEDGRTLSDYNIKKESTLHLVLRLRGGGG |
| 46. | Ubv.H1.3 | MQILVKTPMRKSITLEVEPSDTIENVKAKIQDKEGIPPDQQRLIFAG KQLEDGRTLSDYNIHNKSTLHLLVILRAWST |
| 47. | Ubv.H2.2 | MQIRVKTLTGNSITLEVEPSDTIENVKAKIQDKEGIPPDQQRLIFAW KELEDGRTLSDYNIKKWSFLHLVLRLRGNGY |
| 48. | Ubv.H2.3 | MHIFVSTGAGVSIILEVEPSDTIENVKAKIQDKEGIPPDQQSLFFVG NRLEDGRTLSDYNIQKASTLHLMLRLLGMGQ |
| 49. | Ubv.H4.1 | MQIFVKTLTGKTITLEVEPSDTIENVKAKIQDKEGIPPDQQRLIFAGK QLEDGRTLSDYNIQKESTLHLVLRPIWSKY |
| 50. | Ubv.H4.2 | MQIVVKTLTGKTITLEVEPSDTIENVKAKIQDKEGIPPDQQRLIFAGK QLEDGRTLSDYNIYKDSTLYLVLRFPYPKY |
| 51. | Ubv.H4.3 | MDIIVKTLNGKTITLEVEPSDTIENVKAKIQDKEGIPPDQQRLIFAGK QLEDGRTLSDYNIHKTSILHLVLRPPWAYT |
| 52. | Ubv.H4.4 | MQIFVKTLTGKTITLEVEPSDTIENVKAKIQDKEGIPPDQQRLIFAGK QLEDGRTLSDYNIQKVSSLYLVYRPLWSTQ |
| 53. | Ubv.H6.1 | MKISVETHSDKTIILEVEPSDTIENVKAKIQDKEGIPPDQQRLFFSG KQLEDGRTLSDYNIQRVSRLHLVFRLRGGGG |
| 54. | Ubv.HA.1 | MQIFVHTLTGKIIRLEVEPSDTIENVKAKIQDKEGIPPDQQRLLFRSK QLEDGRTLSDYNILKESWLRLILRLRGGGG |
| 55. | Ubv.HA.2 | MQIFVKTITWHPITLEVEPSDTIENVKAKIQDKEGIPPDQQRLIFAGK QLEDGRTLSDYNIQHGSTLFLVFTRRGRMV |
| 56. | Ubv.HA.3 | MHIFVKTLKGMGIALEVEPSDTIENVKAKIQDKEGIPPDLQRLIFAG KQLEDGRTLSDYNIQKGSILHLRLILRVSRS |
| 57. | Ubv.HU.1 | MQIFVVTPGVKSITLEVEPSDTIENVKAKIQDKEGIPPDQQRLIFAG KQLEDGRTLSDYNIQQKSTLFLLLRTLGSIA |
| 58. | Ubv.HU.2 | MHIFVKTLPGKIITLEVEPSDTIENVKAKIQDKEGIPPDQQRLIFAGK QLEDGRTLSDYNIQKVSNLNLWLRIHGDFK |
| 59. | Ubv.3C.2 | MHIFVKTLIVQIIPLEVEPSDTIENVKAKIQDKEGIPPDQQRLIFAGKI LEDGRTLSDYNILRDSTLYLLFRLRGGGG |
| 60. | Ubv.3C.3 | MDIFVSTLTVNTIPLEVEPSDTIENVKAKIQDKEGIPPDQQRLIFAGK QLEDGRTLSDYNIQKWSRLLLVLRLRGGGG |
| 61. | Ubv.D1.1 | MLICVVTVTGLTITLEVEPSDTIENVKAKIQDKEGIPPDQQGLVFAG MKLEDGRTLSDYNIQKESSLHLVVSLPVRSS |
| 62. | Ubv.D1.2 | MQILVRTLTGKTIRLEVEPSDTIENVKAKIQDKEGIPPDQQRLIFAG MRLEDGRTLSDYNIQGFSPLGLVLRLLRVEL |
| 63. | Ubv.D1.3 | MQIFVKTVSGKTINLEVEPSDTIENVKAKIQDKEGIPPDQQGLIFAR KRLEDGRTLSDYNIQDESNLHLVLTLVGRNL |
| 64. | Ubv.D1.4 | MAILVKTVTGNSITLEVEPSDTIENVKAKIQDKEGIPPDQQGLLFAR TRLEDGRTLSDYNIQKASTLHLVRTLRGTDT |
| 65. | Ubv.ED.3 | MSIFVITFTRKPITLEVEPSDTIENVKAKIQDKEGIPPDQQILIFAGKK LEDGRTLSDYNIQKESSLYLFLRLRGAKV |
| 66. | Ubv.ED.7 | MQISVVTLTRPTITLEVEPSDTIENVKAKIQDKEGIPPDQQRLIFAGR DLEDGRTLSDYNIQKQSSLHLFFRLRGSVS |
| 67. | Ubv.KI.1 | MLIFVNTRPWKTISLEVEPSDTIENVKAKIQDKEGIPPDQQILFFGG KQLEDGRTLSDYNIPNKSILHLRLRPRIKRQ |
| 68. | Ubv.KI.2 | MQIFVQTLMGDNISLEVEPSDTIENVKAKIQDKEGIPPDQQRLIFAD NQLEDGRTLSDYNIKKKSHLLLLLRPRGYRS |
| 69. | Ubv.KI.3 | MQIFVKTLIGYTIPLEVEPSDTIENVKAKIQDKEGIPPDQQRLIFAGK QLEDGRTLSDYNICQESNLHLAFPLPGDEE |

TABLE 1-continued

| SEQ ID NO | UbV Name | Sequence |
|---|---|---|
| 70. | Ubv.KI.4 | MQIFVKTFSGKYITLEVEPSDTIENVKAKIQDKEGIPPDQQRLTFVA KQLEDGRTLSDYNIQKGSALRLILQRRGNHD |

In addition to UbVs having the sequences set forth above, the invention includes variants of these and other UbVs. Thus, for example, the invention includes polypeptides having at least 80%, 85%, 95%, or 99% sequence identity to a UbV, such as a UbV described herein. The invention also includes UbV variants having one or more (e.g., 2, 3, 4, 5, 6, 7, 8, 9, 10, or more) substitutions (e.g., conservative amino acid substitutions) and/or deletions relative to a sequence provided herein. Also see the formula in the Summary of the Invention, above.

A "conservative" amino acid substitution as used herein, is one in which one amino acid residue is replaced with another amino acid residue having similar properties. Conservative substitutions typically include substitutions within the following groups: glycine and alanine; valine, isoleucine, and leucine; aspartic acid, glutamic acid, asparagine, and glutamine; serine and threonine; lysine and arginine; and phenylalanine and tyrosine. In more detail, conserved amino acid substitutions involve replacing one or more amino acids of the polypeptides of the invention with one or more amino acids of similar charge, size, and/or hydrophobicity characteristics. When only conserved substitutions are made, the resulting molecule may be functionally equivalent or similar to the original molecule. Changes that result in production of a chemically equivalent or chemically similar amino acid sequence are included within the scope of the invention. In various examples, a hydrophobic residue, such as glycine, can be substituted for another hydrophobic residue such as alanine. An alanine residue may be substituted with a more hydrophobic residue such as leucine, valine, or isoleucine. A negatively charged amino acid, such as aspartic acid, may be substituted for glutamic acid. A positively charged amino acid such as lysine may be substituted for another positively charged amino acid, such as arginine. The phrase "conservative substitution" also includes the use of a chemically derivatized residue in place of a non-derivatized residue, provided that such polypeptide displays a requisite activity.

The invention includes polypeptides that comprise the sequences of the UbVs described herein, in addition to other sequences. Thus, for example, the invention includes fusion proteins comprising the UbVs (and variants thereof) described herein (e.g., fusions with GST, His, Flag, or Myc tags). In addition, the invention includes fragments of the UbVs (and variants thereof) described herein. Such fragments include, for example, a UbV (or variant thereof) having 1-30 (e.g., 2-25, 4-30, or 5-10) amino acids deleted from either or both ends of the UbV (or variant thereof). Internal deletions are also included in the invention. The fragments can optionally be comprised within a fusion protein, as described above in connection with full-length UbVs. Optionally, UbV variants and fragments maintain, at least in part, one or more activities of the UbV from which they are derived. The fragments can further optionally comprise one or more region of a UbV, as described herein (e.g., region 1, region 2, region 3, region 1 and 2, region 2 and 3, etc.)

The UbVs of the invention can be used to obtain or design peptide mimetics, which are also included in the invention. Peptide mimetics include synthetic structures that may serve as substitutes for peptides in interactions between molecules, and include synthetic structures which can optionally contain amino acids and/or peptide bonds, but are designed to retain the desired structural and functional features and thus may be suitable substitutes of the peptide inhibitor analog disclosed herein. Peptide mimetics also include molecules incorporating peptides into larger molecules with other functional elements (e.g., as described in WO 99/25044). Peptide mimetics also include peptoids, oligopeptoids (Simon et al (1972) Proc. Natl. Acad. Sci. USA 89:9367), and peptide libraries containing peptides of a designed length representing all possible sequences of amino acids corresponding to an isolated peptide of the disclosure. Peptide mimetics may be designed based on information obtained by systematic replacement of L-amino acids by D-amino acids, replacement of side chains with groups having different electronic properties, and by systematic replacement of peptide bonds with amide bond replacements. Local conformational constraints can also be introduced to determine conformational requirements for activity of a candidate peptide mimetic. The mimetics may include isosteric amide bonds, or D-amino acids to stabilize or promote reverse turn conformations and to help stabilize the molecule. Cyclic amino acid analogues may be used to constrain amino acid residues to particular conformational states. The mimetics can also include mimics of inhibitor peptide secondary structures. These structures can model the 3-dimensional orientation of amino acid residues into the known secondary conformations of proteins. Peptoids may also be used which are oligomers of N-substituted amino acids and can be used as motifs for the generation of chemically diverse libraries of novel molecules.

The UbVs described herein can be made using standard methods including, for example, recombinant methods. The UbVs may also be prepared by chemical synthesis using techniques well known in the art such as solid phase synthesis (Merrifield, J. Am. Chem. Assoc. 85:2149-2154 (1964); Frische et al., J. Pept. Sci. 2(4): 212-22 (1996)) or synthesis in homogenous solution (Houbenweyl, Methods of Organic Chemistry, ed. E. Wansch, Vol. 15 I and II, Thieme, Stuttgart (1987)). The UbVs of the invention typically comprise naturally occurring amino acids. However, UbVs including one or more non-naturally occurring amino acid are also included in the invention.

In addition to the UbVs described above, the invention provides nucleic acid molecules encoding the UbVs (e.g., nucleic acid molecules encoding UbVs of any one of SEQ ID NOs:2-70) and variants thereof, as described herein.

The term "nucleic acid molecule" as used herein refers to a sequence of nucleotide or nucleoside monomers consisting of naturally occurring bases, sugars, and intersugar (backbone) linkages. The term also includes modified or substituted sequences comprising non-naturally occurring monomers or portions thereof, which function similarly. The nucleic acid molecules of the present invention can be ribonucleic (RNA) or deoxyribonucleic acids (DNA), and can contain naturally occurring bases including adenine, guanine, cytosine, thymidine, and uracil. The sequences can also contain modified bases such as xanthine, hypoxanthine, 2-aminoadenine, 6-methyl, 2-propyl, and other alkyl adenines, 5-halo uracil, 5-halo cytosine, 6-aza uracil, 6-aza cytosine and 6-aza thymine, pseudo uracil, 4-thiouracil, 8-halo adenine, 8-amino adenine, 8-thiol adenine, 8-thio-alkyl adenines, 8-hydroxyl adenine and other 8-substituted adenines, 8-halo guanines, 8-amino guanine, 8-thiol guanine, 8-thioalkyl guanines, 8-hydroxyl guanine and other 8-substituted guanines, other aza and deaza uracils, thymidines, cytosines, adenines, or guanines, 5-trifluoromethyl uracil, and 5-trifluoro cytosine.

The term "isolated and purified" as used herein refers to a nucleic acid molecule, polypeptide, or peptide that is substantially free of cellular material or culture medium when produced by recombinant DNA techniques, or chemical precursors, or other chemicals when chemically synthesized. An "isolated and purified" nucleic acid molecule is also substantially free of sequences which naturally flank the nucleic acid (i.e., sequences located at the 5' and 3' ends of the nucleic acid) from which the nucleic acid molecule is derived.

Nucleic acid molecules encoding the UbVs can optionally be comprised within a vector, such as an expression vector. Exemplary vector types include cosmids, plasmids, or modified viruses (e.g. replication defective retroviruses, adeno-viruses, and adeno-associated viruses). The expression vectors can include a nucleic acid molecule encoding a UbV, as well as operatively linked regulatory sequences that are selected based on the type of host cells in which expression is to occur. "Operatively linked" is intended to mean that the nucleic acid molecule is linked to regulatory sequences in a manner that allows expression of the nucleic acid under the control of the regulatory element.

The invention thus includes recombinant expression vectors comprising a nucleic acid molecule encoding a UbV, as described herein, and optionally regulatory sequences that direct transcription of the nucleic acid molecule. Suitable regulatory sequences are known in the art and can be obtained from a variety of sources, including bacterial, fungal, viral, mammalian, and insect genes. Selection of appropriate regulatory sequences is dependent on the host cell chosen, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector. Furthermore, the recombinant expression vectors may also contain a selectable marker gene which facilitates the selection of host cells transformed or transfected with a recombinant molecule of the disclosure. Examples of selectable marker genes are genes encoding a protein such as G418 and hygromycin, which confer resistance to certain drugs, β-galactosidase, chloramphenicol acetyltransferase, firefly luciferase, or an immunoglobulin or portion thereof such as the Fc portion of an immunoglobulin optionally IgG. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors. It will be appreciated that selectable markers can be introduced on a separate vector from the nucleic acid of interest.

The recombinant expression vectors can also contain genes that encode a fusion moiety which provides increased expression of the recombinant protein; increased solubility of the recombinant protein; and aid in the purification of the target recombinant protein by acting as a ligand in affinity purification. For example, a proteolytic cleavage site may be added to the target recombinant protein to allow separation of the recombinant protein from the fusion moiety subsequent to purification of the fusion protein. Typical fusion expression vectors include pGEX (Amrad Corp., Melbourne, Australia), pMal (New England Biolabs, Beverly, Mass.), and pRIT5 (Pharmacia, Piscataway, N.J.), which fuse glutathione S-transferase (GST), maltose E binding protein, or protein A, respectively, to the recombinant protein.

Recombinant expression vectors can be introduced into host cells to produce transformed host cells, which are also included in the invention. Suitable host cells include a wide variety of eukaryotic host cells and prokaryotic cells. For example, the UbVs of the invention can be expressed in mammalian, insect, yeast, or bacterial cells (e.g., *E. coli*).

The nucleic acid molecules of the invention may also be chemically synthesized using standard techniques. Various methods of chemically synthesizing nucleic acid molecules are known, including solid-phase synthesis which, like peptide synthesis, has been fully automated in commercially available DNA synthesizers (see, e.g., Itakura et al., U.S. Pat. No. 4,598,049; Caruthers et al., U.S. Pat. No. 4,458,066; and Itakura, U.S. Pat. Nos. 4,401,796 and 4,373,071).

As noted above, the invention provides methods of identifying and characterized HECT E3 ligase-specific UbVs. Such UbVs can be obtained by screening libraries of Ub variants, which can be generated by randomizing the entire sequence of ubiquitin (SEQ ID NO:1) or particular regions (e.g., one or more of regions 1 (2-14), 2 (42-49), and 3 (62-78), or portions thereof). Randomization can be achieved using standard methods of genetic engineering. For example, variants can be created in which a particular residue is replaced with a different amino acid, such that a library of variants comprising all 20 amino acids in each position (e.g., within one or more of regions 1, 2, and 3) is produced. In one example, randomization is performed to yield 75% wild type amino acid residues and 25% mutated amino acid residues within, e.g., one or more of regions 1, 2, and 3.

UbV libraries (e.g., phage display libraries) can be screened against one or more HECT E3 ligase (e.g., see the list set forth above) and/or a fragment of one or more HECT E3 ligase. In one example, the libraries are screened against the HECT domain of one or more HECT E3 ligase (see, e.g., FIG. 1). UbVs identified as binding to a HECT E3 ligase (or fragment thereof) can then be subject to further characterization including, for example, assessment of binding affinity by $EC_{50}$ determination, specificity for particular HECT E3 ligases (or subgroups thereof), structural features (e.g., by co-crystallization analysis), and effects on ubiquitination. The latter effects of UbVs can be assessed using in vitro ubiquitination assays, as well as in cell-based assays that assess the effects of a UbV on downstream effects of ubiquitination involving a particular HECT E3 ligase. Details of exemplary assays that can be used in this aspect of the invention are provided in the Examples, below.

In addition to being identified and characterized in various assays, as described above, UbVs identified in the screening of libraries can be subject to further mutagenesis, in order to identify additional UbVs having desirable features. Thus, for example, UbVs found to have a desirable property (e.g., binding specificity), but lacking another features (e.g., binding affinity) can be further mutagenized and re-screened, optionally with the sequences of residues surmised by sequence analysis to be important with respect to the already obtained desirable property (e.g., binding specificity) maintained.

The invention also provides methods for modulating HECT E3 ligase activity. These methods include in vivo modulation of HECT E3 ligase activity by administration of a UbV as described herein, or a nucleic acid molecule encoding such a UbV (e.g., a nucleic acid molecule in an expression or delivery vector, such as a vector as described herein) to a subject (e.g., a human patient). Ex vivo methods, in which a UbV polypeptide or nucleic acid molecule is contacted with a cell or tissue that is then introduced into a subject for therapeutic purposes, are also included in the invention.

The therapeutic methods of the invention can be used in the prevention or treatment of diseases and conditions in which HECT E3 ligases have been implicated including, for example, cancer, hypertension, autoimmune diseases, and neurological disorders. Examples of cancer types that can be treated according to the methods of the invention include ovarian cancer, leukemia, lung cancer, colon cancer, CNS cancer, melanoma, renal cancer, prostate cancer, pancreatic cancer, and breast cancer. Specific examples of non-cancer diseases that can be treated according to the invention include Liddle's syndrome, Angelman disease, Angelman-like disease, Huntington disease, and Kaufman oculocerebrofacial syndrome. In addition, UbVs may be used therapeutically in the context of, for example, wound healing, transplantation, and organ culture, in view of the present observations relating to impact on cell migration. Furthermore, as HECT-like E3 ligases have been identified as virulence factors in certain pathogenic bacteria, UbV treatment can be used in the prevention and treatment of microbial infection.

The invention also includes methods of identifying additional agents that can be used to modulate HECT E3 ligase activity, and thus which can be used in the therapeutic methods described above. In such methods, a complex comprising a UbV and a HECT E3 ligase (or a fragment thereof, such as a HECT domain) is contacted with a candidate agent to determine whether the candidate agent impacts the ability of the UbV to bind to the HECT E3 ligase (or fragment thereof). An agent that affects the binding (e.g., decreases or increases the binding) can be considered as a candidate for modulation of HECT E3 ligase activity and, thus, may be considered for use in a therapeutic method (e.g., see above). Such candidate agents can be tested in an in vitro ubiquitination assay or in cell-based assays, such as those described herein. Candidate agents that can be screened in such assays include, e.g., peptides, nucleic acid molecules, natural products, and small organic or inorganic molecules. Such agents may be present in the context of a library, which can be tested in a high throughput manner.

The following non-limiting examples are illustrative of the present disclosure:

EXPERIMENTAL EXAMPLES

Development of Potent and Selective UbV Modulators for 20 HECT E3 Ligases

We used a phage-displayed UbV library that varies almost all residues contacting the N-lobe exosite but only a subset of those mediating interactions in the transient catalytic intermediates. Binding selections (FIG. 1B) against purified HECT domains for 19 of 28 total human and 1 of 5 total yeast HECT E3s (Table 2) yielded 69 UbVs with a variety of substitutions across the binding surface (Table 3). Assessment of affinities for cognate HECT domains by measuring $EC_{50}$ values (Table 4) confirmed higher affinity interactions for UbVs (in some cases $EC_{50}$<10 nM) than for Ub, which in accordance with previous studies showed no detectable binding even at micromolar concentrations. Tight binding was also confirmed by Bio-Layer Interferometry (BLI) (Table 5). Indeed, many UbVs bound their cognate HECT domains 500-1000-fold tighter than Ub (Table 5). Moreover, ELISAs revealed that the UbVs are highly specific, as most recognize preferentially their cognate HECT domain amongst a panel of 20 HECT domains and other control proteins (FIG. 1C-D). Even among the 9 most closely related HECT E3s in humans that comprise the NEDD4-family, for those related by ≤55% identity there was strong specificity, for example an average of 500-fold lower affinity for half the NEDD4L-binding UbVs toward WWP1 (52% identity) and 70-fold lower affinity of WWP1-binding UbVs toward NEDD4L. Although there is some cross-reactivity for HECT domains that are ≥80% identical (e.g., WWP2 UbVs to WWP1), four NEDD4L-binding UbVs displayed ≥14-fold selectivity over NEDD4 (Table 5). While a subset of UbVs selected with WWP2 showed cross-reactivity to its close homolog WWP1, those selected with NEDD4 and WWP1 were strikingly specific and did not cross-react with non-cognate E3s sharing >80% identity (Table 5).

Figure 2:
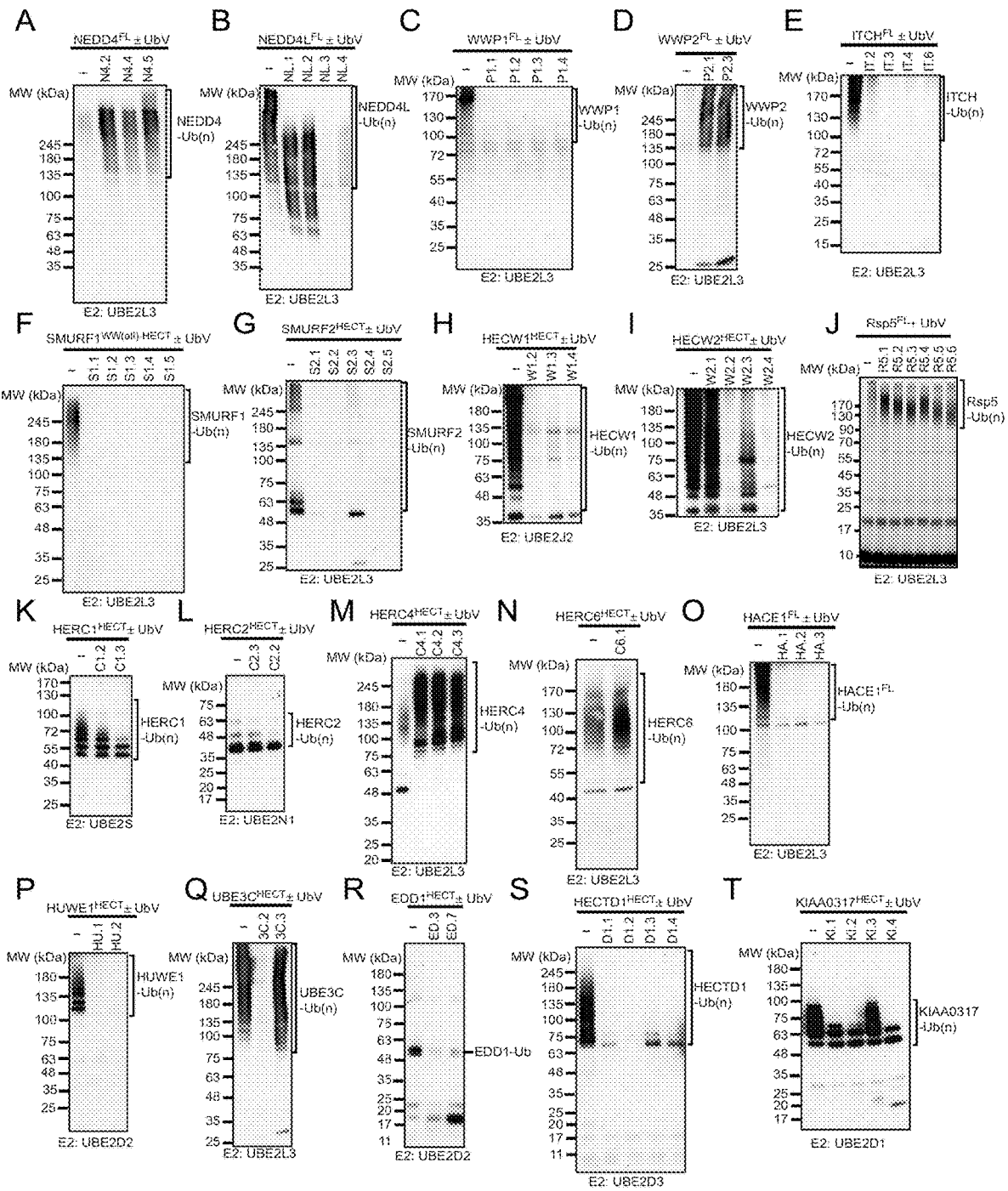
FIG. 2. Auto-ubiquitination assay for 20 HECT E3 ligases. (A) NEDD4 full-length (NEDD4$^{FL}$) protein (premixed for 15 min with wt Ub or UbV as indicated) was incubated for 1 hour at room temperature with E1 (UBE1), E2 (UBE2L3), ATP, and Ub. Western blots were probed with an anti-Ub antibody (clone FK2) to detect mono- and poly-ubiquitinated NEDD4$^{FL}$. UbVs are not incorporated into chains because their C termini do not contain a di-glycine motif that is required for recognition by the E1 enzyme. (B-T) Analysis of in vitro reactions to detect auto-ubiquitination of other members of the HECT E3 family under conditions described in (A). The following HECT E3s were analyzed: (B) NEDD4$^{FL}$, (C) WWP1$^{FL}$, (D) WWP2$^{FL}$ (E) ITCH$^{FL}$, (F) SMURF1$^{WW(all)\text{-}HECT}$, (G) SMURF2 HECT domain, (H) HECW1 HECT domain (UBE2J2 was used as E2), (I) HECW2 HECT domain, (J) Rsp5FL, (K) HERC1 HECT domain (UBE2S was used as E2), (L) HERC2 HECT domain (UBE2N1 was used as E2), (M) HERC4 HECT domain (UBE2L3 was used as E2), (N) HERC6 HECT domain (UBE2L3 was used as E2), (O) HACE1$^{FL}$ (UBE2L3 was used as E2), (P) HUWE1 HECT domain (UBE2D2 was used as E2), (Q) UBE3C HECT domain (UBE2L3 was used as E2), (R) EDD1 HECT domain, (UBE2D2 was used as E2), (S) HECTD1 HECT domain, (UBE2D3 was used as E2), and (T) KIAA0317 HECT domain. (UBE2D1 was used as E2). E2s were selected according to published work (Sheng et al., 2012).

Whereas previous studies confirmed that DUB catalytic activity is potently inhibited by associated UbVs targeting their substrate-binding sites (Ernst et al., 2013; Phillips et al., 2013; Zhang et al., 2013), we hypothesized that UbVs targeting different sites on HECT E3s may modulate ligase activity in a variety of ways that might not involve the active site. To explore how UbVs could influence intrinsic HECT ligase enzyme activity, we monitored E3 autoubiquitination and observed a wide range of effects for 65 UbVs assayed with 20 HECT E3s (FIG. 2). Indeed, many UbVs acted as inhibitors (e.g. WWP1 UbVs in FIG. 2C) but others massively increased ubiquitination (e.g. WWP2 UbVs in FIG. 2D). Unexpectedly, rather than having a switch-like activating or inhibiting effect, two UbVs that bind NEDD4L (NL.1 and NL.2) primarily altered extent of autoubiquitination in our assays (FIG. 2B).

UbV Inhibitors Hijack the E2 Binding Site

To gain insights into the basis for specific interactions and the mechanisms whereby UbVs inhibit, activate or modulate activity, we attempted co-crystallization of numerous HECT domain-UbV complexes, with or without E2s. We focused on members of the NEDD4-family because they regulate crucial physiological processes ranging from blood pressure to immunity, their catalytic mechanisms are better characterized than those of other HECT E3s (Scheffner and Kumar, 2014), and their UbVs displayed a perplexing variety of effects despite the perceived common catalytic mechanism across this subfamily (FIG. 2). We determined structures of six complexes (Table 6) that span a wide range of affinities with five different HECT domains (NEDD4L-NL.1-10 nM, Rsp5-R5.4-125 nM, WWP1-P2.3-230 nM, WWP1-P1.1-325 nM, ITCH-IT.2-≈10 µM and NEDD4-N4.4-≈90 µM) (Table 5), and that display inhibitory (P1.1, IT.2), activating (P2.3, N4.4) or modulatory (NL.1, R5.4) effects in autoubiquination assays, including a complex between WWP1 and a tightly binding UbV (P2.3) selected to bind the closely related WWP2. In all of the structures, UbV binding was mediated by a surface including the classic protein interacting hydrophobic patch (positions 8, 44, 68 and 70). Furthermore, all these HECT domains displayed one of two distinctive UbV binding modes described in detail below.

Figure 3:
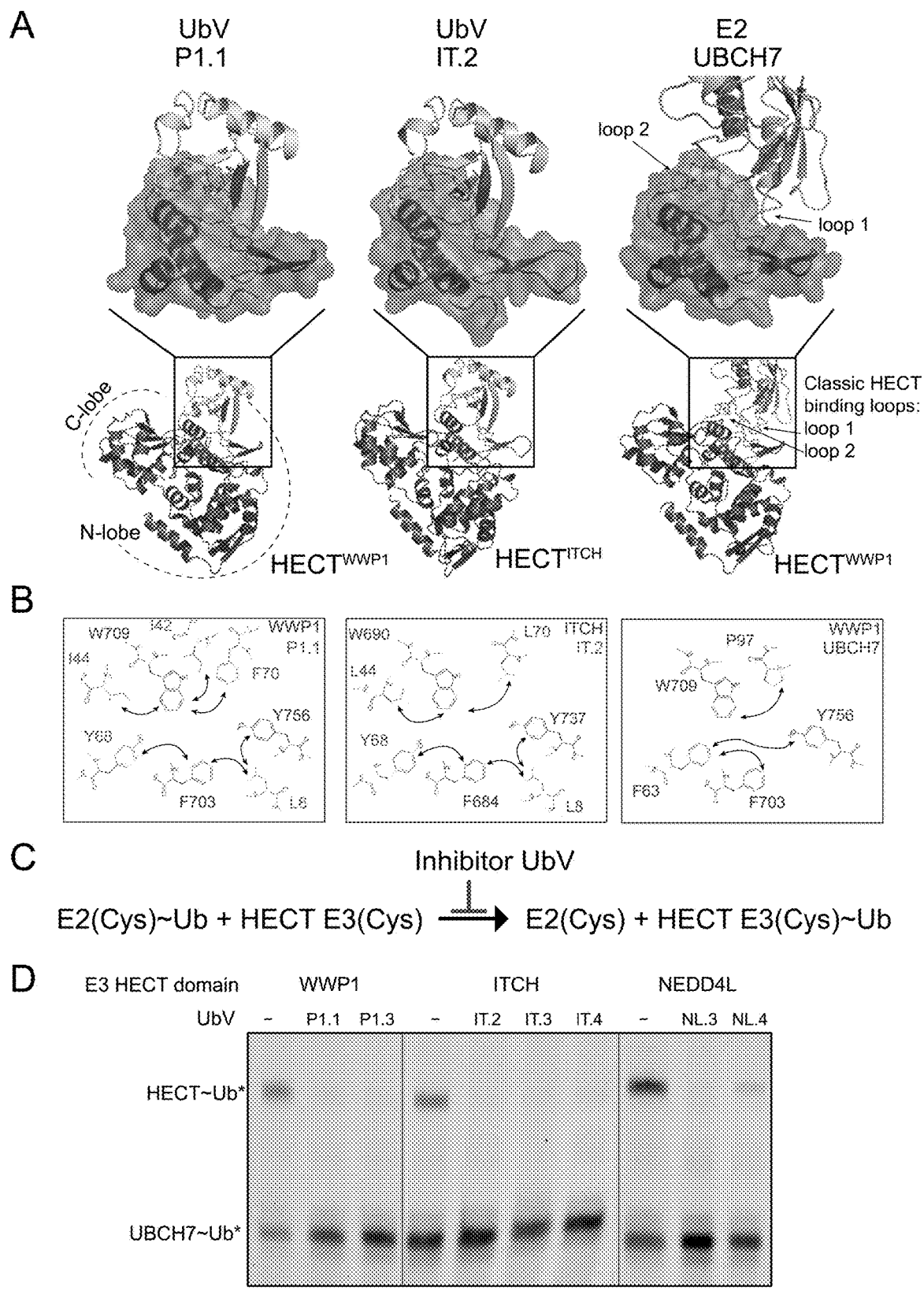
FIG. 3. UbV inhibitors block the E2-binding site. (A) Crystal structures of UbV P1.1 and IT.2 in complex with the HECT domains of WWP1 or ITCH, shown beside a complex of the WWP1 HECT domain and E2 enzyme UBCH7. Structures are shown aligned by the highlighted E2-binding subdomain. Details of interactions are in FIG. 8. (B) UbV hydrophobic patch residues hijack the canonical binding site for F63 and P97 from the E2 UBCH7 (Huang et al., 1999). (C) Schematic view of HECT E3 reaction involving E2, binding of which would be blocked by UbVs. (D) Phosphorimager data from pulse-chase assay showing transfer of fluorescent Ub to indicated E3 HECT domain, showing effects of selected inhibitory UbVs.

Unexpectedly, UbV P1.1 on WWP1 and UbV IT.2 on ITCH inhibit not by binding a known Ub-binding site, but rather, by occupying the E2-binding site (Huang et al., 1999), which appears to be partially mobile based on the variety of conformations observed in previous structures of WWP1, ITCH, and other HECT domains (FIG. 3A). Here, UbV blocks the E2 binding site, through hydrophobic patch residues 8, 44, 68 and 70 hijack the classic HECT E3 binding site for E2 loops 1 and 2 (F63 and P97, respectively, in a HECT-bound UBCH7) (Huang et al., 1999; Kamadurai et al., 2009) (FIG. 3B). The inhibitory interactions are stabilized by numerous additional interactions, including a UbV's β1/β2 loop inserting into a nearby flexible pocket (FIG. 8A-E). Accordingly, these UbVs inhibited HECT E3 activity by counteracting Ub transfer from E2 to E3 (FIGS. 2C, E and 3C-D).

N-lobe Exosite Bound UbVs Promote E3 Catalytic Activities

Figure 4:
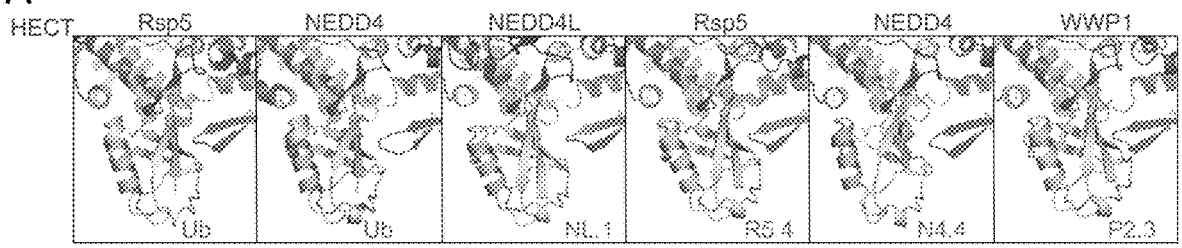
FIG. 4. UbV activators bind to the N-lobe exosite. (A) Close-up view of crystal structures of indicated HECT-Ub and HECT-UbV complexes, with HECT domains in magenta, Ub in olive, and UbVs in yellow. Details of interactions are in FIG. 9. (B) Scheme of pulse-chase reactions. A thioester-bonded E2~Ub intermediate was enzymatically generated using E1, E2 UBCH7, and fluorescently-labeled Ub. After quenching formation of the E2~Ub intermediate, various versions of HECT E3s were added either alone, or with the substrate WBP2 or free Ub. Reactions were monitored by following the fluorescent Ub, first in E2~Ub, then in E3~Ub, and were tested ultimately in substrate~Ub or Ub~Ub products. (C) Schematic diagrams of NEDD4L and WWP1 deletion mutants used in assays to define domains (C2, all WW domains, proximal WW domain, and/or catalytic HECT domain) required for UbV modulation of ubiquitination activities. (D) Pulse-chase reactions testing effects of UbVs (Top: UbV NL.1, Bottom: UbV NL.2) on NEDD4L-mediated Ub transfer from E2 to E3. Requirements of various E3 domains for UbV modulations were examined with four deletion constructs for each E3. For NEDD4L, the distal WW domains, present in NEDD4LFL and NEDD4$^{FL}$ and NEDD4L$^{WW(all)\text{-}HECT}$ but not NEDD4L$^{WW(proximal)\text{-}HECT}$, are required for UbV stimulation of catalysis. (E) Pulse-chase reactions testing effects of UbVs on free Ub chain formation by NEDD4L, from phosphorimager data monitoring effects of UbVs on fluorescent Ub transfer from an E2 (UBCH7), to the indicated WT or deletion mutant version of NEDD4L, to free Ub. (F) Pulse-chase reactions testing effects of UbVs on NEDD4L-mediated Ub transfer from E2 to E3 to substrate. These reactions require the WW domains for substrate recruitment. For NEDD4L, the distal WW domains, present in NEDD4L$^{FL}$ and NEDD4L$^{WW(all)\text{-}HECT}$ but not NEDD4L$^{WW(proximal)\text{-}HECT}$ are required for UbV stimulation of catalysis. (G) Sequence alignment of Ub and UbV NL.1. The white letters on a black background indicate identical sequences and the black letters on a grey background indicate similar sequences. Due to sequence identity with UbV NL.1, K27 and K29 linkage of Ub could not be absolutely quantified. (H-J) UB-AQUA proteomics of total Ub-diGly (H) and individual Ub chain linkage types (I) for in vitro NEDD4L reaction mixtures (45 min) and the effect of UbV NL.1. Error bars represent experimental triplicate measurements (±SEM). (J) UB-AQUA proteomics of individual Ub chain linkage types measured from whole cell lysate HEK293 cells expressing UbV NL.1 for the time indicated. Error bars represent biological triplicate measurements (±SEM). *: Amount quantified can be from Ub and/or UbV NL.1.
Figure 4:
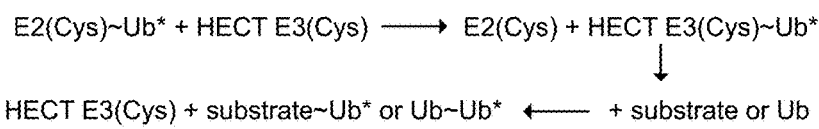
Figure 4:
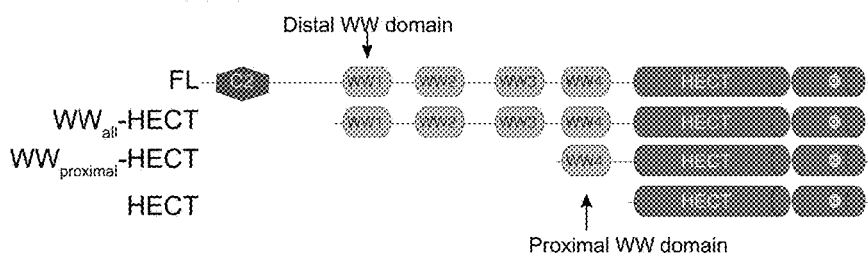
Figure 4:
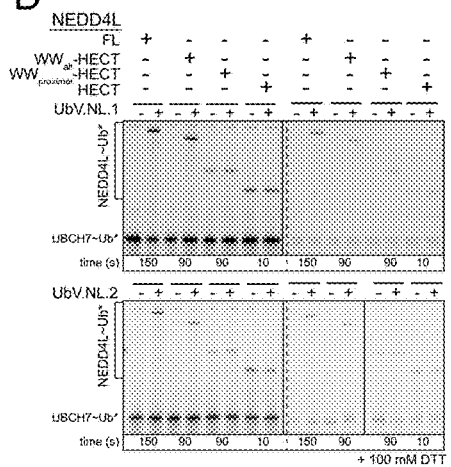
Figure 4:
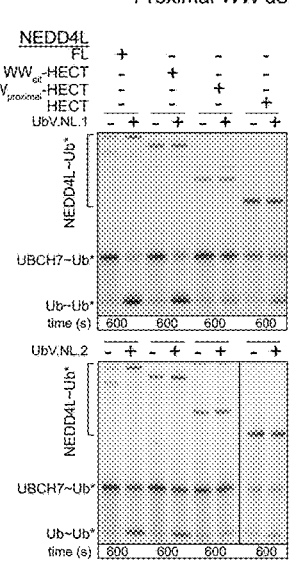
Figure 4:
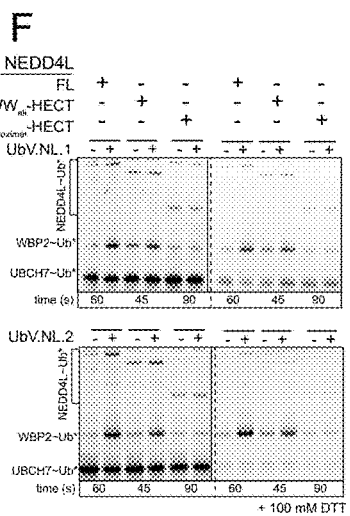
Figure 4:
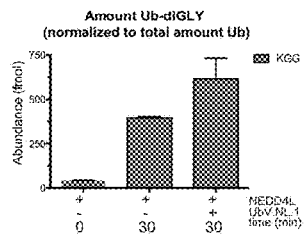
Figure 4:
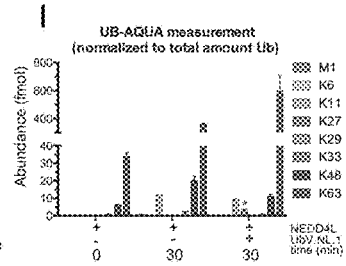
Figure 4:
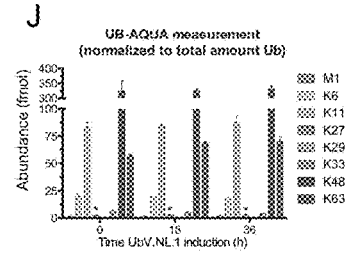
Figure 9:
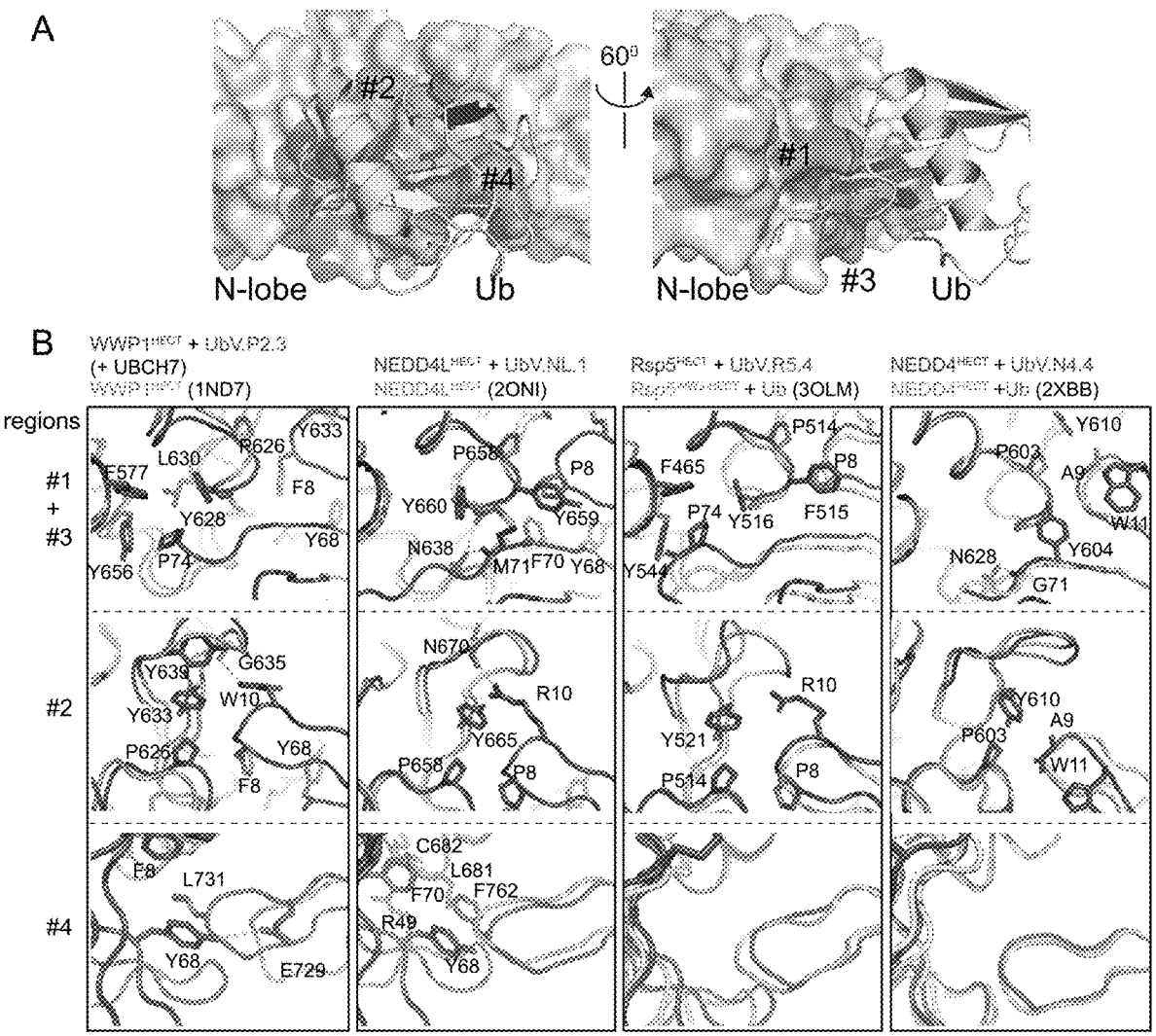
FIG. 9. Molecular details of activating or modulatory UbV-HECT E3 interactions. (A) Expanded views of Ub (yellow cartoon) bound to the N-lobe exosite on the NEDD4 HECT domain (surface) (PDB: 2XBB) highlighting locations of interacting regions 1-4. (B) Close-up views of HECT domain interactions with modulatory UbVs mimicking Ub bound to the N-lobe exosite. Structures were aligned over the HECT domain N-lobe and depicted with MacPyMol, with coloring of the proteins as labeled in the above panels. UbV complexes with HECT domains from WWP1 and NEDD4L are shown superimposed with prior structures of the free HECT domains to highlight striking conformational changes in region 4 upon UbV binding to WWP1. Rsp5 and NEDD4 complexes with UbVs and Ub are shown superimposed to highlight structural changes in the UbVs that may dictate specificity.

The other four structures showed UbVs binding the N-lobe exosite of NEDD4, NEDD4L, WWP1 or Rsp5 in a manner resembling the previously described binding of Ub at this site (Kim et al., 2011; Maspero et al., 2011) (FIG. 4A). The HECT domain N-lobe-Ub/UbV complexes superimpose with 0.8-1.5 Å RMSD overall, but also reveal details for how subtle differences can be exploited for specific noncovalent targeting at this site (FIG. 9A-B). Although previous mutagenesis studies probed roles of Ub binding to the N-lobe exosite, the interpretations have been inconclusive and controversial. Proposed functions have ranged from competition of Ub with the C2 domain to relieve E3 autoinhibition, binding of the acceptor Ub that receives Ub from the HECT active site, or binding of substrate-linked Ub chains to either stimulate or inhibit further chain elongation (French et al., 2009; Herrador et al., 2013; Kathman et al., 2015; Kim et al., 2011; Maspero et al., 2011; Ogunjimi et al., 2010). To date, it has not been possible to differentiate positive and negative roles of exosite Ub binding with deleterious mutations. By contrast, adding a UbV to the ubiquitination reaction can promote positive allosteric effects on the E3 while competing with prospective ubiquitinated substrates.

We therefore tested whether the NEDD4-family N-lobe exosite generally recruits an acceptor Ub and/or relieves allosteric autoinhibition mediated by the C2 domain. For NEDD4L and WWP1, we used pulse-chase assays that produce free Ub~Ub chains to monitor Ub transfer from the E3 to an acceptor Ub. Because rapid HECT E3 autoubiquitination precludes generation of stable HECT—Ub intermediates, we initiated the reactions with thioester-bonded E2~Ub intermediates for the E2 UBCH7 using a fluorescently-labeled version of Ub. Adding the E2~Ub to an active HECT E3 along with or without excess free Ub and substrate tests the effects of UbVs on E3-mediated Ub transfer from E2 to E3 to substrate or acceptor Ub. The reactions generate a thioester-bonded E3~Ub, isopeptide-linked Ub~Ub or ubiquitinated substrate product readily detected by SDS-PAGE (FIGS. 4B-F and 5A-C). Surprisingly, experiments performed in the presence of UbVs excluded previously hypothesized roles and instead identified novel functions for this exosite on NEDD4L and WWP1. Saturating the N-lobe exosite with a UbV did not inhibit Ub~Ub synthesis, ruling out the possibility that this site binds the acceptor Ub. Unexpectedly, these UbVs activated E3~Ub, Ub~Ub synthesis and substrate ubiquitination for multiple truncation mutants of both E3s, suggesting that the UbVs allosterically activate through mechanisms not involving the C2 domain (FIGS. 4D-F and 5A-C). Notably, occupation of the N-lobe exosite by a UbV has different effects on different HECT E3s, because all versions of WWP1 including the isolated HECT domain showed substantially activated Ub~Ub synthesis whereas inclusion of distal WW domains was required to observe dramatic UbV-mediated activation for NEDD4L (FIG. 5).

Figure 5:
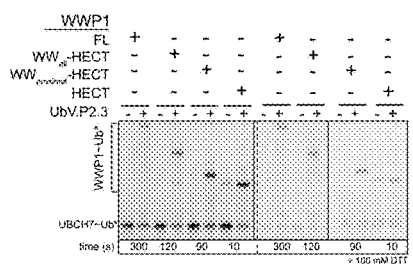
FIG. 5. UbVs binding to the N-lobe exosite differentially modulate related HECT E3 ligases. (A-C) Same reactions were performed as in FIG. 3D-F, except for the HECT E3 WWP1. UbV P2.3 can activate all versions of WWP1 from E2 to E3 then to substrate of Ub~Ub synthesis. (D) Schematic of mechanisms by which UbVs activate (GO) or inhibit (STOP) Ub transfer from an E2 to a HECT E3. To prevent HECT E3 autoubiquitination, E3s were mutated with an Ala substitution at a conserved Asp that is dispensable for Ub transfer from E2 to NEDD4-family HECT E3s but that is required for Ub transfer from NEDD4-family HECT E3s to lysines (Kamadurai et al., 2013). (E) Roles of distal WW domains in UbV modulation of Ub transfer from E2 (UBCH5B) to NEDD4L, assayed by titrating UbVs into reactions with versions of NEDD4L harboring all WW domains (NEDD4L$^{WW(all)\text{-}HECT}$) or only the proximal WW domain (NEDD4L$^{WW(proximal)\text{-}HECT}$) in addition to the catalytic HECT domain. The distal WW domains are required for NL.1 and NL.2 to stimulate catalysis, whereas NL.3 and NL.4 inhibit Ub transfer from E2 to both versions of the E3. Note different reaction times used to highlight activation or inhibition. (F) Same as (E), but for the E3 WWP1 and an activating UbV. Notably, for WWP1, even the isolated catalytic HECT domain alone is stimulated by the UbV in these reactions. (G) Models for different steps in Ub chain formation affected by UbVs binding to various NEDD4-family HECT E3s. For NEDD4L and Rsp5, UbV stimulation requires distal WW domains, potentially by releasing their autoinhibition. For WWP1, UbV stimulation only requires the HECT domain, which may be conformationally stabilized by UbV binding.
Figure 5:
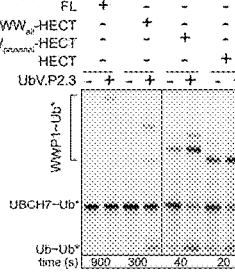
Figure 5:
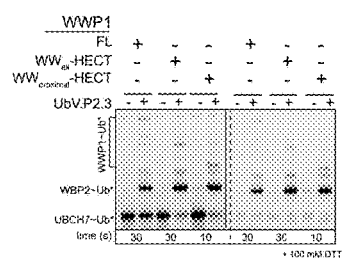
Figure 5:
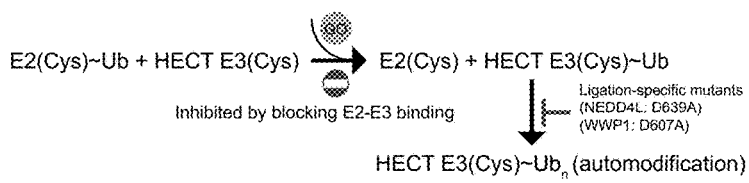
Figure 5:
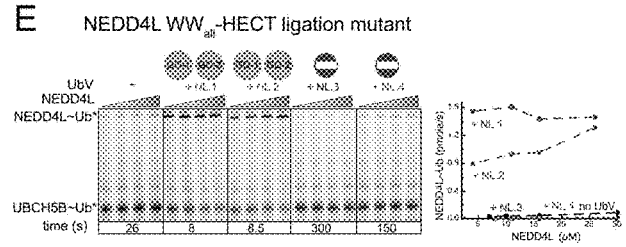
Figure 5:
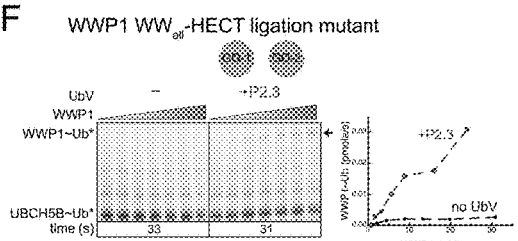
Figure 5:
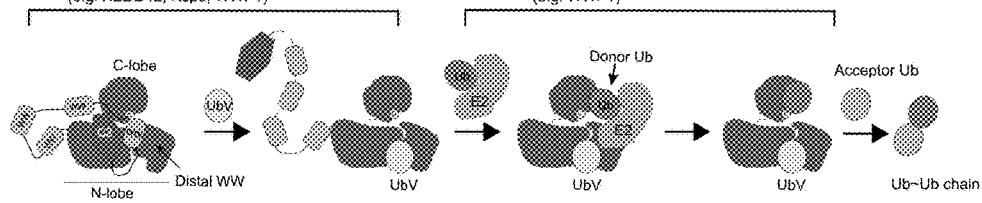
Figure 10:
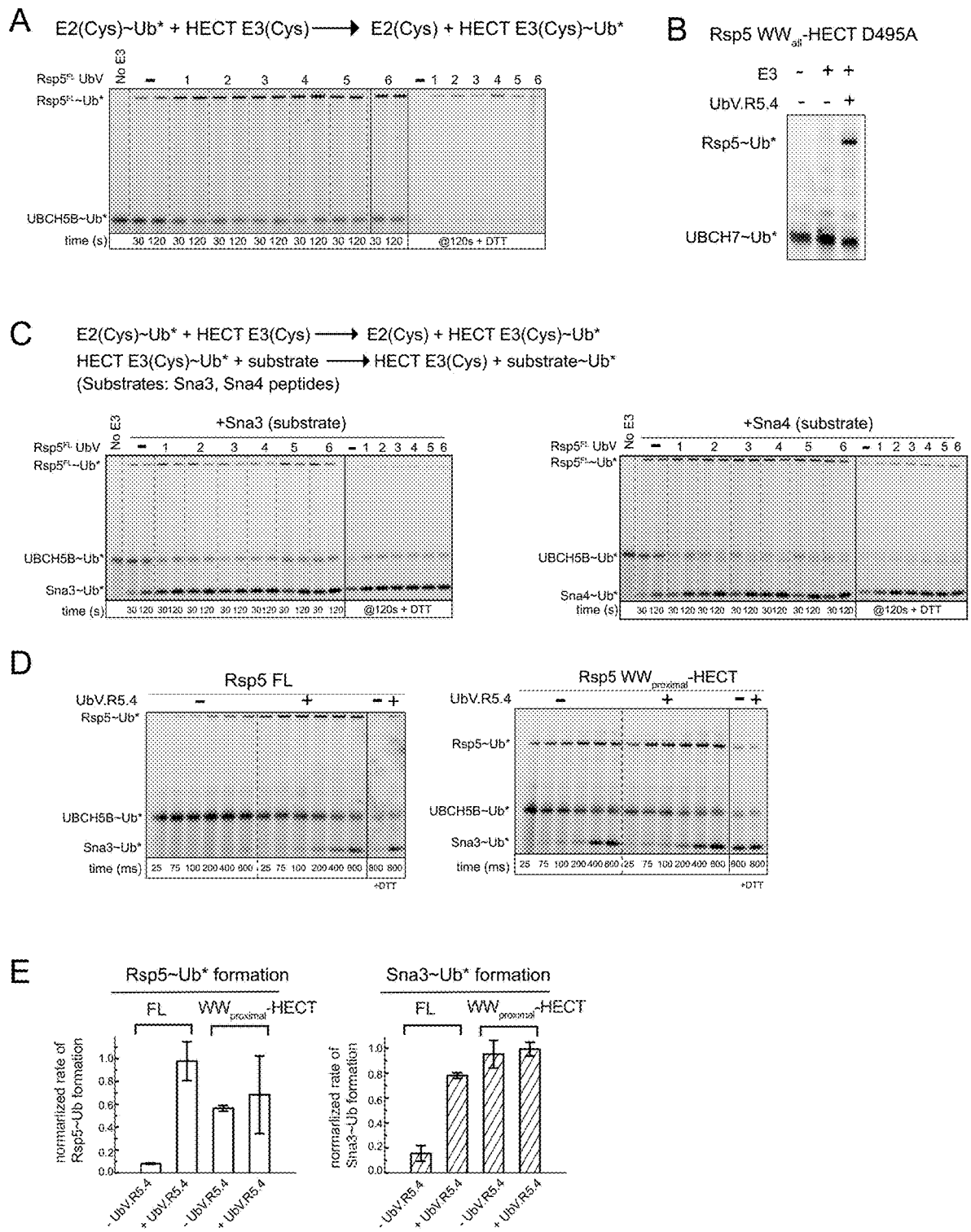
FIG. 10. UbVs stimulate Rsp5 activities in vitro. (A) Pulse-chase reactions showing six different UbVs stimulate fluorescent Ub transfer from E2 to the full-length Rsp5 E3. (B) Pulse-chase UbV R5.4, which was crystallographically shown to bind the Ub-binding exosite (FIG. 3A) stimulates Ub transfer from E2 to Rsp5 even in the absence of the C2 domain. (C) Pulse-chase reactions showing six different UbVs stimulate fluorescent Ub transfer from E2 to the full-length Rsp5 E3 to two substrates, Sna3 peptide (left) and Sna4 peptide (right). (D-E) Rapid quench-flow experiments confirm the crystallized UbV R5.4 stimulates the rate of Ub transfer from E2 to Rsp5 (~10-fold) and overall production of modified substrate (Sna3~Ub, ~4-fold). This stimulation mirrors the effect of removing the autoinhibitory N-terminal domain, as there is little effect of the UbV on the activated catalytic unit freed from autoinhibition (Rsp5$^{WW(proximal)-HECT}$) (Kamadurai et al., 2013).
Figure 11:
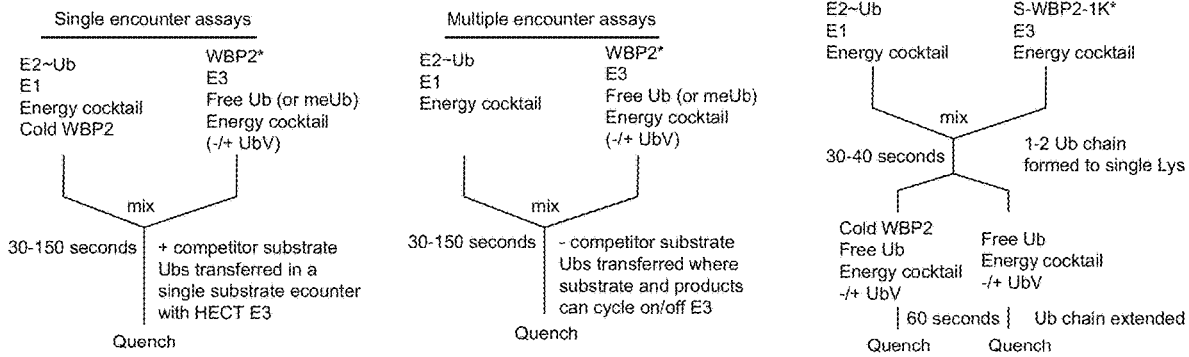
FIG. 11. UbVs targeting the HECT domain exosite exert different effects on NEDD4L and WWP1 in processive ligation of multiple monoUbs or polyUb chain formation, and in distributive reactions where substrates and products can cycle on and off E3. (A) Reaction flow-charts. Reactions in the presence of excess competitor substrate primarily monitor Ub transfer upon a single substrate encounter with E3, because fluorescent substrate or product released from E3 is generally replaced by an unlabeled counterpart not sensed in the reaction. Reactions performed with methylated Ub examine individual (mono) Ubs transfer to multiple substrate lysines in the absence of polyUb chain formation. The fluorescent substrate WBP2* has multiple lysines as potential Ub acceptors, whereas S-WBP2-1K* contains a single Lys that can serve as a site for Ub chain elongation. To monitor polyUb chain extension of pre-modified targets, a priming reaction first generated some S-WBP2-1K* modified with either a single Ub or a Ub~Ub chains. (B) Effect of UbV NL.1 on multi-mono-Ub transfer by a NEDD4L construct, either in a single substrate encounter with the E3 (left) or in multiple encounters (right) shows that occupation of the N-lobe exosite inhibits processive linkage of multiple monoUbs to a substrate. (C) Reactions as in B, except with wild-type Ub that can either be transferred to multiple substrate lysines and be incorporated into polyUb chains. (D-E) Reactions as in (B-C) except using NL.2 for NEDD4L. (F) Reactions as in B, except using the corresponding version of WWP1 and UbV P2.3, showing little effect of UbV on processive but enhanced distributive substrate modification with multiple mono Ubs. (G) Reactions as in (C), except using the corresponding version of WWP1, showing enhanced distributive substrate modification. (H-I) Limited effects of UbV NL.1 or NL.2 on polyUb chain formation by a version of NEDD4L, assayed by using a substrate harboring a single lysine acceptor site (S-WBP2-1K*). (J) Reactions as in H except with corresponding version of WWP1 and UbV P2.3 showing UbV stimulation of Ub chain elongation in distributive reactions.
Figure 11:
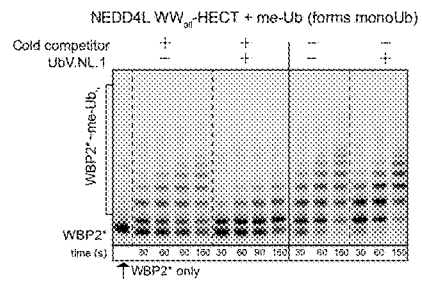
Figure 11:
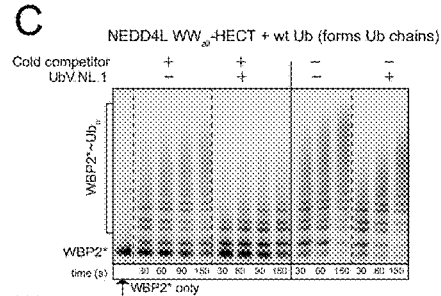
Figure 11:
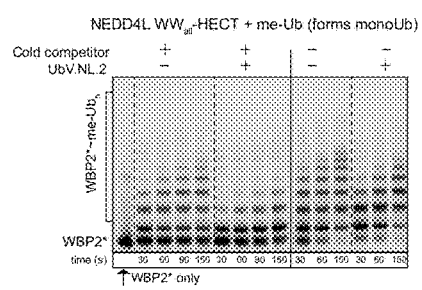
Figure 11:
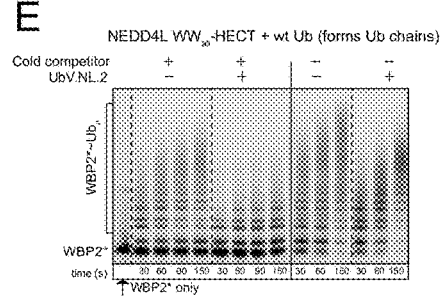
Figure 11:
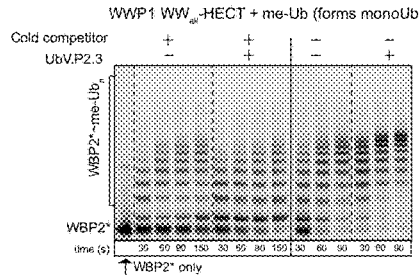
Figure 11:
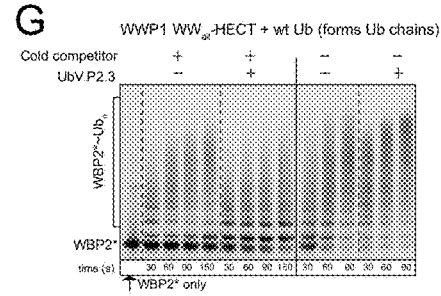
Figure 11:
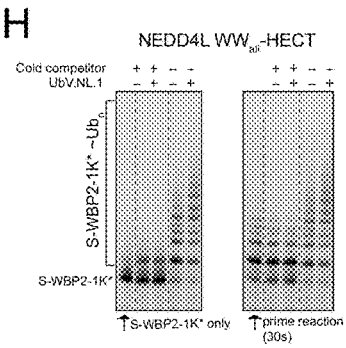
Figure 11:
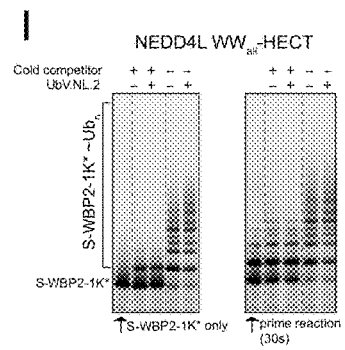
Figure 11:
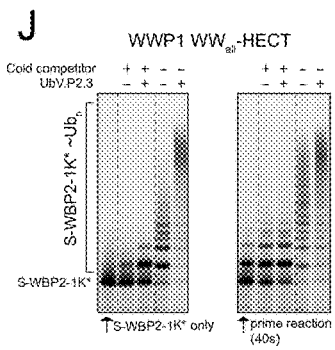

To further probe how UbVs differentially modulate HECT E3 activities, we performed a battery of experiments with various substrates using either WT Ub or methylated Ub that cannot form chains (FIGS. 5, 10, and 11). Taken together, our data imply that UbV occupation of the N-lobe exosite modulates activity through numerous mechanisms that were not previously reported. For example, for NEDD4L and Rsp5, N-lobe exosite-binding UbVs activated the transthioesterification reaction (Ub transfer from E2 to E3) in a manner that is independent of the C2 domain but depends on the distal WW domains, presumably by relieving their autoinhibition (FIGS. 4D, 4F, 5D-F, and 10B) (Riling et al., 2015). Intriguingly, two UbVs modulate NEDD4L activity by decreasing processive and increasing distributive multi-monoUb ligation directly to substrate, with slightly increased Ub chain elongation (FIGS. 11A-E and H-I). Thus, unlike previous reports on other NEDD4-family members that suggested blocking Ub binding primarily inhibits processive extension of a Ub chain (Kathman et al., 2015; Kim et al., 2011; Maspero et al., 2011; Maspero et al., 2013), our data demonstrate that occupation of the exosite positively and negatively influences many properties of the reaction. Accordingly, ubiquitination can be activated by relieving from autoinhibition and increased substrate turnover, yet individual substrate molecules may have fewer lysines modified at a time. Depending on reaction conditions, there may be increased flux through the pathway when NEDD4L is saturated with an exosite-binding UbV. Indeed, we used the UB-AQUA method, an unbiased proteomics approach for quantifying ubiquitin signaling (Kirkpatrick et al., 2005; Ordureau et al., 2015b; Ordureau et al., 2014; Phu et al., 2011), and found that NL.1 increased the total abundance of Ub chains, primarily containing canonical K63-linkages, formed on in vitro autoubiquitinated NEDD4L (FIG. 4G-I). Furthermore, this effect was also observed upon induction of NL.1 expression in HEK293 cells, which resulted in a ~20% increase in total K63-linked chains (FIG. 4J).

Interestingly, the effect of UbV binding to the N-lobe exosite on WWP1 differs from the effect on NEDD4L (FIGS. 5D-G and 11). Although UbV P2.3 slightly inhibits WWP1 reactions where a substrate molecule only encounters the E3 once, it massively increases the amount of substrate modified and the number of Ubs attached in reactions where ubiquitinated products that are released can re-bind WWP1 in numerous reaction cycles (FIG. 11F, G, J). The simplest interpretation is that UbVs block capture of a substrate-linked Ub and that this is less important for processive monoubiquitination of multiple sites during a single encounter with WWP1 than with NEDD4L. Instead, our data are consistent with a model where this is more important for reactions where ubiquitinated substrates come off and on E3s during repeated reaction cycles (FIG. 11B-E vs. F-G).

UbVs Modulate HECT E3 Functions in Cells and Intestinal Organoids (Mini-guts)

Figure 12:
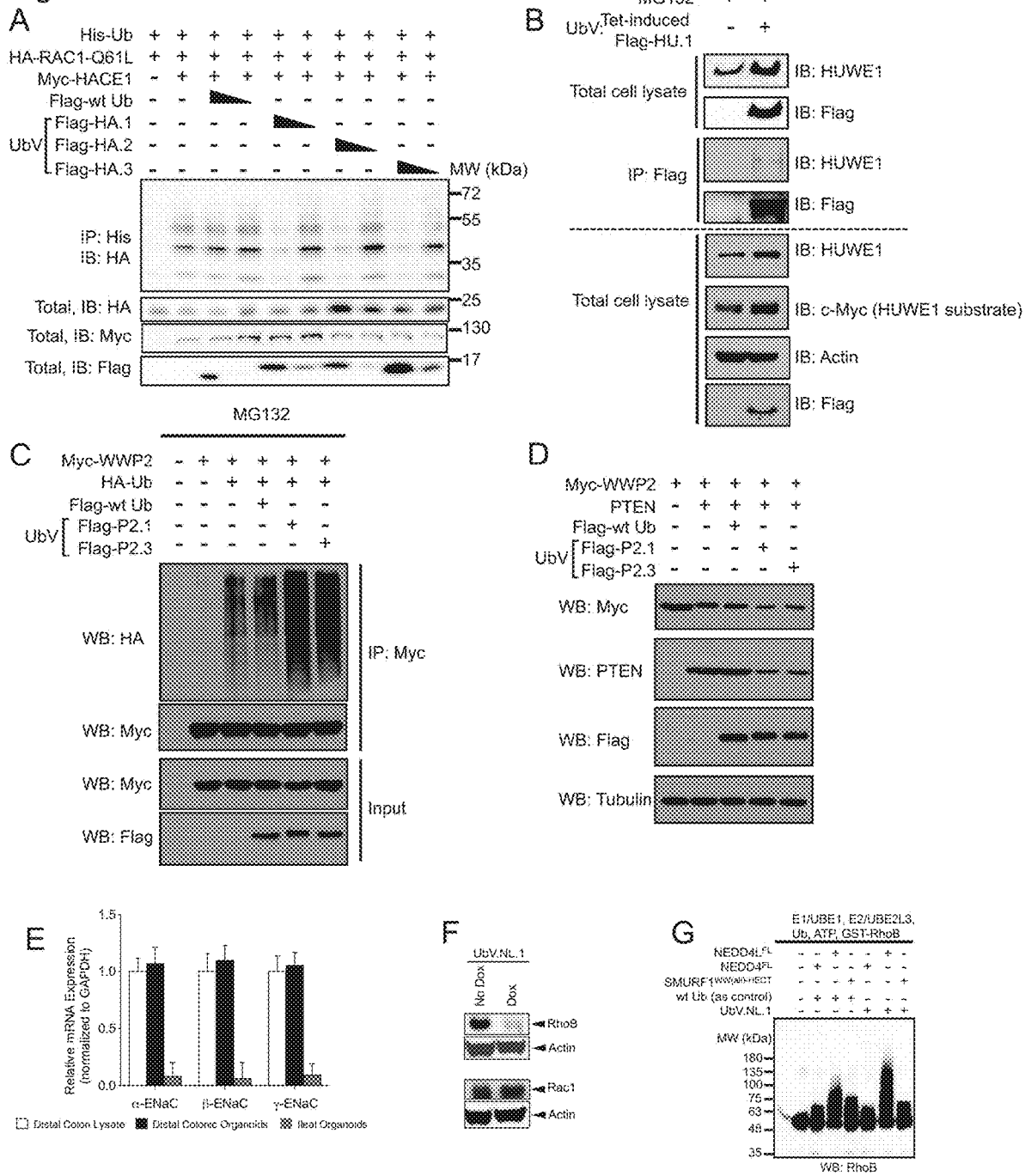
FIG. 12. UbVs interfere with HECT E3 activity in cells and tissues. (A) Western blotting analysis of HACE1-mediated Rac1 ubiquitination efficiency with and without HACE1 inhibitors UbV HA.1, HA.2 or HA.3. CHO cells were transfected with expression vectors for Histidine-tagged ubiquitin (His-Ub), together with HA-Rac1Q61L, myc-HACE1 and FLAG-Ub/HA.1/HA.2/HA.3. His-Ub crosslinked forms of Rac1Q61L were purified (IP—anti-His), resolved on SDS-PAGE and detected by immunoblot with anti-HA antibody (IB—anti-HA for ubiquitinated Rac1). Lower panels: Immunoblot (IB) with anti-HA, anti-myc or anti-FLAG were performed in parallel to verify quantities of protein expression. (B) HUWE1 inhibitor UbV HU.1 interacts with and stabilizes HUWE1 and its substrate c-Myc. The HCT116 cell line used stably expressed HU.1 (tet inducible). 24 hrs after induction, total lysate (2 mg) was immunoprecipitated with anti-FLAG antibody (4 μg) and immunoblotted with antibodies against endogenous HUWE1 and ectopically expressed FLAG-HU.1. Western blotting analysis of endogenous HUWE1, c-Myc and Actin are shown in the right panel. (C) WWP2 activators UbV P2.1 and P2.3 promote the poly-ubiquitination of WWP2 in vivo. 293T cells were transfected with constructs encoding HA-Ub and Myc-WWP2 together with constructs encoding FLAG-Ub/P2.1/P2.3. Cells were treated with 10 μM MG132 for 6 hrs. Whole cell lysates were subjected to immunoprecipitation with anti-Myc antibody and followed by western blotting using indicated antibodies. (D) WWP2 activators UbV P2.1 and P2.3 promote the degradation of WWP2 and PTEN. 293T cells were transfected with constructs encoding Myc-WWP2 together with FLAG-Ub/P2.1/P2.3. 24 hrs after transfection, cell lysates were immunoblotted with the indicated antibodies. (E) Three ENaC subunits were expressed in the organoids derived from the colon of the mice but not in the Ileum (negative control). (F) Expression of NL.1 destabilizes RhoB but not Rac1. Western blot analysis of whole-cell extracts from HCT116 cells with Dox-inducible, stable expression of NL.1. In the top two panels, the blot was probed with antibodies detecting RhoB and Actin as control. In the bottom two panels, the blot was probed with antibodies detecting Rac1 and Actin as control. (G) RhoB is ubiquitinated by NEDD4L in vitro. Meanwhile, NL.1 stimulated the activity of NEDD4L. NEDD4L, NEDD4, and SMURF1$^{WW(all)-HECT}$ (pre-mixed for 15 min with or without NL.1) were incubated for 1 hour at room temperature with E1 (UBE1), E2 (UBE2L3), ATP, Ub, and GST-RhoB. Western blots were probed with an anti-RhoB antibody to detect mono- and poly-ubiquitinated RhoB.

Given the utility of the UbVs for probing HECT E3 functions in vitro, and the parallel effects of UbV NL.1 on increasing Ub chain formation in mammalian cells (FIG. 4J), we examined effects in cells upon expressing UbVs targeting a select panel of HECT E3s (HACE1, HUWE1, WWP2, and NEDD4L). In all cases, expression of UbVs increased or attenuated ubiquitination levels in accordance with their in vitro properties (Inoue et al., 2013; Maddika et al., 2011; Torrino et al., 2011). For instance, inhibitors of HACE1 or HUWE1 significantly decreased ubiquitination of the HACE1 target Rac1 (FIG. 12A) or stabilized the protein levels of HUWE1 and its substrate c-Myc, respectively (FIG. 12B). Furthermore, activators of WWP2 increased autoubiquitination and degradation of WWP2 and its substrate PTEN (FIG. 12C-D).

Figure 6:
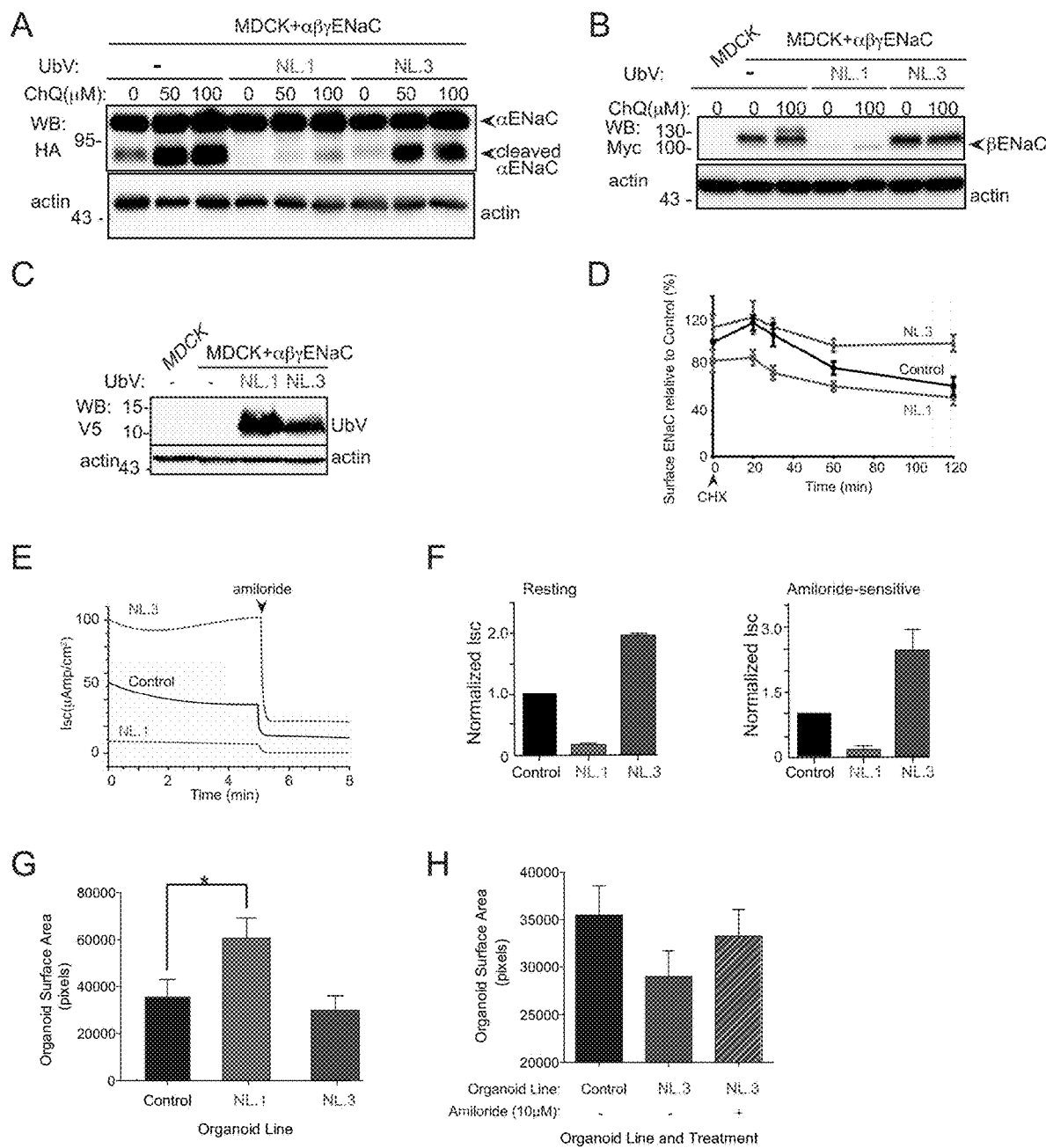
FIG. 6. UbVs modulate NEDD4L functions in cells and intestinal organoids (mini-guts). (A-C) Western blot analysis of protein levels of HA-tagged αENaC (A) and Myc-tagged βENaC (B) (in MDCK cells stably expressing $α_{3xHA}$, $β_{myc,T7}$ and $γ_{FLAG}$-ENaC) with NEDD4L UbV (C) NL.1 or NL.3 (or no UbV) in cells treated (or not) with the indicated concentrations of the lysosomal inhibitor chloroquine (ChQ). Actin blots are shown as loading control. Reduced levels of cleaved αENaC (the active form of αENaC) and βENaC were observed with the expression of NL.1 but not NL.3. (D) Cell surface levels of ENaC analyzed by ELISA in the above tagged αβγENaC-MDCK cells co-expressing (or not) NL.1 or NL.3. Cycloheximide (CHX, 44.4 μM) was added at time zero to inhibit protein synthesis. Cell surface ENaC was analyzed with anti-HA antibody to detect αENaC. Values are mean±SEM (N=4). (E) ENaC function (Isc) analyzed in Ussing chambers in the above MDCK cells stably expressing tagged αβγENaC alone or together with NL.1 or NL.3. The traces from one representative experiment (arrow: apical addition of the ENaC inhibitor amiloride, 10 μM) are shown. (F) Summary of 3 separate experiments (mean±SEM) of resting Isc or amiloride-sensitive Isc as described in (E). (G-H) Quantification of surface area (in pixels) of control intestinal (distal colon) organoids (GFP-transduced) or organoids expression ubiquitin variant (NL.1 or NL.3), 7 days after seeding. Histogram bars represent mean±SEM. N=30-40 organoids per condition. Pixel count to surface area ratio is 1 pixel to 0.78 μm². In (G), Statistical analysis demonstrated a significant difference in surface area between the control and NL.1-expressing organoids (t-test, p<0.05). In (H), NL.3-expressed organoids were incubated with or without amiloride (10 μM) for 30 min followed by analysis of surface area by microscopy. See also FIG. 13.

We also evaluated the effects of UbVs targeting NEDD4L on regulation of its best-characterized substrate, the Epithelial $Na^+$ Channel, ENaC (SCNN1) (Kamynina et al., 2001; Kimura et al., 2011). Kidney-derived epithelial MDCK cells stably expressing αβγENaC and activator NL.1 or inhibitor NL.3 (FIG. 6A-C) were tested for ENaC cell surface stability and function. Our results show reduced stability and cell-surface expression of ENaC by NL.1, but not NL.3 (FIGS. 6A, B, and D), and accordingly, reduced or enhanced ENaC function (amiloride-sensitive $Na^+$ channel activity, Isc) by NL.1 or NL.3, respectively (FIG. 6E-F). Taken together, these results show that UbVs activate or inhibit HECT E3s in cells in a manner consistent with their in vitro activities.

The ability to modulate NEDD4L activity is of particular interest, because elevated cell surface expression of ENaC and NCC ($Na^+$-$Cl^-$ Co-transporter, another NEDD4L substrate) in the distal nephron causes increased $Na^+$ reabsorption and salt-induced hypertension (Ronzaud et al., 2013). Indeed, mutations in the PY motifs of ENaC, which prevent proper NEDD4L binding to and suppression of this channel, cause Liddle syndrome, a hereditary hypertension (Lifton et al., 2001). Likewise, renal tubular deficiency of NEDD4L causes salt-induced hypertension by elevated NCC and ENaC abundance and function (Ronzaud et al., 2013). The increased NCC function and hypertension partially resembles Pseudohypoaldosteronism II (PHA II), another genetic hypertension caused by elevated NCC function due to mutations in its regulators, the WNK kinases (Wilson et al., 2001). Moreover, NEDD4L targets ENaC in lung epithelia, and NEDD4L depletion there causes massive inflammation and airway mucus plugging, resembling lung disease in cystic fibrosis patients (Kimura et al., 2011).

Thus, our identification of UbV activators of NEDD4L function could point to a novel therapeutic avenue for the treatment of hypertension and inflammation. This would require a proof that UbVs can function in mammalian tissues, not just in isolated cells. To this end, we utilized the recently developed technology to grow three-dimensional intestinal epithelial organoids (mini-guts) from intestinal stem cells (Sato and Clevers, 2013) and grew mouse distal colon organoids; the distal colon strongly expresses both ENaC and NEDD4L ((Duc et al., 1994) and Jiang & Rotin, unpublished). Consistent with inhibition of ENaC function observed in MDCK cells, lentiviral transduction of NL.1 caused organoid luminal swelling due to reduced fluid reabsorption into the media, while expression of NL.3 had the opposite effect (FIG. 6G). The effect of UbVs on the organoid luminal volume change is likely mediated by NEDD4L regulating ENaC (which is expressed in these organoids, FIG. 12E), as treatment of NL.3 ubiquitin variant-transduced organoids with the ENaC inhibitor amiloride prevents the reduction in organoid surface area (FIG. 6H). In conclusion, these data suggested that activation of NEDD4L by targeting of the N-lobe exosite could be a means for treatment of hypertension and inflammation.

Lentiviral UbV Genetic Screen Identifies Novel Functions of HECT E3s

Figure 7:
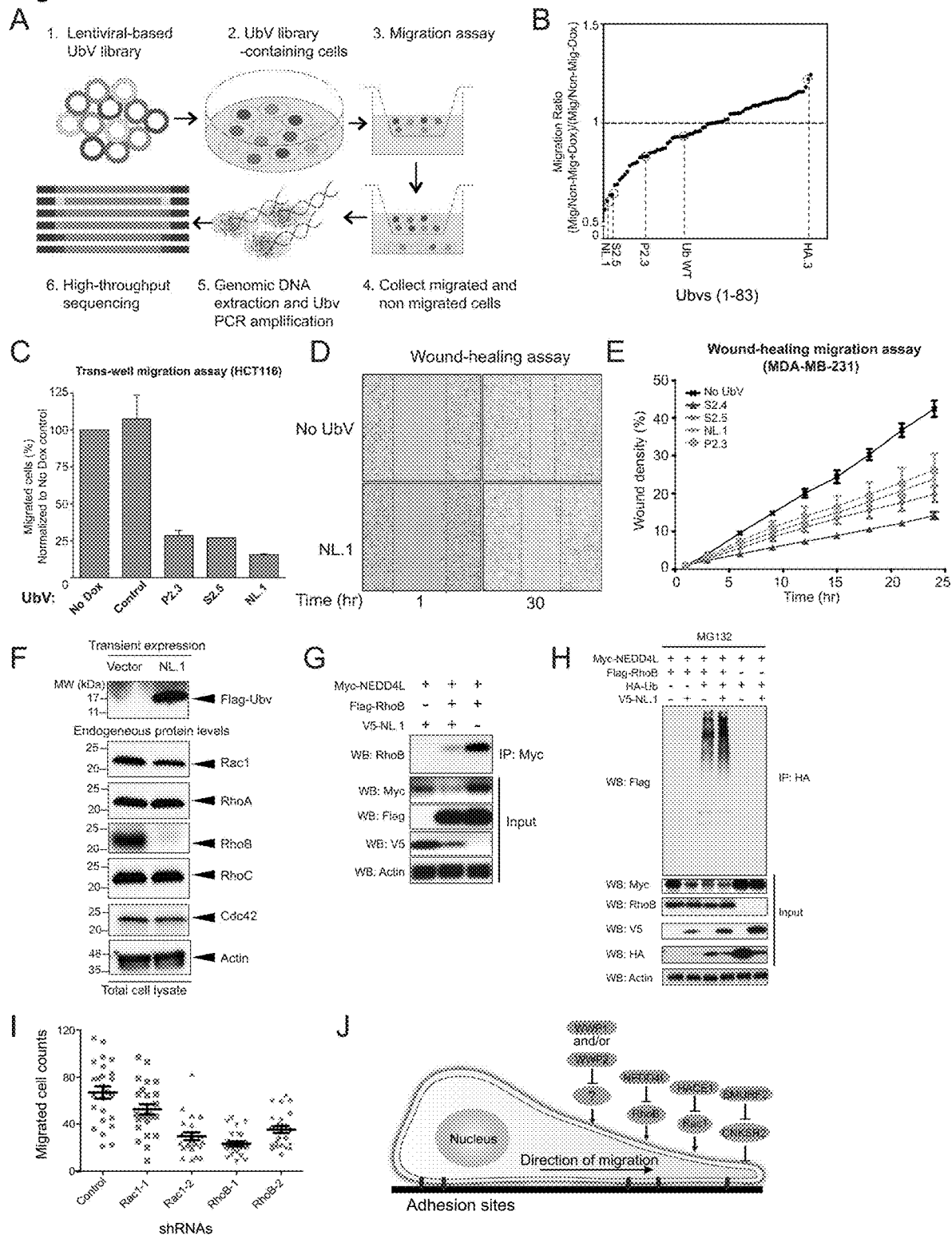
FIG. 7. UbVs reveal new functions of HECT E3s in cell migration. (A) Schematic representation of the HECT UbV lentiviral library screens for the identification of UbVs affecting cell migration (see Experimental Procedures for details). (B) Ranking by migration ratio of 83 UbVs from two independent pooled UbV lentivirus screens examining cell migration in HCT116 cells using a trans-well assay. UbVs discussed in the text are circled. (C) Quantitation of migrated HCT116 cells (%) stably expressing control Ub and indicated UbVs using the trans-well assay. The data were presented as the mean±SEM (N=3) normalized to non-Dox treatment control. (D-E) Wound healing assay was performed to examine the effect of indicated UbVs on cell migration efficiency. Representative photos of scratch wound closure with and without expression of NL.1 are shown in (D). (E) Quantitation of relative wound density closure after scratch in MDA-MB-231 cells stably expressing indicated UbVs (no UbV as control). The data are presented as the mean±SEM (N=3). (F) Expression of NL.1 destabilizes RhoB. Whole-cell extracts from HCT116 cells with transient expression of vector or FLAG-tagged NL.1 were subjected to western blotting using the indicated antibodies. (G-H) NEDD4L immunoprecipitated (G) and ubiquitinated RhoB in cells (H). NL.1 stimulated the activity of NEDD4L (H). HCT116 cells were transfected with constructs encoding HA-Ub, Myc-NEDD4L, FLAG-RhoB, and UbV NL.1. Whole cell lysates were subjected to immunoprecipitation (IP) with Myc (G) or FLAG (H) antibody and followed by western blotting using the indicated antibodies. Cell lysates were also immunoblotted with the indicated antibodies to monitor expression levels. (I) RhoB is required for cell migration of HCT116 cells. Quantitation of migrated HCT116 cells expressing control shRNA or two different shRNAs targeting Rac1 or RhoB. Scatter blots of mean migrate cell counts from 3 independent experiments were shown. (J) Schematic illustration of the roles of HECT E3 ligases in regulation of cell migration. UbV inhibitors confirmed that SMURF2 promotes and HACE1 inhibits cell migration, presumably through ubiquitination of CNKSR2 or Rac1, respectively. In addition, UbV activators revealed that NEDD4L inhibits cell migration by ubiquitination of RhoB and activation of WWP1 and/or WWP2 also leads to decreased cell migration. See also FIG. 13.
Figure 8:
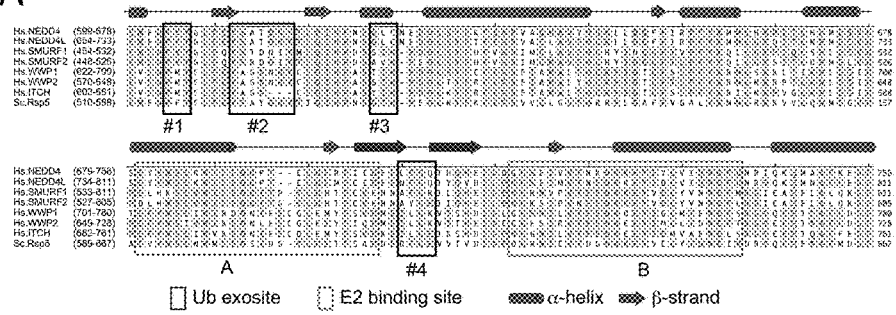
FIG. 8. Molecular details of UbV-HECT E3 interactions. (A) Sequence alignment (ClustalW, Lasergene) for closely-related NEDD4-family members showing the E2-binding region and N-lobe exosite. Secondary structures are indicated above based on NEDD4L (PDB: 2ONI, 3JW0) and Rsp5 (PDB: 3OLM, 4LCD). β-strands in dark red vary among HECT structures. (B) To define which portions of HECT domains are shown in (D) and FIG. 9, regions of HECT domain interacting with E2s (labeled A and B), and the Ub/UbV-binding N-lobe exosite (numbered 1-4) are highlighted on the crystal structure of WWP1 HECT domain in complex with the E2 UBCH7 and UbV P2.3. (C) Three orientations showing details of HECT domain interactions with inhibitory UbVs or E2s. (D) Close-up views of HECT domain interactions with inhibitory UbVs (WWP1-UbV P1.1 and ITCH-UbV IT.2) or E2s (WWP1- or E6AP-UBCH7), with coloring of the proteins as labeled above panels. Structures were aligned over the interaction region of the HECT domain and represented with MacPyMOL (Schrodinger). (E). Competition assay of NEDD4L, UBCH5B~Ub (oxyester linked) and UbV NL.3. Individual and mixed complexes are loaded in native gel. UbV NL.3 disrupt the interactions between NEDD4L and UBCH5B~Ub.
Figure 8:
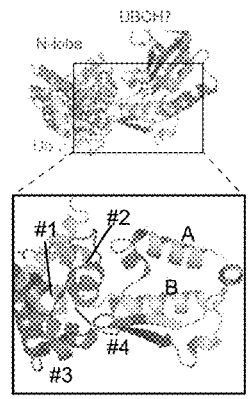
Figure 8:
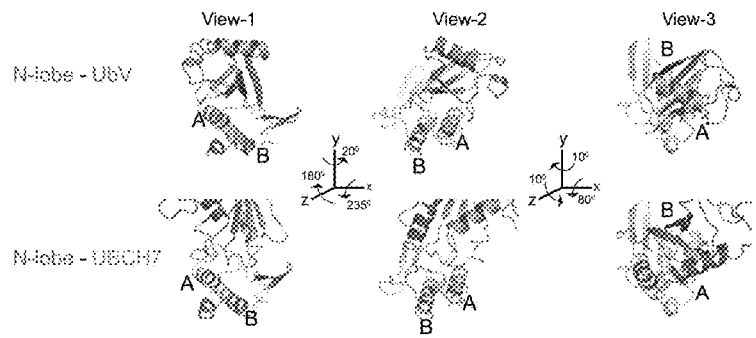
Figure 8:
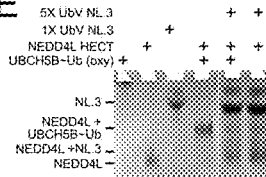
Figure 8:
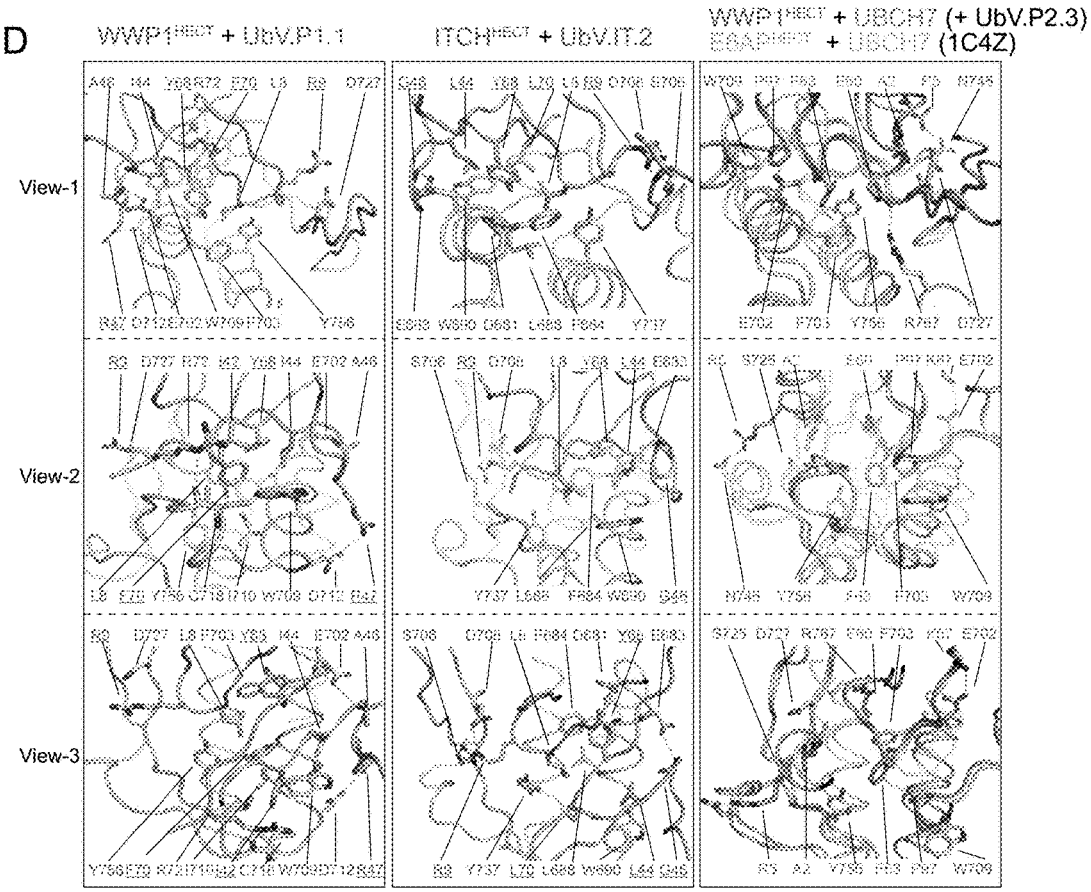

To test whether UbVs can be used in a screen to discover unknown biological functions of HECT E3s in an unbiased and high throughput manner, we used our UbV panel to globally interrogate the family for roles in cell migration, a pathway known to involve ubiquitination and that is central to embryonic development and plays a major role in cancer invasion and metastasis (Deng and Huang, 2014; Simpson et al., 2008). While SMURF2 and HACE1 have been implicated in cell migration by RNA interference (Castillo-Lluva et al., 2013; David et al., 2014; Jin et al., 2009), we wondered whether our unprecedented ability to activate (or block) enzyme activity with UbVs could both score these positive controls and also potentially reveal roles for other HECT E3s not known previously as regulators of this pathway. To this end, we transduced HCT116 human colon cancer carcinoma cells with a pool of 83 distinct lentiviruses, each containing an inducible defined UbV expression cassette targeting one of 19 HECT E3s or one of 13 other proteins, and analyzed the migratory response in a trans-well migration assay by deep sequencing (FIG. 7A-B). Selected modulatory UbVs were further validated individually using two different cell migration assays (FIGS. 7C-E).

Upon induction of UbV expression by doxycycline and as expected based on RNA interference experiments (Castillo-Lluva et al., 2013; Jin et al., 2009), our screen identified inhibitors of HACE1 (HA.3) and SMURF2 (S2.5) that increased or decreased cell migration, respectively (FIG. 7B). In addition, we found that two activators (P2.3 and NL.1) caused striking decreases in cell migration. UbV P2.3 binds to both WWP1 and WWP2 (Table 5), and its effect is thus likely due to the combined activation of these two enzymes. UbV NL.1 potently and specifically activates NEDD4L, which has not previously been implicated in cell migration. To identify putative NEDD4L substrates, we assayed effects of UbV NL.1 transient expression on protein levels of small GTPases, which are key regulators of cell migration (Alfano et al., 2012; Torrino et al., 2011; Wang et al., 2003; Wang et al., 2014). Notably, we observed decreased abundance of endogenous RhoB protein following transient or inducible expression of NL.1 (FIGS. 7F and 12F), suggesting that RhoB could be an ubiquitination substrate of NEDD4L. Consistent with this, we observed that NEDD4L interacts with RhoB in a co-immunoprecipitation (IP) experiment (FIG. 7G). Moreover, NEDD4L was able to ubiquitinate RhoB in cells (FIG. 7H) and in vitro (FIG. 12G), a process that was enhanced by NL.1. We further confirmed that in HCT116 cells, the depletion of RhoB decreased cell migration to the same level as Rac1 knockdown (FIG. 7I). Although the function of RhoB in cell migration is not entirely understood, our observations are consistent with a report showing that depletion of RhoB can significantly reduce migration and invasion of prostate carcinoma cells (Alfano et al., 2012). Based on our observations, RhoB is likely the functional substrate of NEDD4L in regulating cell migration and access to both inhibitors and activators of HECT E3s enhanced our view of how these enzymes work to regulate cell migration (FIG. 7J). The results imply that activation of NEDD4L through binding to the N-lobe exosite could be exploited as a novel means for inhibition of metastatic phenotypes.

Experimental Procedures

Protein Expression and Purification

All DNA constructs used to produce proteins for UbV selections and subsequent assays were listed in Table 7. The following proteins were subjected to UbV selections: HECT domains of human ITCH, NEDD4, NEDD4L, SMURF1, SMURF2, WWP2, HECW1, HECW2, HERC1, HERC2, HERC4, HERC6, HACE1, HUWE1, UBE3A, UBE3C, EDD1, KIAA0317, HECTD1 (His- and Avi-tagged for in vivo biotinylation (Kay et al., 2009), pET28 vector, domain boundary shown in Table 7), full length human WWP1 and yeast Rsp5 (GST tagged). PCR amplified DNA fragments encoding the indicated UbVs with an N-terminal FLAG epitope tag were cloned into Gateway Entry vector pDONR221 (Thermo Scientific) according to the manufacturer's instructions and then transferred into Gateway Destination expression vector pET53 (His-tagged, Thermo Scientific). The above-mentioned plasmids were used to transform *Escherichia coli* BL21 (DE3) for protein expression. Protein expression was induced by addition of IPTG (isopropyl β-D-1-thiogalactopyranoside, Bioshop) at mid-log phase to a final concentration of 1 mM. After incubation overnight at 16° C. with shaking, cell pellets were collected by centrifugation (12,200×g, 10 min) and lysed, and proteins were purified using Ni-NTA Agarose (Qiagen 30250) at 4° C. following the manufacturer's instructions. The purity of eluted fractions was determined by polyacrylamide gel electrophoresis. Protein concentrations were determined by measuring the absorption at 280 nm (Nanodrop 1000, Thermo Scientific). Eluted proteins were dialyzed into 50 mM HEPES buffer pH 7.5, 250 mM NaCl, 5% glycerol, 1 mM DTT and stored at 4° C. or frozen at −80° C. for further applications.

Protein constructs used in biochemical assays, Octet bio-layer interferometry and crystallization are listed in Table 7. All constructs were made using standard molecular cloning methods or QuickChange mutagenesis. All proteins were expressed in BL21 (DE3) Codon Plus (RIL) *Escherichia coli* and purified using GST-affinity or nickel-affinity chromatography depending on the expression tags. Protein tags including GST, MBP, and SUMO2 were released by TEV or SEN P2 protease. After proteolysis treatment, subsequent purifications including dialysis, ionic exchange and size exclusion chromatography were applied to obtain pure fractions of target proteins. Proteins were in final buffer containing 25 mM Tris pH 7.6, 200 mM NaCl and 3 mM DTT. Tag-free ubiquitin were purified by acidic precipitation followed by ionic exchange and size exclusion in 25 mM HEPES pH 7.0, 200 mM NaCl and 3 mM DTT. Pure proteins were concentrated, aliquoted, flash-frozen by liquid nitrogen and stored at −80° C.

To crosslink fluorescent probe on His-1CysUb, WBP2 or S-WBP2-1K, proteins were first treated with 10 mM DTT for 30 minutes, then desalted in 25 mM HEPES pH7.0 and 150 mM NaCl by Zeba spin columns or PD-10 columns. 10-fold molar excess maleimide-linked fluorescein (AnaSpec) dissolved in DMSO was mixed with His-1CysUb or WBP2 at 4° C. for 1 hour. Unused fluorescein cross-linker was quenched by 50 mM DTT. Reductive lysine methylation on ubiquitin was carried out by mixing proteins with DMAB (dimethylamine borane complex) and formaldehyde at 4° C. overnight. Excess DMAB and formaldehyde were quenched by 50 mM Tris pH 8.0. Both fluorescein-labeled proteins and methylated proteins were purified by thorough desalting procedures and size exclusion to remove unused chemicals and precipitated proteins.

Ubiquitin Variant (UbV) Selection

The phage displayed UbV library used in this study was re-amplified from Library 2 as described (Ernst et al., 2013). Protein immobilization and UbV binding selections were performed according to established protocols (Tonikian et al., 2007). Purified HECT E3 ligases were coated on 96-well MaxiSorp plates (Thermo Scientific 12565135) by adding 100 μL of 1 μM proteins and incubating overnight at 4° C. Five rounds of selections using the phage-displayed UbV library were performed against immobilized proteins. As seen in FIG. 1D, (I) Each phage particle in the library pool displays a unique UbV and encapsulates the encoding DNA. (II) Binding phages are captured with an immobilized HECT domain protein. (III) Non-binding phages are washed away. (IV) Bound phage are amplified by infection of *Escherichia coli*. The enriched phage pool is cycled through additional rounds of selection to further enrich for HECT-binding UbVs. After the fifth round, binding UbV-phage clones were identified by clonal phage ELISAs and subjected to DNA sequencing to decode the UbV sequences (Tonikian et al., 2007).

ELISA Assays to Evaluate Binding and Specificity

Proteins in study were immobilized on 384-well MaxiSorp plates (Thermo Scientific 12665347) by adding 30 μL of 1 μM proteins for overnight incubation at 4° C. Phage and protein ELISA against immobilized proteins was performed as described (Ernst et al., 2013). Binding of phage was detected using anti-M13-HRP antibody (GE Healthcare 27942101) and binding of FLAG-tagged UbVs was detected using anti-FLAG-HRP antibody (Sigma-Aldrich A8592). To measure the half maximal binding concentration ($EC_{50}$) of UbVs binding to HECT E3 ligases, the concentration of UbVs or wild type Ub was varied from 0 to 4 μM (24 points, 1:2 dilution), while the concentration of target proteins immobilized on the plate remained at 1 μM. $EC_{50}$ values were calculated using the GraphPad Prism software with the built-in equation formula (non-linear regression curve).

Bio-layer Interferometry (BLI)

Concentrated analyte and ligand proteins were diluted into BLI reaction buffer (25 mM HEPES pH 7.0, 150 mM NaCl, 0.1 mg/ml bovine serum albumin, 0.01% Tween20). BLI experiments were performed on an Octet RED96 system (ForteBio) using anti-GST antibody biosensors for GST-tagged ligands (HECT domains) and His-tagged analytes or native WT ubiquitin at 25° C. 7-9 dilution points of analytes covering a wide concentration range were applied. Sensorgram raw data was processed and extracted by Octet Analysis 9.0 software. Dissociation constants ($K_D$) were obtained by fitting the response wavelength shifts in the steady-state regions using single-site binding system (Eq. 1) or nonequivalent two-site binding system (Eq. 2) shown below.

$$R_{eq} = R_{max} \frac{[C]}{K_D + [C]} \quad (1)$$

$$R_{eq} = R_{max} \frac{2[C]^2 + K_{D2}[C]}{[C]^2 + K_{D1}K_{D2} + K_{D2}[C]} \quad (2)$$

where $R_{eq}$ is value of steady-state response shift in each sensorgram curve, [C] is the titrant concentration, $R_{max}$ is the maximal response in the steady-state region, $K_D$ is the binding constant for single-site binding system and $K_{D1}$ and $K_{D2}$ are two binding constants of nonequivalent two-site binding system. In both equations, $R_{max}$ and $K_D$ values are unknown and Levenberg-Marquardt algorithm was used to perform iterative non-linear least squares curve fitting in Profit 6.2 (QuantumSoft) to obtain the fitted $R_{max}$ and $K_D$.

Protein Crystallization and Data Collection

Six HECT E3-UbV complexes were crystallized: NEDD4L$^{HECT}$-UbV NL.1, WWP1$^{HECT}$-UbV P2.3-UBCH7, WWP1$^{HECT}$-UbV P1.1, Rsp5$^{HECT}$-UbV R5.4, ITCH$^{HECT}$-UbV IT.2, and NEDD4$^{HECT}$-UbV N4.4. Crystallization conditions and data analysis details are described below.

NEDD4L$^{HECT}$-UbV NL.1

NEDD4L$^{HECT}$-NL.1 complex was prepared by 2-step GST and Ni-NTA affinity co-pulled down followed by TEV proteolysis, dialysis, ionic exchange and size exclusion. Proteins were concentrated to 22-26 mg/ml in 25 mM HEPES pH 7.0, 150 mM NaCl and 5 mM DTT. Crystals grew at 4° C. in 1:1 volumetric ratio of protein and reservoir buffer (0.1 M sodium cacodylate pH 6.0, 0.18 M NaCl, 5-6% polyethylene glycol (PEG) 8000, 0.7% 1-butanol) by the hanging-drop vapor diffusion method and were improved by streak seeding. Crystals were cryoprotected in reservoir solution supplemented with 35% glycerol.

WWP1$^{HECT}$-UbV P2.3-UBCH7

GST-TEV-WWP1$^{HECT}$ Δ5 (C-terminal 5 residues removed), GST-TEV-P2.3 UbV and SUMO-GG-UBCH7-His$_6$ were purified separately by affinity (GST for WWP1 and P2.3 or Ni-NTA for UBCH7), protease digestion (TEV for WWP1 and P2.3 or SENP2 protease for UBCH7), ionic exchange and size exclusion. WWP1$^{HECT}$-P2.3-UBCH7 complex was created by directly mixing WWP1$^{HECT}$ Δ5, P2.3 and UBCH7 at 1:1.5:1.5 molar ratio, respectively and was concentrated to 8-10 mg/ml for crystallization. Crystals grew by hanging-drop vapor diffusion method at 23° C. and quality was improved by streak-seeding in 0.1 M sodium citrate pH 5.2, 10% isopropanol, 8% PEG 3350. Cryoprotectant supplemented with 8% xylitol, 8% glycerol and 8% ethylene glycol in reservoir solution was used.

WWP1$^{HECT}$-UbV P1.1

GST-TEV-P1.1 UbV was purified by GST-affinity, TEV protease digestion and size exclusion. 10 mg/ml complex of WWP1$^{HECT}$-P1.1 was made by mixing 1:2 molar ratio of WWP1$^{HECT}$ Δ5 and P1.1, respectively. Crystals of WWP1$^{HECT}$-P1.1 were grew at both 4° C. and 23° C. by hanging-drop vapor diffusion method and quality was improved by streak-seeding in 0.17 M ammonium sulfate, 25% glycerol and 25% PEG 3350 at 23° C. Reservoir solution was used as cryoprotectant for crystals.

Rsp5$^{HECT}$-UbV R5.4

Expressed GST-TEV-Rsp5$^{HECT}$ and His-R5.4 UbV are co-pulled down by GST and Ni-NTA affinity sequentially. GST tag was removed by TEV protease digestion. The complex was purified by sized exclusion (buffer: 25 mM HEPES, 150 mM NaCl and 2 mM DTT) and concentrated to 12.5 mg/ml. Crystal of Rsp5$^{HECT}$-R5.4 complex grew at 23° C. in 1:1 volumetric ratio of protein and reservoir buffer (0.1 M Bis-Tris, pH 5.5, 0.2-0.25 M ammonium acetate, 14% PEG 3350) by the hanging-drop vapor diffusion method. Crystals were cryoprotected in reservoir solution supplemented with 8% xylitol, 8% glycerol and 8% ethylene glycol.

ITCH$^{HECT}$-UbV IT.2

His-TEV-ITCH$^{HECT}$ and His-IT.2 were expressed in BL21 (DE3) strain and separately pulled down from cobalt-affinity column. TEV-cleaved ITCH$^{HECT}$ and His-IT.2 were further purified by ionic Q column. 1:2 molar ratio of ITCH$^{HECT}$ and IT.2 were mixed to reach 17 mg/ml for crystallization screening. Crystals were grown in 1.6 M ammonium sulfate, 0.2 M sodium acetate, 0.1 M HEPES pH 7.5, 5% ethylene glycol in hanging drop setup at 20° C. Solution containing well solution and 20% glycerol was used as cryoprotectant for crystals.

NEDD4$^{HECT}$-UbV N4.4

NEDD4$^{HECT}$ and His-N4.4 were expressed and purified with the purification protocols for ITCH$^{HECT}$-IT.2 complex. NEDD4$^{HECT}$-N4.4 complex was prepared by mixing 2-fold His-N4.4 to NEDD4$^{HECT}$. The final concentration is 15 mg/ml. The protein sample was mixed with Trypsin at a 1:1000 (W/W) Trypsin:protein ratio before setting up crystallization. Crystals were grown in 20% PEG 8000, 10% glycerol, 0.1 M HEPES pH 7.0 in hanging drop setup at 20° C. 20% glycerol with reservoir solution is used as cryoprotectant for crystals.

Diffraction data were processed with HKL2000 (Otwinowski and Minor, 1997) for NEDD4L$^{HECT}$-NL.1, HKL3000 (Otwinowski and Minor, 1997) for ITCH$^{HECT}$-IT.2, and NEDD4$^{HECT}$-N4.4 and RAPD (rapd.nec.aps.anl.gov/rapd) for Rsp5$^{HECT}$-R5.4, WWP1$^{HECT}$-P2.3-UBCH7 and WWP1$^{HECT}$-P1.1. All structures except of ITCH$^{HECT}$-IT.2 were determined by molecular replacement using Phaser (McCoy et al., 2007) with NEDD4L (PDB: 2ONI), WWP1 (PDB: 1 ND7), NEDD4 (PDB: 2XBB) or UBCH7 (PDB: 4Q5E) as search models. For ITCH$^{HECT}$-IT.2, phasing was solved by molecular replacement using the CCP4 suite programs BALBES and MOLREP with previous ITCH$^{HECT}$ structure (PDB: 3TUG) as the search model. In the crystal structure, two UbV IT.2 were crystallized with one ITCH-$^{HECT}$. The UbV IT.2 bound to N-lobe exosite is proposed formed by crystal packing. Model constructions and rebuildings were performed in Coot (Emsley et al., 2010) and refined by Phenix (Adams et al., 2010) or REFMAC5 (Murshudov et al., 1997) in CCP4 suite (Winn et al., 2011). MolProbity (Chen et al., 2010) was used to evaluate qualities of all crystal structures. Molecular interactions in the HECT-UbV structures were analyzed by NACCESS (Hubbard, 1993), PDB ePISA (Krissinel and Henrick, 2007) and MacPyMOL (Schrödinger).

Biochemical Assays

Pulse-chase Ubiquitination Assays

The biochemical assays were performed and monitored using either fluorescently labeled ubiquitin (Ub*, * stands for fluorescein probe) or substrates (WBP2* or S-WBP2-1K*). In all UbV-treated assays, 10-fold molar ratio of UbV/E3 was used to saturate HECT E3 with UbV during the entire reaction time. All reacted samples were quenched by mixing with SDS sample loading buffer, separated by SDS-PAGE and analyzed based on fluorescent signals of Ub*, WBP2* or S-WBP2-1K*. A Typhoon FLA9500 Phosphoimager (GE Healthcare) was used to scan fluorescent gel images.

Assays Detected by Fluorescence Signals

To monitor Ub* transferred from E2 to E3 (E2-to-E3), di-ubiquitin chain synthesis (Ub~Ub*) or substrate (WBP2, Sna3 and Sna4) ubiquitination, pulse-chase assay was applied with 2 steps. First, 20 μM E2 (UBCH5B or UBCH7) was mixed with 500 nM E1 in reaction solution (25 mM HEPES pH 7.5, 200 mM NaCl, 10 mM MgCl$_2$, 2 mM ATP and 0.04 mg/ml bovine serum albumin) at room temperature for 30 minutes to generate charged E2 (E2~Ub*). Then E1 activity was quenched by 25 mM HEPES pH 7.0, 100 mM NaCl and 50 mM EDTA. Second, E2-to-E3, Ub~Ub* or substrate~Ub reactions ran on ice were initiated by loading E2~Ub* to solution containing varied E3, E3, and free ubiquitin or substrate, respectively. 100 mM DTT in SDS sample loading buffer was used to check the formation of thioester bonded E3~Ub* intermediate in pulse-chase reactions. Details of each biochemical assay shown in this study are described here. For E2-to-E3 pulse chase assays with inhibitor UbVs in FIG. 2D, 1 µM UBCH7~Ub*, 3 µM E3 and/or 50 µM UbVs were mixed on ice for 1 minutes to see Ub transferred from E2 to E3. To monitor the E3 concentration-dependent E2-to-E3 Ub transfer in FIGS. 10B and 10C, 1.6 µM UBCH5B~Ub* and 0.5~30 µM E3 were mixed on ice with or without UbV to monitor Ub transfer efficiency. To test the Ub transfer efficiency by varied truncated E3 in FIG. 12B-D, 2 µM E3 and 2 µM UBCH7~Ub* were mixed with or without excess UbVs on ice. 6 Rsp5 UbVs (2.7 µM) were tested for E2-to-E3 assays with 2.7 µM Rsp5FL and 0.4 µM UBCH5B~Ub*. Ub~Ub* synthesis assays in FIG. 3C-E were done by 1.2 µM of UBCH7~Ub*, 2 µM of E3 (saturated with and without UbV NLI1, NL.2 or P2.3) and 100 µM of free Ub on ice. WBP2 ubiquitination (WBP2~Ub) was performed on ice by mixing 1.2 µM UBCH7~Ub*, 2 µM E3 (with and without UbV) and 2.9 µM WBP2.

Rapid-quench flow kinetic studies were carried out at 25° C. using the KinTek RQF-3 instrument as described previously (Kamadurai et al., 2013). 2 µM of UBCH5B~Ub was mixed with solution composed of 4 µM E3 (Rsp5$^{FL}$ or Rsp5$^{WW(proximal)\text{-}HECT}$), 2 µM UbV R5.4 and 30 µM Biotin-Sna3.

Autoubiqutination of Rsp5FL was carried out by mixing 50 nM E1, 200 nM UBCH7, 200 nM Rsp5$^{FL}$, 20 µM fluorescein-labeled ubiquitin and 2 µM UbVs (for control, buffer was loaded). The reactions ran room temperature for 15 minutes and were quenched by SDS sample buffer.

The encounter assays were carried out at room temperature by mixing two subset mixtures. The first subset has fluorescently labeled WBP2* or S-WBP2-1K*, E3 and free ubiquitin (or methylated ubiquitin) while the second subset contains E1 and charged UBCH7~Ub mixed with buffer or 30-fold WBP2 (30-fold to WBP2* or S-WBP2-1K*) for the multiple turnover and competition reactions, respectively. Both subsets were prepared in 25 mM HEPES pH 7.5, 200 mM NaCl, 2 mM ATP, 10 mM MgCl$_2$ and 0.04 mg/ml bovine serum albumin. The reactions were initiated by mixing the two subsets and quenched by SDS sample loading buffer at indicated reaction time points. To observe the chain elongation on S-WBP2-1K*, a prime reaction was performed to generate 30~40% portion of monoubiquinted or diubiquitinated S-WBP2-1K*. The reaction was then mixed with 30-fold WBP2 or buffer for single or multiple encounter reactions. The prime reaction ran in the same described buffer with 400 nM E3, 3 µM UBCH7~Ub, 80 nM E1 and 400 nM S-WBP2-1K*.

Competition Assay

Purified NEDD4L, oxyester-linked UBCH5B~Ub (Kamadurai et al., 2009) and UbV NL.3 were selected for the assays. 3 different mixed samples were prepared to evaluate competition. (A) 1:1 mixed NEDD4L and UBCH5B~Ub, (B) 1:5 mixed NEDD4L and UbV NL.3 and (C) 1:1:5 mixed NEDD4L, UBCH5B~Ub and UbV NL.3. In sample C NEDD4L and UBCH5B were mixed for 10 minutes on ice followed by addition of UbV NL.3. Samples were loaded in native gel (Bencsath et al., 2002).

Ubiquitination Assays with Immunoblotting

Biochemical reactions to study HECT E3 ligases autoubiquitination activity were performed in a volume of 25 µl in a buffer of 50 mM Tris pH 8.0, containing E1/UBE1 (50 nM, Boston Biochem E304), E2 as indicated (1 µM, kindly provided by Pankaj Garg), ubiquitin (20 µM, Boston Biochem U100H), HECT E3s as indicated (1 µM), and UbVs (10 µM). After incubation at room temperature for 60 min, reactions were stopped by the addition of 10 mM EDTA and SDS-PAGE sample buffer and resolved using 4-20% gradient gel (Bio-Rad 4561096). Mono- and poly-ubiquitinated HECT E3s were evaluated by western blotting. To assess the E3 activity of HACE1 on Rac1 GTPase in vivo, CHO cells (5×10$^6$) were transfected with 5 µg of HA-Rac1Q61L, 5 µg His6-ubiquitin, 2 µg myc-HACE1 and 1 or 5 µg of FLAG-UbV expression plasmids described in this study. Measurement of Rac1 ubiquitination was performed as described previously (Doye et al., 2012). Briefly, 24 h after transfection CHO cells were lysed in 1 ml of BU buffer (20 mM Tris-HCl, pH 7.5, 200 mM NaCl, 10 mM imidazole, 0.1% (v/v) Triton X-100, 8 M urea). Samples were homogenized, centrifuged 10 min at 10,000 g at room temperature. An aliquot of 50 µl was collected (Total protein input). In parallel, 0.1 ml of cobalt beads (Talon, Clontech) 50% slurry in BU buffer were added to each 0.9 ml assay supernatants and incubated at room temperature 1 hour on a rotating shaker. Beads were washed three times in BU and resuspended in one volume Laemmli blue buffer 2× followed by western blotting. The RhoB ubiquitination assay was performed as described (Wang et al., 2014). For in vivo assay, the whole cell lysates were subjected to anti-HA immunoprecipitation and followed by anti-FLAG western blotting to detect ubiquitinated FLAG-RhoB. For in vitro assay, GST-RhoB were purified using glutathione sepharose beads and added into a volume of 25 µl in a buffer of 50 mM Tris pH 8.0, containing E1/UBE1 (50 nM), E2/UBE2L3 (1 µM), ubiquitin (20 µM), HECT E3s as indicated (1 µM), and with and without NEDD4L UbV NL.1 (10 µM). MG-132 was used at 10 µM (Boston Biochem, 1-130).

DNA Constructs for Mammalian Cell Experiments

All DNA constructs used in the mammalian cell culture experiments were listed in Table 7. UbV was transferred to mammalian expression vectors either by Gateway methods or PCR sub-cloning. The WWP2 construct was obtained from the Human ORFeome collection (version 5.1), and ubiquitin construct was a gift from R. Baer (Columbia University, New York. USA). The WWP2 and UbV constructs were sub-cloned into pDONR vector and then into Myc-tagged or FLAG-tagged destination vectors using Gateway Technology (Invitrogen). The constructs pLVE-NL.1 and pLVE-NL.3 were cloned as follows: BamH1 site with N-terminal V5 tag containing the start code and SpeI site at the C-terminus with stop code were added to the UbV-WZ-12 (NL.1) and UbV-WZ-14 (NL.3) by PCR. After sequence verification, they were cloned into the lentiviral expression vector, pLVE (homemade by Rotin lab with IRES-EGFP, dual Zeocin resistance for bacterial and cell cultures). The expressions of the constructs were verified with western blot by transfecting the plasmids into 293T cells and blotted by V5 antibody. pXJ-HA-Rac1Q61L, pKH3-HACE1 and pRBG4-His6-ubiquitin (pCW7) were reported before (Torrino et al., 2011). Hace1 cDNA from pKH3-HACE1 was subcloned BamHI-EcoRI in pRK5-myc-HACE1. The Lentiviral Destination (pLD) Vector pLD-puro-TnZsGreen was constructed by replacing the versatile affinity (VA) tag from the pLD-puro-TnVA (Mak et al., 2010) with the green fluorescent protein ZsGreen using NheI/AgeI restriction sites. For shRNA-mediated gene silencing, sequences of the control and shRNAs targeting Rac1 and RhoB are available upon request. The vector pDEST-5'3x-FLAG-pcDNA5-FRT/TO was a gift from Dr. Anne-Claude Gingras and pLenti CMV rtTA3 Blast (w756-1) was a gift from Dr. Eric Campeau (Addgene plasmid #26429). The FLAG-RhoB and GST-RhoB expression vector was kindly provided Dr. Hong-Rui Wang.

Cell Culture and Transfection

Cells were cultured in DMEM (HEK293T and MDA-MB-231 cells) or McCoy's 5A (HCT116 cells) medium, supplemented with 10% fetal bovine serum (FBS), 100 U/ml of penicillin and 100 µg/ml of streptomycin. Chinese hamster ovary (CHO) epithelial cells were obtained from ATCC (CCL-61). Cells are grown in "DSG" medium, composed of DMEM/HAM-F12 (Life Technologies) supplemented with 10% (v/v) fetal bovine serum (EU Approved Origin, Invitrogen) and 50 µg/mL Gentamicin. The ENaC line, 409, established from MDCK (Madin Darby Canine Kidney) Cell, Type I, stably expressing 3 ENaC subunits, α, β and γ, was cultured in DMEM plus 10% FBS, 1× antibiotics and antimycotics, 600 µg/ml G418, 50 µg/ml hygromycin B and 2 µg/ml puromycin at various confluences for western blot, ELISA and Ussing chamber assays. All cell lines were maintained at 37° C. incubator with 5% $CO_2$. Lipofectamine 2000 (Life technologies) was used for transient transfection according to the manufacturer's instructions. For tet/dox inducible UbV expression cell lines (e.g. NL.1 and HU.1), FLAG-UbVs were inserted into Flp-In T-REx HCT116 cells using the Flp-in T-REx system according to the manufacturer's instructions (Life Technologies). Cells were selected with hygromycin (20 µg/ml) for 2 weeks.

Lentivirus Transduction

V5 N-terminally tagged UbVs (NL.1 and NL.3) were cloned in the lentiviral vector pLVE/Zeo and packaged into viruses. The viruses were transduced into MDCK cell line stably expressing tagged αβγENaC ($α_{3xHA}$; $β_{myc,T7}$; $γ_{FLAG}$-ENaC) (Lu et al., 2007) and selected with 100 µg/ml Zeocin (Life Technologies) to obtain individual clones. Survival clones were then expanded and tested for expression of V5-tagged UbVs. Clones with good expression of either NL.1 (clone 3) or NL.3 (clone 1) were used in subsequent assays. For UbV library-expressing cells, lentiviral ZsGreen-UbV clones were pooled at equimolar amounts and used for lentiviral packaging in HEK293T cells. HCT116 cells were transduced with the lentiviral pool at a low multiplicity of infection (M.O.I)<0.3. Transduced cells were selected with puromycin (1 µg/ml) for 7 days. For single UbV-expressing cell lines, lentiviral ZsGreen-UbV clones were individually used to infect HCT116 and MDA-MB-231 cells followed by puromycin selection (1 µg/ml) for 7 days.

Antibodies for Western Blotting and Immunoprecipitation (IP)

Western blotting and IP assays were performed according to standard protocols, as previously described (Ernst et al., 2013). Anti-Ub monoclonal antibody (clone FK2, Millipore 04-263, 1:3000) was used for auto-ubiquitination assays. For NEDD4L cellular assays, the following antibodies were used: anti-α ENaC (1:500) (Santa Cruz, sc-21012), anti-HA (Clone 16612, Biolegend, #901515, 1:10000); anti-FLAG (Clone OTI4C5, OriGene, TA50011-1, 1:10000); anti-Myc (Clone 4A6, EMD Millipore, 05-724, 1:2000); anti-V5 (AbD Serotec, MCA1360, 1:1000); and anti-β-actin (Sigma, A2228, 1:10,000). For WWP2 cellular assays, the following antibodies were used: anti-α-tubulin (Sigma-Aldrich, T6199, 1:5000), anti-HA (Sigma-Aldrich, H9658, 1:5000), and anti-FLAG (Sigma-Aldrich, F1804, 1:10000); anti-myc (Santa Cruz, sc-40, 1:5000); anti-PTEN (Santa Cruz, sc-7974, 1:1000). For HACE1 cellular assays, the following antibodies were used: anti-HA (Covance, clone 16612, 901501, 1:5000); anti-Myc (Santa Cruz, sc-40, 1:5000); and anti-FLAG (Sigma-Aldrich, F1804, 1:5000). For HUWE1 cellular assays, the following antibodies were used: anti-HUWE1 (Bethyl, A300-486A, 1:2000); anti-cMyc (Cell Signaling, 5605, 1:1000); anti-FLAG (Sigma-Aldrich, F1804, 1:10000); anti-actin (Sigma, A2228, 1:10,000). For cell migration assays, the following antibodies were used: Rho-GTPase Ab Sampler Kit (Cell Signaling, 9968S); anti-actin (Bethyl, A300-485A, 1:5000); anti-RhoB (Santa Cruz, sc-180, 1:1000); anti-V5 (Invitrogen, 1:5000); anti-myc (Santa Cruz, sc-40, 1:5000); anti-HA (Santa Cruz, sc-7392, 1:5000).

Poly-Ub Capture from Cell Extracts

HEK293 Flp-In T-REx (HFT) cells were grown in DMEM with 10% fetal bovine serum, 15 µg/ml Blasticidin and 100 µg/ml Zeocin. To generate HFT cells conditionally expressing UbV NL.1, the gene was cloned into pcDNA5-FRT/TO-FLAG-FRT-Hygromycin based vector and the plasmid transfected into HFT cells followed by selection with Hygromycin (100 µg/ml). To induce low UbV NL.1 expression, cells were treated with 0.5 µg/ml doxycycline (DOX) for the time indicated. At the indicated times, cells were washed twice with ice cold PBS and lysed in lysis buffer (50 mM Tris/HCl pH 7.5, 1 mM EDTA, 1 mM EGTA, 50 mM NaF, 5 mM sodium pyrophosphate, 10 mM sodium 2-glycerol 1-phosphate, 1 mM sodium orthovanadate, 1% (v/v) NP-40, 1 µg/ml aprotinin and leupeptin, 1 mM benzamidine, 1 mM AEBSF, 10 µM PYR-619 and 100 mM chloroacatemide), to produce whole-cell extracts. Whole cell extract derived ubiquitylated proteins were purified using Halo-4×UBA$^{UBQLN1}$ as described (Ordureau et al., 2014). Briefly, whole-cell extracts (0.5 mg) that were lysed in lysis buffer containing 100 mM chloroacetamide were incubated at 4° C. for 6 h with 40 µL of Halo-4×$^{UBQLN1}$ beads (pack volume). Following four washes with lysis buffer containing 0.5 M NaCl and four washes in 10 mM Tris (pH 8.0), proteins were released from Halo-4× UBA$^{UBQLN1}$ beads using 6 M guanidine HCL. Samples were subjected to reduction (10 mM TCEP) and alkylation (20 mM chloroacetamide) followed by TCA precipitation. Samples were digested overnight at 37° C. with Lys-C and trypsin [in 100 mM tetraethylammonium bromide, 0.1% Rapigest (Waters Corporation), 10% (vol/vol) acetonitrile (ACN)]. Digests were acidified with an equal volume of 5% (vol/vol) formic acid (FA) to a pH of ~2 for 30 min, dried down, resuspended in 5% (vol/vol) FA, and subjected to AQUA/PRM analysis as described below.

UB-AQUA/PRM Proteomics

UB-AQUA/PRM was performed largely as described previously but with several modifications (Ordureau et al., 2015a; Phu et al., 2011). A collection of heavy-labeled reference peptides each containing a single 13C/15N-labeled amino acid was produced at Cell Signaling Technologies and quantified by amino acid analysis. The 16 UB-AQUA reference peptides used for quantitation were previously listed in (Ordureau et al., 2014). UB-AQUA peptides from working stocks (in 5% FA) were diluted into the digested sample (in 5% FA) to be analyzed to an optimal final concentration predetermined for individual peptides.

Samples mixed to AQUA peptides were oxidized with 0.05% hydrogen peroxide for 30 min, subjected to C18 StageTip desalting, and re-suspended in 5% FA. Experiments were performed with three independent experimental samples and analyzed sequentially by mass spectrometry.

Our MS data were collected using a Q Exactive mass spectrometer (Thermo Fisher Scientific) as described in (Ordureau et al., 2015a) and peptides were separated using a 60 min gradient of 3%-25% acetonitrile in 0.125% FA with a flow rate of ~300 nl·min$^{-1}$. Raw files were searched and precursor and fragment ions quantified using Skyline version 3.1 (MacLean et al., 2010). Data generated from Skyline was exported into a Microsoft Excel spread sheet and Graph Pad Prism for further analysis as previously described (Ordureau et al., 2014). Total Ub amount was determined as the average of the total Ub calculated for each individual locus (Phu et al., 2011) with the loci common between Ub and UbV NL.1 excluded. Samples were normalized to total amount of Ub (1,000 fmol).

ENaC Stability and Functional Assays

To evaluate ENaC cell surface stability, MDCK cells stably expressing αβγENaC (Lu et al., 2007) together with NL.1 or NL.3 were seeded on 6-well plates and treated (or not) with 44.4 μM cycloheximide (CHX) at the indicated times. Cells were biotin-labeled with 0.5 mg/ml EZ-Link Sulfo-NHS-LC-Biotin (15 min, 4° C.), washed with PBS to remove unbound biotin, and lysed. Stability of surface ENaC was determined by quantifying αENaC, as described in further below, together with procedures for Ussing chamber analysis and Immunofluorescent (IF) confocal microscopy.

Stability of surface ENaC was determined by quantifying αENaC as follows. Briefly, 20 μg cell lysate was transferred to a 96-well ELISA plate (previously coated with anti-HA antibody (1:1000) and blocked with 0.5% BSA), incubated (4° C., 2 hr), plates washed (×3) with PBST (Phosphate Buffer Saline plus Tween 20) Strepavidin-HRP (1:1000) added (30 min, 4° C.) and washed (×5) with PBST. TMB substrate (eBioscience) was used for color development. Plates were read at 450 nm. All experiments were performed in duplicate and repeated 4 times. Data points were normalized to the αβγENaC-MDCK control (not expressing Ubvs and not treated with CHX), which was set to 100%. To assess ENaC protein stability assays, ENaC- plus Ubvs-expressing MDCK cell were seeded on 6 well plates in duplicates. 100 μM of chloroquine was added to one of duplicate wells overnight. Cells were lysed, quantified by the Bradford assay and analyzed by western blotting.

Ussing Chamber Analysis

The above ENaC- plus UbVs- expressing MDCK cell lines were grown on Millicell Cell Culture Inserts (Millpore) with 10 μM amiloride (added apically) for 6 days and induced with 1 μM dexamethasone and 2 mM sodium butyrate overnight to induced ENaC expression. After amiloride wash out, the closed circuit currents (Isc) were recorded in Ussing chambers (Physiological Instruments) and apical amiloride added at the end of the recording. The assays were repeated 3 times.

Immunofluorescent (IF) Confocal Microscopy

MDCK cells stably expressing αβγENaC and the NEDD4L UbVs were cultured on coverslips in 6-well plates. Wells were washed twice with ice-cold 1 ml PBS and incubated for 5 min with Alexa-Fluor-647-conjugated ConcanavalinA (1:1000) on ice to visualize the plasma membrane. The cells were fixed with cold 95% methanol for 20 min on ice before blocking with 1:100 NGS in 5% Skim Milk (1 hr). Slides were stained overnight at 4° C. with rabbit polyclonal anti-αENaC antibody (1:500, Santa Cruz, sc-21012) that recognizes the extracellular domain. After three PBS washes, cells were permeabilized with 0.1% Triton X-100 for 10 min and incubated with goat anti-rabbit Alexa 555 Fluor-conjugated secondary antibody and briefly stained with DAPI. Cover slips were mounted with Dako Cytomation. Images were acquired using a Quorum WAveFX-X1 spinning disc confocal system at 60× magnification with an Olympus S-Apo 60×/1.35 oil objective (Quorum Technologies Inc., Guelph, Canada).

Mouse colonic organoids from a C57BL/6 background were generated as described (Sato and Clevers, 2013). For viral infection, these organoids were isolated from the Matrigel matrix through pipetting, dissociated through incubation with Accutase, and then transduced with lentiviral particles containing either control or ubiquitin variant (NL.1 or NL.3) constructs for 8 hrs at 37° C. Transduced fragments were re-embedded in fresh Matrigel and allowed to recover with complete media. Positive transduction was confirmed by expression of a bi-cistronic GFP reporter. Supplementation of the growth media with zeocin (200 μg/mL) provided selection. Images were generated on a Leica DMI6000B epifluorescent microscope. Surface area measurements were calculated in ImageJ. For the amiloride rescue experiments, NL.3-variant organoids were incubated with or without amiloride (10 μM) for 30 min followed by analysis of surface area by microscopy. Wild-type GFP-transduced organoids were included as controls. Histogram bars represent mean±SEM. N=30-40 organoids per condition.

RT-PCR mRNA levels of the α, β, and γ subunits of ENaC are similar in both distal colonic organoids and tissue. mRNA was isolated from both distal colonic and ileal intestinal organoids and from distal colonic epithelial cell scrapings using TRIZol elution and spin-column purification. mRNA expression was evaluated by real-time PCR and normalized to GAPDH. Relative levels were calculated using ENaC subunit expression in distal colonic epithelial tissue as the baseline. Histogram bars represent mean±SEM.

TABLE 2

RT-PCR Primers

| | |
|---|---|
| α-ENaC | FWD-CTAATGATGCTGGACCACACC |
| | REV-AAAGCGTCTGCTCCGTGATGC |
| β-ENaC | FWD-GCCAGTGAAGAAGTACCTGC |
| | REV-CCTGGGTGGCACTGGTGAA |
| γ-ENaC | FWD-AAGAATCTGCCGGTTCGAGGC |
| | REV-TACCACTCCTGGATGGCATTG |
| GAPDH | FWD-CGTCTTCACCACCATGGAGA |
| | REV-CGGCCATCACGCCACAGTTT |

Trans-well Cell Migration Assay

5×10$^4$HCT116 cells expressing the UbV library or individual UbVs along with control cells were added on the upper chamber of cell-permeable inserts (Falcon #353182) placed into 12-well plates. Cells were maintained in FBS-free medium and treated with doxycycline (500 ng/mL) or vehicle and allowed to migrate for 48 h. 10% FBS-containing medium was used as the chemoattractant agent in the lower chamber. All experiments were performed in triplicate. For UbV library-expressing cells, migratory and non-migratory cells were harvested from the outer or inner membranes, respectively. Genomic DNA was extracted using the QIAmp Blood Maxi kit according to manufacturer's instructions (Qiagen) and prepared for Illumina sequencing as described in Supplemental Information. For single UbV-expressing cell lines, cells were stained using the Hemacolor stain kit according to the manufacturer's instructions (Harleco). Cells on the inner surface were swabbed out to remove non-migratory cells. Pictures of 5 different fields on the outer membrane were taken using a digital inverted microscope (EVOSfl-AMG) and migratory cells were counted.

Wound Healing Assay

UbV-expressing cell lines were seeded at $1\times10^4$ cells/well in a 96-well Essen ImageLock plate (Essen Bioscience). After 16 hours cells were treated with doxycycline (500 ng/mL) or vehicle and allowed to grow to confluence. A 96-pin WoundMaker (Essen Bioscience) was used to simultaneously create precise and reproducible wounds in all wells of the 96-well plate by gently removing the cells from the confluent monolayer. After washing, the plate was placed inside the IncuCyte (Essen Bioscience) incubator. The IncuCyte software was set to scan the plate every hour for 36 hours using the "Scratch Wound" option as the "Experiment Type." The data were analyzed by the "Relative Wound Density" program.

Illumina Sequencing and Data Analysis

Genomic DNA from migrated and non-migrated cells was precipitated using ethanol and sodium chloride, and resuspended in Buffer EB (10 mM Tris-HCl, pH 7.5). UbV sequences were amplified via PCR using primers harboring Illumina TruSeq adapters with i5 and i7 barcodes (primer sequences available upon request). PCR products were gel purified according to the manufacturer's instructions (Invitrogen). Purified PCR products were combined in equimolar amounts, and sequenced on an Illumina MiSeq sequencer. To analyze the sequencing data, paired-end reads ($2\times262$ bp) were processed using a bespoke Python pipeline as follows. First, reads were demultiplexed, allowing a single mismatch in each of the 8-base forward and reverse barcodes. Next, the UbV-encoding sequence was extracted from the reads using the barcode, Gateway AttB1, and FLAG sequences as landmarks to guard against frameshift mutations in the reads. Forward and reverse UbV sequences were aligned using the BioPython pairwise2.align.localms algorithm (options: match=1, mismatch=−10, gap_open_penalty=−20, gap_extend_penalty=−20, one_alignment_only), and sequences with an alignment score of at least 30 were retained. Unaligned reads or reads with gapped alignments were retained in a separate file for later inspection. Stand-alone BLAST (v. 2.2.18) was then used to match each spliced sequence to a FASTA file of UbV sequences (BLAST options: −p blastn −e 1e-100 −a 6 −m 7). The resulting XML file was parsed with a BioPython parser, and UbV sequences were counted and assembled into a matrix of m UbV sequences×n conditions.

REFERENCES

Adams, P. D., Afonine, P. V., Bunkoczi, G., Chen, V. B., Davis, I. W., Echols, N., Headd, J. J., Hung, L. W., Kapral, G. J., Grosse-Kunstleve, R. W., et al. (2010). PHENIX: a comprehensive Python-based system for macromolecular structure solution. Acta Crystallogr D Biol Crystallogr 66, 213-221.

Alfano, D., Ragno, P., Stoppelli, M. P., and Ridley, A. J. (2012). RhoB regulates uPAR signalling. Journal of cell science 125, 2369-2380.

Bencsath, K. P., Podgorski, M. S., Pagala, V. R., Slaughter, C. A., and Schulman, B. A. (2002). Identification of a multifunctional binding site on Ubc9p required for Smt3p conjugation. The Journal of biological chemistry 277, 47938-47945.

Cao, Y., Wang, C., Zhang, X., Xing, G., Lu, K., Gu, Y., He, F., and Zhang, L. (2014). Selective small molecule compounds increase BMP-2 responsiveness by inhibiting Smurf1-mediated Smad1/5 degradation. Scientific reports 4, 4965.

Castillo-Lluva, S., Tan, C. T., Daugaard, M., Sorensen, P. H., and Malliri, A. (2013). The tumour suppressor HACE1 controls cell migration by regulating Rac1 degradation. Oncogene 32, 1735-1742.

Chen, V. B., Arendall, W. B., 3rd, Headd, J. J., Keedy, D. A., Immormino, R. M., Kapral, G. J., Murray, L. W., Richardson, J. S., and Richardson, D. C. (2010). MolProbity: all-atom structure validation for macromolecular crystallography. Acta Crystallogr D Biol Crystallogr 66, 12-21.

Cohen, P., and Tcherpakov, M. (2010). Will the ubiquitin system furnish as many drug targets as protein kinases? Cell 143, 686-693.

David, D., Jagadeeshan, S., Hariharan, R., Nair, A. S., and Pillai, R. M. (2014). Smurf2 E3 ubiquitin ligase modulates proliferation and invasiveness of breast cancer cells in a CNKSR2 dependent manner. Cell division 9, 2.

Deng, S., and Huang, C. (2014). E3 ubiquitin ligases in regulating stress fiber, lamellipodium, and focal adhesion dynamics. Cell adhesion & migration 8, 49-54.

Doye, A., Mettouchi, A., and Lemichez, E. (2012). Assessing ubiquitylation of Rho GTPases in mammalian cells. Methods Mol Biol 827, 77-86.

Duc, C., Farman, N., Canessa, C. M., Bonvalet, J. P., and Rossier, B. C. (1994). Cell-specific expression of epithelial sodium channel alpha, beta, and gamma subunits in aldosterone-responsive epithelia from the rat: localization by in situ hybridization and immunocytochemistry. The Journal of cell biology 127, 1907-1921.

Emsley, P., Lohkamp, B., Scott, W. G., and Cowtan, K. (2010). Features and development of Coot. Acta Crystallogr D Biol Crystallogr 66, 486-501.

Ernst, A., Avvakumov, G., Tong, J., Fan, Y., Zhao, Y., Alberts, P., Persaud, A., Walker, J. R., Neculai, A. M., Neculai, D., et al. (2013). A strategy for modulation of enzymes in the ubiquitin system. Science 339, 590-595.

Escobedo, A., Gomes, T., Aragon, E., Martin-Malpartida, P., Ruiz, L., and Macias, M. J. (2014). Structural basis of the activation and degradation mechanisms of the E3 ubiquitin ligase Nedd4L. Structure 22, 1446-1457.

French, M. E., Kretzmann, B. R., and Hicke, L. (2009). Regulation of the RSP5 ubiquitin ligase by an intrinsic ubiquitin-binding site. The Journal of biological chemistry 284, 12071-12079.

Gallagher, E., Gao, M., Liu, Y. C., and Karin, M. (2006). Activation of the E3 ubiquitin ligase Itch through a phosphorylation-induced conformational change. Proceedings of the National Academy of Sciences of the United States of America 103, 1717-1722.

Herrador, A., Leon, S., Haguenauer-Tsapis, R., and Vincent, 0. (2013). A mechanism for protein monoubiquitination dependent on a trans-acting ubiquitin-binding domain. The Journal of biological chemistry 288, 16206-16211.

Huang, L., Kinnucan, E., Wang, G., Beaudenon, S., Howley, P. M., Huibregtse, J. M., and Pavletich, N. P. (1999). Structure of an E6AP-UbcH7 complex: insights into ubiquitination by the E2-E3 enzyme cascade. Science 286, 1321-1326.

Hubbard, S. J. T., J. M. (1993). 'NACCESS', Computer Program, Department of Biochemistry and Molecular Biology, University College London.

Huibregtse, J. M., Scheffner, M., Beaudenon, S., and Howley, P. M. (1995). A family of proteins structurally and functionally related to the E6-AP ubiquitin-protein ligase.

Proceedings of the National Academy of Sciences of the United States of America 92, 2563-2567.

Inoue, S., Hao, Z., Elia, A. J., Cescon, D., Zhou, L., Silvester, J., Snow, B., Harris, I. S., Sasaki, M., Li, W. Y., et al. (2013). Mule/Huwe1/Arf-BP1 suppresses Ras-driven tumorigenesis by preventing c-Myc/Miz1-mediated downregulation of p21 and p15. Genes & development 27, 1101-1114.

Jin, C., Yang, Y. A., Anver, M. R., Morris, N., Wang, X., and Zhang, Y. E. (2009). Smad ubiquitination regulatory factor 2 promotes metastasis of breast cancer cells by enhancing migration and invasiveness. Cancer research 69, 735-740.

Kamadurai, H. B., Qiu, Y., Deng, A., Harrison, J. S., Macdonald, C., Actis, M., Rodrigues, P., Miller, D. J., Souphron, J., Lewis, S. M., et al. (2013). Mechanism of ubiquitin ligation and lysine prioritization by a HECT E3. eLife 2, e00828.

Kamadurai, H. B., Souphron, J., Scott, D. C., Duda, D. M., Miller, D. J., Stringer, D., Piper, R. C., and Schulman, B. A. (2009). Insights into ubiquitin transfer cascades from a structure of a UbcH5B approximately ubiquitin-HECT (NEDD4L) complex. Molecular cell 36, 1095-1102.

Kamynina, E., Tauxe, C., and Staub, O. (2001). Distinct characteristics of two human Nedd4 proteins with respect to epithelial Na(+) channel regulation. American journal of physiology. Renal physiology 281, F469-477.

Kathman, S. G., Span, I., Smith, A. T., Xu, Z., Zhan, J., Rosenzweig, A. C., and Statsyuk, A. V. (2015). A Small Molecule That Switches a Ubiquitin Ligase From a Processive to a Distributive Enzymatic Mechanism. J Am Chem Soc.

Kay, B. K., Thai, S., and Volgina, V. V. (2009). Highthroughput biotinylation of proteins. Methods Mol Biol 498, 185-196.

Kim, H. C., and Huibregtse, J. M. (2009). Polyubiquitination by HECT E3s and the determinants of chain type specificity. Molecular and cellular biology 29, 3307-3318.

Kim, H. C., Steffen, A. M., Oldham, M. L., Chen, J., and Huibregtse, J. M. (2011). Structure and function of a HECT domain ubiquitin-binding site. EMBO reports 12, 334-341.

Kimura, T., Kawabe, H., Jiang, C., Zhang, W., Xiang, Y. Y., Lu, C., Salter, M. W., Brose, N., Lu, W. Y., and Rotin, D. (2011). Deletion of the ubiquitin ligase Nedd4L in lung epithelia causes cystic fibrosis-like disease. Proceedings of the National Academy of Sciences of the United States of America 108, 3216-3221.

Kirkpatrick, D. S., Gerber, S. A., and Gygi, S. P. (2005). The absolute quantification strategy: a general procedure for the quantification of proteins and post-translational modifications. Methods 35, 265-273.

Krissinel, E., and Henrick, K. (2007). Inference of macromolecular assemblies from crystalline state. Journal of molecular biology 372, 774-797.

Lifton, R. P., Gharavi, A. G., and Geller, D. S. (2001). Molecular mechanisms of human hypertension. Cell 104, 545-556.

Lin, D. Y., Diao, J., and Chen, J. (2012). Crystal structures of two bacterial HECT-like E3 ligases in complex with a human E2 reveal atomic details of pathogen-host interactions. Proceedings of the National Academy of Sciences of the United States of America 109, 1925-1930.

Lu, C., Pribanic, S., Debonneville, A., Jiang, C., and Rotin, D. (2007). The PY motif of ENaC, mutated in Liddle syndrome, regulates channel internalization, sorting and mobilization from subapical pool. Traffic 8, 1246-1264.

MacLean, B., Tomazela, D. M., Shulman, N., Chambers, M., Finney, G. L., Frewen, B., Kern, R., Tabb, D. L., Liebler, D. C., and MacCoss, M. J. (2010). Skyline: an open source document editor for creating and analyzing targeted proteomics experiments. Bioinformatics 26, 966-968.

Maddika, S., Kavela, S., Rani, N., Palicharla, V. R., Pokorny, J. L., Sarkaria, J. N., and Chen, J. (2011). WWP2 is an E3 ubiquitin ligase for PTEN. Nature cell biology 13, 728-733.

Mak, A. B., Ni, Z., Newel, J. A., Chen, G. I., Zhong, G., Karamboulas, K., Blakely, K., Smiley, S., Marcon, E., Roudeva, D., et al. (2010). A lentiviral functional proteomics approach identifies chromatin remodeling complexes important for the induction of pluripotency. Molecular & cellular proteomics: MCP 9, 811-823.

Mari, S., Ruetalo, N., Maspero, E., Stoffregen, M. C., Pasqualato, S., Polo, S., and Wiesner, S. (2014). Structural and functional framework for the autoinhibition of Nedd4-family ubiquitin ligases. Structure 22, 1639-1649.

Maspero, E., Mari, S., Valentini, E., Musacchio, A., Fish, A., Pasqualato, S., and Polo, S. (2011). Structure of the HECT: ubiquitin complex and its role in ubiquitin chain elongation. EMBO reports 12, 342-349.

Maspero, E., Valentini, E., Mari, S., Cecatiello, V., Soffientini, P., Pasqualato, S., and Polo, S. (2013). Structure of a ubiquitin-loaded HECT ligase reveals the molecular basis for catalytic priming. Nature structural & molecular biology 20, 696-701.

McCoy, A. J., Grosse-Kunstleve, R. W., Adams, P. D., Winn, M. D., Storoni, L. C., and Read, R. J. (2007). Phaser crystallographic software. J Appl Crystallogr 40, 658-674.

Mund, T., Lewis, M. J., Maslen, S., and Pelham, H. R. (2014). Peptide and small molecule inhibitors of HECT-type ubiquitin ligases. Proceedings of the National Academy of Sciences of the United States of America 111, 16736-16741.

Murshudov, G. N., Vagin, A. A., and Dodson, E. J. (1997). Refinement of macromolecular structures by the maximum-likelihood method. Acta Crystallogr D Biol Crystallogr 53, 240-255.

Nalepa, G., Rolfe, M., and Harper, J. W. (2006). Drug discovery in the ubiquitin-proteasome system. Nature reviews. Drug discovery 5, 596-613.

Ogunjimi, A. A., Wiesner, S., Briant, D. J., Varelas, X., Sicheri, F., Forman-Kay, J., and Wrana, J. L. (2010). The ubiquitin binding region of the Smurf HECT domain facilitates polyubiquitylation and binding of ubiquitylated substrates. The Journal of biological chemistry 285, 6308-6315.

Ordureau, A., Heo, J. M., Duda, D. M., Paulo, J. A., Olszewski, J. L., Yanishevski, D., Rinehart, J., Schulman, B. A., and Harper, J. W. (2015a). Defining roles of PARKIN and ubiquitin phosphorylation by PINK1 in mitochondrial quality control using a ubiquitin replacement strategy. Proceedings of the National Academy of Sciences of the United States of America 112, 6637-6642.

Ordureau, A., Munch, C., and Harper, J. W. (2015b). Quantifying ubiquitin signaling. Molecular cell 58, 660-676.

Ordureau, A., Sarraf, S. A., Duda, D. M., Heo, J. M., Jedrychowski, M. P., Sviderskiy, V. O., Olszewski, J. L., Koerber, J. T., Xie, T., Beausoleil, S. A., et al. (2014). Quantitative proteomics reveal a feedforward mechanism for mitochondrial PARKIN translocation and ubiquitin chain synthesis. Molecular cell 56, 360-375.

Otwinowski, Z., and Minor, W. (1997). Processing of X-ray diffraction data collected in oscillation mode. Method Enzymol 276, 307-326.

Persaud, A., Alberts, P., Mari, S., Tong, J., Murchie, R., Maspero, E., Safi, F., Moran, M. F., Polo, S., and Rotin, D. (2014). Tyrosine phosphorylation of NEDD4 activates its ubiquitin ligase activity. Science signaling 7, ra95.

Petroski, M. D. (2008). The ubiquitin system, disease, and drug discovery. BMC biochemistry 9 Suppl 1, S7.

Phillips, A. H., Zhang, Y., Cunningham, C. N., Zhou, L., Forrest, W. F., Liu, P. S., Steffek, M., Lee, J., Tam, C., Helgason, E., et al. (2013). Conformational dynamics control ubiquitin-deubiquitinase interactions and influence in vivo signaling. Proceedings of the National Academy of Sciences of the United States of America 110, 11379-11384.

Phu, L., Izrael-Tomasevic, A., Matsumoto, M. L., Bustos, D., Dynek, J. N., Fedorova, A. V., Bakalarski, C. E., Arnott, D., Deshayes, K., Dixit, V. M., et al. (2011). Improved quantitative mass spectrometry methods for characterizing complex ubiquitin signals. Molecular & cellular proteomics: MCP 10, M110 003756.

Riling, C., Kamadurai, H., Kumar, S., O'Leary, C. E., Wu, K. P., Manion, E. E., Ying, M., Schulman, B. A., and Oliver, P. M. (2015). Itch WW domains inhibit its E3 ubiquitin ligase activity by blocking E2-E3 transthiolation. The Journal of biological chemistry.

Rohde, J. R., Breitkreutz, A., Chenal, A., Sansonetti, P. J., and Parsot, C. (2007). Type III secretion effectors of the IpaH family are E3 ubiquitin ligases. Cell Host Microbe 1, 77-83.

Ronchi, V. P., Klein, J. M., and Haas, A. L. (2013). E6AP/UBE3A ubiquitin ligase harbors two E2-ubiquitin binding sites. The Journal of biological chemistry 288, 10349-10360.

Ronzaud, C., Loffing-Cueni, D., Hausel, P., Debonneville, A., Malsure, S. R., Fowler-Jaeger, N., Boase, N. A., Perrier, R., Maillard, M., Yang, B., et al. (2013). Renal tubular NEDD4-2 deficiency causes NCC-mediated salt-dependent hypertension. J Clin Invest 123, 657-665.

Rossi, M., Rotblat, B., Ansell, K., Amelio, I., Caraglia, M., Misso, G., Bernassola, F., Cavasotto, C. N., Knight, R. A., Ciechanover, A., et al. (2014). High throughput screening for inhibitors of the HECT ubiquitin E3 ligase ITCH identifies antidepressant drugs as regulators of autophagy. Cell death & disease 5, e1203.

Rotin, D., and Kumar, S. (2009). Physiological functions of the HECT family of ubiquitin ligases. Nature reviews. Molecular cell biology 10, 398-409.

Sato, T., and Clevers, H. (2013). Growing self-organizing mini-guts from a single intestinal stem cell: mechanism and applications. Science 340, 1190-1194.

Scheffner, M., and Kumar, S. (2014). Mammalian HECT ubiquitin-protein ligases: biological and pathophysiological aspects. Biochimica et biophysica acta 1843, 61-74.

Sheng, Y., Hong, J. H., Doherty, R., Srikumar, T., Shloush, J., Avvakumov, G. V., Walker, J. R., Xue, S., Neculai, D., Wan, J. W., et al. (2012). A human ubiquitin conjugating enzyme (E2)-HECT E3 ligase structure-function screen. Molecular & cellular proteomics: MCP 11, 329-341.

Simpson, K. J., Selfors, L. M., Bui, J., Reynolds, A., Leake, D., Khvorova, A., and Brugge, J. S. (2008). Identification of genes that regulate epithelial cell migration using an siRNA screening approach. Nature cell biology 10, 1027-1038.

Tonikian, R., Zhang, Y., Boone, C., and Sidhu, S. S. (2007). Identifying specificity profiles for peptide recognition modules from phage-displayed peptide libraries. Nature protocols 2, 1368-1386.

Torrino, S., Visvikis, O., Doye, A., Boyer, L., Stefani, C., Munro, P., Bertoglio, J., Gacon, G., Mettouchi, A., and Lemichez, E. (2011). The E3 ubiquitin-ligase HACE1 catalyzes the ubiquitylation of active Rac1. Developmental cell 21, 959-965.

Verdecia, M. A., Joazeiro, C. A., Wells, N. J., Ferrer, J. L., Bowman, M. E., Hunter, T., and Noel, J. P. (2003). Conformational flexibility underlies ubiquitin ligation mediated by the WWP1 HECT domain E3 ligase. Molecular cell 11, 249-259.

Wang, H. R., Zhang, Y., Ozdamar, B., Ogunjimi, A. A., Alexandrova, E., Thomsen, G. H., and Wrana, J. L. (2003). Regulation of cell polarity and protrusion formation by targeting RhoA for degradation. Science 302, 1775-1779.

Wang, M., Guo, L., Wu, Q., Zeng, T., Lin, Q., Qiao, Y., Wang, Q., Liu, M., Zhang, X., Ren, L., et al. (2014). ATR/Chk1/Smurf1 pathway determines cell fate after DNA damage by controlling RhoB abundance. Nature communications 5, 4901.

Wiesner, S., Ogunjimi, A. A., Wang, H. R., Rotin, D., Sicheri, F., Wrana, J. L., and Forman-Kay, J. D. (2007). Autoinhibition of the HECT-type ubiquitin ligase Smurf2 through its C2 domain. Cell 130, 651-662.

Wilson, F. H., Disse-Nicodeme, S., Choate, K. A., Ishikawa, K., Nelson-Williams, C., Desitter, I., Gunel, M., Milford, D. V., Lipkin, G. W., Achard, J. M., et al. (2001). Human hypertension caused by mutations in WNK kinases. Science 293, 1107-1112.

Winn, M. D., Ballard, C. C., Cowtan, K. D., Dodson, E. J., Emsley, P., Evans, P. R., Keegan, R. M., Krissinel, E. B., Leslie, A. G., McCoy, A., et al. (2011). Overview of the CCP4 suite and current developments. Acta Crystallogr D Biol Crystallogr 67, 235-242.

Zhang, W., and Sidhu, S. S. (2014). Development of inhibitors in the ubiquitination cascade. FEBS letters 588, 356-367.

Zhang, Y., Zhou, L., Rouge, L., Phillips, A. H., Lam, C., Liu, P., Sandoval, W., Helgason, E., Murray, J. M., Wertz, I. E., et al. (2013). Conformational stabilization of ubiquitin yields potent and selective inhibitors of USP7. Nature chemical biology 9, 51-58.

What is claimed is:

1. A ubiquitin variant (Ubv) polypeptide that binds to NEDD4L, wherein the sequence of said Ubv polypeptide comprises a sequence selected from the group consisting of SEQ ID NOs:9-12.

2. A Ubv polypeptide that binds to SMURF2 (S2), wherein the sequence of said Ubv polypeptide comprises a sequence that is at least 90% identical to a sequence selected from the group consisting of SEQ ID NOs:18-22.

3. The Ubv polypeptide of claim 2, wherein the sequence of said Ubv polypeptide comprises a sequence selected from the group consisting of SEQ ID NOs:18-22.

4. A Ubv polypeptide that binds to HACE1 (HA), wherein the sequence of said Ubv polypeptide comprises a sequence that is at least 90% identical to a sequence selected from the group consisting of SEQ ID NOs:54-56.

5. The Ubv polypeptide of claim 4, wherein the sequence of said Ubv polypeptide comprises a sequence selected from the group consisting of SEQ ID NOs:54-56.

6. A Ubv polypeptide that binds to WWP2 (P2), wherein the sequence of said Ubv polypeptide comprises a sequence that is at least 90% identical to a sequence selected from the group consisting of SEQ ID NOs:27-30.

7. The Ubv polypeptide of claim 6, wherein the sequence of said Ubv polypeptide comprises a sequence selected from the group consisting of SEQ ID NOs:27-30.

* * * * *

SEQUENCE LISTING

<160> NUMBER OF SEQ ID NOS: 87

<210> SEQ ID NO 1
<211> LENGTH: 78
<212> TYPE: PRT
<213> ORGANISM: Homo sapiens
<220> FEATURE:
<221> NAME/KEY: MISC_FEATURE
<222> LOCATION: (77)..(77)
<223> OTHER INFORMATION: Xaa is Gly or absent
<220> FEATURE:
<221> NAME/KEY: MISC_FEATURE
<222> LOCATION: (78)..(78)
<223> OTHER INFORMATION: Xaa is Gly or absent

<400> SEQUENCE: 1

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Xaa Xaa
65                  70                  75

<210> SEQ ID NO 2
<211> LENGTH: 78
<212> TYPE: PRT
<213> ORGANISM: Artificial Sequence
<220> FEATURE:
<223> OTHER INFORMATION: Synthetic Construct

<400> SEQUENCE: 2

Met His Ile Leu Val Lys Thr Leu Arg Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Leu Phe Gly Gly Asn
        35                  40                  45

Lys Leu Glu Asp Gly Arg Thr Leu Ser Asp Tyr Asn Ile Gln Lys Glu
    50                  55                  60

Ser Asn Leu Tyr Leu Leu Leu Arg Arg Leu Gly Ser Lys Phe
65                  70                  75

<210> SEQ ID NO 3
<211> LENGTH: 78
<212> TYPE: PRT
<213> ORGANISM: Artificial Sequence
<220> FEATURE:
<223> OTHER INFORMATION: Synthetic Construct

<400> SEQUENCE: 3

Met Gln Ile Phe Val Ile Thr His Thr Trp Arg Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Leu Phe Ala Arg Gln
        35                  40                  45

Lys Leu Glu Asp Gly Arg Thr Leu Ser Asp Tyr Asn Ile Gln Lys Asp
    50                  55                  60

Ser Thr Leu His Leu Val Leu Ile Arg Arg Val Ser Lys Arg
65                  70                  75

<210> SEQ ID NO 4
<211> LENGTH: 79
<212> TYPE: PRT
<213> ORGANISM: Artificial Sequence
<220> FEATURE:
<223> OTHER INFORMATION: Synthetic Construct

<400> SEQUENCE: 4

Met Gln Ile Phe Val Lys Thr Leu Thr Gly Leu Ser Ile Thr Thr Leu

```
            1               5                  10                 15
        Glu Val Glu Pro Ser Asp Thr Ile Glu Asn Val Lys Ala Lys Ile Gln
                        20                  25                  30

Asp Lys Glu Gly Ile Pro Pro Asp Gln Gln Ile Leu Ile Phe Gly Gly
                    35                  40                  45

Lys Arg Leu Glu Asp Gly Arg Thr Leu Ser Asp Tyr Asn Ile Gln Lys
            50                  55                  60

Lys Ser Ser Leu Tyr Leu Leu Met Arg Leu Arg Gly Val Ser Arg
        65                  70                  75

<210> SEQ ID NO 5
<211> LENGTH: 78
<212> TYPE: PRT
<213> ORGANISM: Artificial Sequence
<220> FEATURE:
<223> OTHER INFORMATION: Synthetic Construct

<400> SEQUENCE: 5

Met Pro Ile Leu Val Gln Thr Leu Arg Gly Gln Ser Ile Ile Leu Glu
        1               5                   10                  15

Val Glu Pro Ser Asp Thr Ile Glu Asn Val Lys Ala Lys Ile Gln Asp
                        20                  25                  30

Lys Glu Gly Ile Pro Pro Asp Gln Gln Phe Leu Ile Phe Ala Arg Thr
                    35                  40                  45

His Leu Glu Asp Gly Arg Thr Leu Ser Asp Tyr Asn Ile Gln Lys Gly
            50                  55                  60

Ser Thr Leu Tyr Leu Leu Leu Arg Phe His Gly Thr Val Ala
        65                  70                  75

<210> SEQ ID NO 6
<211> LENGTH: 78
<212> TYPE: PRT
<213> ORGANISM: Artificial Sequence
<220> FEATURE:
<223> OTHER INFORMATION: Synthetic Construct

<400> SEQUENCE: 6

Met Gln Ile Phe Val Lys Thr Met Arg Arg Glu Ser Ile Ser Leu Glu
        1               5                   10                  15

Val Glu Pro Ser Asp Thr Ile Glu Asn Val Lys Ala Lys Ile Gln Asp
                        20                  25                  30

Lys Glu Gly Ile Pro Pro Asp Gln Gln Arg Leu Phe Phe Thr Gly Lys
                    35                  40                  45

Gln Leu Glu Asp Gly Arg Thr Leu Ser Asp Tyr Asn Ile Gln Lys Glu
            50                  55                  60

Ser Thr Leu His Leu Val Lys Arg Leu Pro Gly Arg Gln Tyr
        65                  70                  75

<210> SEQ ID NO 7
<211> LENGTH: 78
<212> TYPE: PRT
<213> ORGANISM: Artificial Sequence
<220> FEATURE:
<223> OTHER INFORMATION: Synthetic Construct

<400> SEQUENCE: 7

Met Gln Ile Phe Val Lys Thr Leu Ala Gly Trp Gly Ile Thr Leu Glu
        1               5                   10                  15

Val Glu Pro Ser Asp Thr Ile Glu Asn Val Lys Ala Lys Ile Gln Asp
                        20                  25                  30
```

Lys Glu Gly Ile Pro Pro Asp Gln Gln Arg Leu Ile Phe Ala Gly Lys
            35                  40                  45

Gln Leu Glu Asp Gly Arg Thr Leu Ser Asp Tyr Asn Ile Arg Tyr Asp
 50                  55                  60

Ser Gln Leu His Leu Val Gly Arg Leu Arg Gly Gly Gly
65                  70                  75

<210> SEQ ID NO 8
<211> LENGTH: 78
<212> TYPE: PRT
<213> ORGANISM: Artificial Sequence
<220> FEATURE:
<223> OTHER INFORMATION: Synthetic Construct

<400> SEQUENCE: 8

Met Gln Ile Tyr Val Lys Thr Leu Thr Arg Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Val Gly Lys
            35                  40                  45

Gln Leu Glu Asp Gly Arg Thr Leu Ser Asp Tyr Asn Ile Gln Lys Glu
 50                  55                  60

Ser Ser Leu Tyr Leu Val Leu Arg Leu Arg Gly Gly Gly
65                  70                  75

<210> SEQ ID NO 9
<211> LENGTH: 78
<212> TYPE: PRT
<213> ORGANISM: Artificial Sequence
<220> FEATURE:
<223> OTHER INFORMATION: Synthetic Construct

<400> SEQUENCE: 9

Met Arg Ile Phe Val Arg Thr Pro Thr Arg Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Val Leu Ile Phe Ala Gly Asn
            35                  40                  45

Arg Leu Glu Asp Gly Arg Thr Leu Ser Asp Tyr Asn Ile Pro Lys Glu
 50                  55                  60

Ser Thr Leu Tyr Leu Phe Met Arg Leu Arg Gly Leu Glu Asn
65                  70                  75

<210> SEQ ID NO 10
<211> LENGTH: 78
<212> TYPE: PRT
<213> ORGANISM: Artificial Sequence
<220> FEATURE:
<223> OTHER INFORMATION: Synthetic Construct

<400> SEQUENCE: 10

Met Gln Ile Leu Val Lys Thr Pro Thr Trp Gln Thr Ile Phe Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Val Leu Ile Phe His Gly Lys
            35                  40                  45

```
Lys Leu Glu Asp Gly Arg Thr Leu Ser Asp Tyr Asn Ile His His Glu
    50                  55                  60

Ser Asn Leu Tyr Leu Phe Leu Lys Leu Pro Gly Leu Gly Asp
65                  70                  75
```

<210> SEQ ID NO 11
<211> LENGTH: 78
<212> TYPE: PRT
<213> ORGANISM: Artificial Sequence
<220> FEATURE:
<223> OTHER INFORMATION: Synthetic Construct

<400> SEQUENCE: 11

```
Met Gln Ile Phe Val Trp Thr Leu Phe Arg Lys Pro Ile Ile Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Gly Gly
65                  70                  75
```

<210> SEQ ID NO 12
<211> LENGTH: 78
<212> TYPE: PRT
<213> ORGANISM: Artificial Sequence
<220> FEATURE:
<223> OTHER INFORMATION: Synthetic Construct

<400> SEQUENCE: 12

```
Met Tyr Ile Tyr Val Trp Thr Leu Phe Arg Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Ala
    50                  55                  60

Ser Leu Leu His Leu Val Leu Arg Leu Arg Gly Gly Gly Gly
65                  70                  75
```

<210> SEQ ID NO 13
<211> LENGTH: 78
<212> TYPE: PRT
<213> ORGANISM: Artificial Sequence
<220> FEATURE:
<223> OTHER INFORMATION: Synthetic Construct

<400> SEQUENCE: 13

```
Met His Ile Phe Val Lys Thr Leu Thr Gly Arg Val Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Thr Leu Leu Phe Gly Gly Lys
        35                  40                  45

Gln Leu Glu Asp Gly Arg Thr Leu Ser Asp Tyr Asn Ile Tyr Lys Val
    50                  55                  60

Ser Thr Leu Tyr Leu Leu Tyr Arg Leu Arg Gly Gly Glu Leu
```

65          70          75

<210> SEQ ID NO 14
<211> LENGTH: 78
<212> TYPE: PRT
<213> ORGANISM: Artificial Sequence
<220> FEATURE:
<223> OTHER INFORMATION: Synthetic Construct

<400> SEQUENCE: 14

Met Gln Ile Phe Val Gln Thr Tyr Thr Trp Glu Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Gln
        35                  40                  45

Gln Leu Glu Asp Gly Arg Thr Leu Ser Asp Tyr Asn Ile Pro Lys Gln
    50                  55                  60

Ser Ser Leu Tyr Leu Val Leu Arg Leu Arg Gly Gly Gly
65                  70                  75

<210> SEQ ID NO 15
<211> LENGTH: 78
<212> TYPE: PRT
<213> ORGANISM: Artificial Sequence
<220> FEATURE:
<223> OTHER INFORMATION: Synthetic Construct

<400> SEQUENCE: 15

Met Arg Ile Phe Val Gln Thr Phe Thr Trp Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Thr Leu Ile Phe Ala Gly Lys
        35                  40                  45

Gln Leu Glu Asp Gly Arg Thr Leu Ser Asp Tyr Asn Ile Gln Lys Val
    50                  55                  60

Ser Ser Leu Tyr Leu Met Phe Arg Leu Arg Gly Arg Ser Ser
65                  70                  75

<210> SEQ ID NO 16
<211> LENGTH: 78
<212> TYPE: PRT
<213> ORGANISM: Artificial Sequence
<220> FEATURE:
<223> OTHER INFORMATION: Synthetic Construct

<400> SEQUENCE: 16

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Thr Leu Leu Phe Ser Gly Lys
        35                  40                  45

Gln Leu Glu Asp Gly Arg Thr Leu Ser Asp Tyr Asn Ile Gln Gln Val
    50                  55                  60

Ser Thr Leu Tyr Leu Leu Phe Arg Leu Arg Gly Leu Arg His
65                  70                  75

<210> SEQ ID NO 17

<211> LENGTH: 78
<212> TYPE: PRT
<213> ORGANISM: Artificial Sequence
<220> FEATURE:
<223> OTHER INFORMATION: Synthetic Construct

<400> SEQUENCE: 17

Met Gln Ile Phe Met Lys Thr Leu Pro Gly Lys Ser Ile Ile Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Thr Leu Leu Phe Ala Gly Lys
        35                  40                  45

Arg Leu Glu Asp Gly Arg Thr Leu Ser Asp Tyr Asn Ile Gln Asn Gly
    50                  55                  60

Ser Thr Leu Tyr Leu Met Phe Arg Leu Arg Gly Gly Gly Gly
65                  70                  75

<210> SEQ ID NO 18
<211> LENGTH: 78
<212> TYPE: PRT
<213> ORGANISM: Artificial Sequence
<220> FEATURE:
<223> OTHER INFORMATION: Synthetic Construct

<400> SEQUENCE: 18

Met Gln Ile Phe Val Lys Thr Leu Thr Arg Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Ile Leu Val Phe Ala Gly Lys
        35                  40                  45

Ser Leu Glu Asp Gly Arg Thr Leu Ser Asp Tyr Asn Ile Gln Lys Gly
    50                  55                  60

Ser Ser Leu Trp Leu Lys Leu Arg Leu Arg Gly Gly Gly Gly
65                  70                  75

<210> SEQ ID NO 19
<211> LENGTH: 78
<212> TYPE: PRT
<213> ORGANISM: Artificial Sequence
<220> FEATURE:
<223> OTHER INFORMATION: Synthetic Construct

<400> SEQUENCE: 19

Met Gln Ile Phe Val Lys Thr Pro Thr Arg Lys Ser Ile Ala Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Ile Leu Ile Phe Ala Gly Lys
        35                  40                  45

Gln Leu Glu Asp Gly Arg Thr Leu Ser Asp Tyr Asn Ile Gln Met Gln
    50                  55                  60

Ser Ile Leu Tyr Leu Leu Arg Arg Leu Pro Arg Val His Ala
65                  70                  75

<210> SEQ ID NO 20
<211> LENGTH: 78
<212> TYPE: PRT
<213> ORGANISM: Artificial Sequence
<220> FEATURE:

<223> OTHER INFORMATION: Synthetic Construct

<400> SEQUENCE: 20

Met Gln Ile Cys Val Lys Thr Pro Thr Arg Lys Leu Ile Asn Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Leu Phe Ala Gly Lys
        35                  40                  45

Gln Leu Glu Asp Gly Arg Thr Leu Ser Asp Tyr Asn Ile Gln Gln Glu
    50                  55                  60

Ser Thr Leu Tyr Leu Val Lys Arg Leu Arg Gly Gly Gly Gly
65                  70                  75

<210> SEQ ID NO 21
<211> LENGTH: 78
<212> TYPE: PRT
<213> ORGANISM: Artificial Sequence
<220> FEATURE:
<223> OTHER INFORMATION: Synthetic Construct

<400> SEQUENCE: 21

Met Leu Ile Phe Val Trp Thr Phe Lys Gly Asn Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Arg Lys
        35                  40                  45

Gln Leu Glu Asp Gly Arg Thr Leu Ser Asp Tyr Asn Ile Leu Lys Glu
    50                  55                  60

Ser Thr Leu Leu Leu Val Arg Arg Leu Arg Gly Gly Gly Gly
65                  70                  75

<210> SEQ ID NO 22
<211> LENGTH: 78
<212> TYPE: PRT
<213> ORGANISM: Artificial Sequence
<220> FEATURE:
<223> OTHER INFORMATION: Synthetic Construct

<400> SEQUENCE: 22

Met Gln Ile Ser Val Lys Thr Leu Ser Gly Lys Asn Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Leu Leu Ile Phe Val Gly Lys
        35                  40                  45

Asn Leu Glu Asp Gly Arg Thr Leu Ser Asp Tyr Asn Ile Leu Lys Tyr
    50                  55                  60

Ser Thr Leu Tyr Leu Leu Lys Gly Ile Arg Gly Arg Glu Lys
65                  70                  75

<210> SEQ ID NO 23
<211> LENGTH: 78
<212> TYPE: PRT
<213> ORGANISM: Artificial Sequence
<220> FEATURE:
<223> OTHER INFORMATION: Synthetic Construct

<400> SEQUENCE: 23

```
Met His Ile Phe Val Lys Thr Leu Arg Gly Trp Ser Ile Thr Leu Glu
1               5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Ile Leu Ile Phe Ala Arg Lys
            35                  40                  45

Lys Leu Glu Asp Gly Arg Thr Leu Ser Asp Tyr Asn Ile Gln Glu Lys
50                  55                  60

Ser Ser Leu Tyr Leu Phe Leu Arg Leu Leu Arg Lys Ser Arg
65                  70                  75
```

<210> SEQ ID NO 24
<211> LENGTH: 78
<212> TYPE: PRT
<213> ORGANISM: Artificial Sequence
<220> FEATURE:
<223> OTHER INFORMATION: Synthetic Construct

<400> SEQUENCE: 24

```
Met Glu Ile Phe Val Lys Thr Leu Ser Gly Lys Ser Ile Thr Leu Glu
1               5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Leu Leu Phe Gly Gly Arg
            35                  40                  45

Gln Leu Glu Asp Gly Arg Thr Leu Ser Asp Tyr Asn Ile Lys Tyr Glu
50                  55                  60

Ser Thr Leu Ser Leu Leu Phe Arg Leu Arg Gly Tyr Lys Val
65                  70                  75
```

<210> SEQ ID NO 25
<211> LENGTH: 78
<212> TYPE: PRT
<213> ORGANISM: Artificial Sequence
<220> FEATURE:
<223> OTHER INFORMATION: Synthetic Construct

<400> SEQUENCE: 25

```
Met Arg Ile Ser Val Tyr Thr Leu Pro Gly Lys Thr Ile Lys Leu Glu
1               5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Leu Leu Ile Phe Ala Gly Arg
            35                  40                  45

Gln Leu Glu Asp Gly Arg Thr Leu Ser Asp Tyr Asn Ile Gln Lys Glu
50                  55                  60

Ser Thr Leu His Leu Met Leu Arg Leu Arg Gly Lys Ala Lys
65                  70                  75
```

<210> SEQ ID NO 26
<211> LENGTH: 78
<212> TYPE: PRT
<213> ORGANISM: Artificial Sequence
<220> FEATURE:
<223> OTHER INFORMATION: Synthetic Construct

<400> SEQUENCE: 26

```
Met Pro Ile Leu Val Lys Thr Leu Arg Gly Gln Ser Ile Ile Leu Glu
1               5                   10                  15

Val Glu Pro Ser Asp Thr Ile Glu Asn Val Lys Ala Lys Ile Gln Asp
```

```
                        20                  25                  30

Lys Glu Gly Ile Pro Pro Asp Gln Gln Phe Leu Ile Phe Ala Arg Lys
            35                  40                  45

His Leu Glu Asp Gly Arg Thr Leu Ser Asp Tyr Asn Ile Gln Lys Arg
         50                  55                  60

Ser Thr Leu Tyr Leu Phe Leu Arg Phe His Gly Met Val Ala
 65                  70                  75

<210> SEQ ID NO 27
<211> LENGTH: 78
<212> TYPE: PRT
<213> ORGANISM: Artificial Sequence
<220> FEATURE:
<223> OTHER INFORMATION: Synthetic Construct

<400> SEQUENCE: 27

Met Gln Ile Phe Val Lys Thr Phe Thr Trp Lys Thr Ile Thr Leu Glu
 1               5                  10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
         35                  40                  45

Gln Leu Glu Asp Gly Arg Thr Leu Ser Asp Tyr Asn Ile Leu Asn Glu
     50                  55                  60

Ser Thr Leu Tyr Leu Ile Leu Arg Leu Pro Gly Phe Ser Val
 65                  70                  75

<210> SEQ ID NO 28
<211> LENGTH: 78
<212> TYPE: PRT
<213> ORGANISM: Artificial Sequence
<220> FEATURE:
<223> OTHER INFORMATION: Synthetic Construct

<400> SEQUENCE: 28

Met Leu Ile Phe Val Lys Thr Phe Lys Trp Ile Thr Ile Thr Leu Glu
 1               5                  10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
         35                  40                  45

Gln Leu Glu Asp Gly Arg Thr Leu Ser Asp Tyr Asn Ile Lys Asn Arg
     50                  55                  60

Ser Ser Leu His Leu Val Leu Arg Leu Pro Gly Gly Arg Arg
 65                  70                  75

<210> SEQ ID NO 29
<211> LENGTH: 78
<212> TYPE: PRT
<213> ORGANISM: Artificial Sequence
<220> FEATURE:
<223> OTHER INFORMATION: Synthetic Construct

<400> SEQUENCE: 29

Met Gln Ile Leu Val Lys Thr Phe Thr Trp Lys Thr Ile Thr Leu Glu
 1               5                  10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
         35                  40                  45
```

```
Gln Leu Glu Asp Gly Arg Thr Leu Ser Asp Tyr Asn Ile Lys Met Gly
        50                  55                  60
Ser Ser Leu Tyr Leu Val Leu Arg Leu Pro Gly Gln Arg Ile
65                  70                  75
```

<210> SEQ ID NO 30
<211> LENGTH: 78
<212> TYPE: PRT
<213> ORGANISM: Artificial Sequence
<220> FEATURE:
<223> OTHER INFORMATION: Synthetic Construct

<400> SEQUENCE: 30

```
Met Gln Ile Leu Val Lys Thr Leu Thr Leu Lys Thr Ile Ala Leu Glu
1               5                   10                  15
Val Glu Pro Ser Asp Thr Ile Glu Asn Val Lys Ala Lys Ile Gln Asp
            20                  25                  30
Lys Glu Gly Ile Pro Pro Asp Gln Gln Arg Leu Phe Phe Val Gly Lys
        35                  40                  45
Gln Leu Glu Asp Gly Arg Thr Leu Ser Asp Tyr Asn Ile His Asn Glu
    50                  55                  60
Ser Thr Leu Tyr Leu Ala Leu Arg Leu Pro Val Asn Arg Leu
65                  70                  75
```

<210> SEQ ID NO 31
<211> LENGTH: 78
<212> TYPE: PRT
<213> ORGANISM: Artificial Sequence
<220> FEATURE:
<223> OTHER INFORMATION: Synthetic Construct

<400> SEQUENCE: 31

```
Met Gln Ile Ser Val Lys Thr Leu Thr Gly Leu Ser Ile Thr Leu Glu
1               5                   10                  15
Val Glu Pro Ser Asp Thr Ile Glu Asn Val Lys Ala Lys Ile Gln Asp
            20                  25                  30
Lys Glu Gly Ile Pro Pro Asp Gln Gln Ile Leu Ile Phe Ala Ser Lys
        35                  40                  45
Lys Leu Glu Asp Gly Arg Thr Leu Ser Asp Tyr Asn Ile His Lys Glu
    50                  55                  60
Ser Ile Leu His Leu Leu Arg Arg Leu Pro Asp Ser His Thr
65                  70                  75
```

<210> SEQ ID NO 32
<211> LENGTH: 78
<212> TYPE: PRT
<213> ORGANISM: Artificial Sequence
<220> FEATURE:
<223> OTHER INFORMATION: Synthetic Construct

<400> SEQUENCE: 32

```
Met Gln Ile Leu Val Arg Thr Leu Thr Arg Lys Thr Ile Cys Leu Glu
1               5                   10                  15
Val Glu Pro Ser Asp Thr Ile Glu Asn Val Lys Ala Lys Ile Gln Asp
            20                  25                  30
Lys Glu Gly Ile Pro Pro Asp Gln Gln Arg Leu Ile Phe Ala Gly Lys
        35                  40                  45
Gln Leu Glu Asp Gly Arg Thr Leu Ser Asp Tyr Asn Ile Gln Lys Gly
    50                  55                  60
```

Ser Arg Leu His Leu Leu Lys Arg Leu Pro Trp Arg Arg Thr
65                  70                  75

<210> SEQ ID NO 33
<211> LENGTH: 78
<212> TYPE: PRT
<213> ORGANISM: Artificial Sequence
<220> FEATURE:
<223> OTHER INFORMATION: Synthetic Construct

<400> SEQUENCE: 33

Met Thr Ile Phe Val Lys Thr Leu Arg Arg Thr Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Gln Leu Ile Phe Gly Ala Lys
        35                  40                  45

Lys Leu Glu Asp Gly Arg Thr Leu Ser Asp Tyr Asn Ile Lys Asn Gln
    50                  55                  60

Ser Ser Leu His Leu Leu Lys Lys Leu Leu Val Thr Pro Leu
65                  70                  75

<210> SEQ ID NO 34
<211> LENGTH: 78
<212> TYPE: PRT
<213> ORGANISM: Artificial Sequence
<220> FEATURE:
<223> OTHER INFORMATION: Synthetic Construct

<400> SEQUENCE: 34

Met Thr Ile Phe Val Lys Thr Leu Arg Arg Thr Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Gln Leu Ile Phe Gly Ala Lys
        35                  40                  45

Lys Leu Glu Asp Gly Arg Thr Leu Ser Asp Tyr Asn Ile Lys Asn Gln
    50                  55                  60

Ser Ser Leu His Leu Leu Lys Lys Leu Leu Val Thr Pro Leu
65                  70                  75

<210> SEQ ID NO 35
<211> LENGTH: 78
<212> TYPE: PRT
<213> ORGANISM: Artificial Sequence
<220> FEATURE:
<223> OTHER INFORMATION: Synthetic Construct

<400> SEQUENCE: 35

Met Gln Ile Val Val Gly Thr Leu Thr Gly Lys Pro Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Leu Leu Ile Phe Ala Gly Lys
        35                  40                  45

Gln Leu Glu Asp Gly Arg Thr Leu Ser Asp Tyr Asn Ile Arg Arg Gln
    50                  55                  60

Ser Ile Leu Ser Leu Val Met Arg Leu Arg Gly Asp Lys Pro
65                  70                  75

```
<210> SEQ ID NO 36
<211> LENGTH: 78
<212> TYPE: PRT
<213> ORGANISM: Artificial Sequence
<220> FEATURE:
<223> OTHER INFORMATION: Synthetic Construct

<400> SEQUENCE: 36

Met Gln Ile Leu Val Gly Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Asn Ala
    50                  55                  60

Ser Ile Leu Thr Leu Phe Leu Arg Leu Arg Ile Met Thr Val
65                  70                  75

<210> SEQ ID NO 37
<211> LENGTH: 78
<212> TYPE: PRT
<213> ORGANISM: Artificial Sequence
<220> FEATURE:
<223> OTHER INFORMATION: Synthetic Construct

<400> SEQUENCE: 37

Met Gln Ile Val Val Gly Thr Leu Thr Gly Lys Pro Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Leu Leu Ile Phe Ala Gly Lys
        35                  40                  45

Gln Leu Glu Asp Gly Arg Thr Leu Ser Asp Tyr Asn Ile Arg Arg Gln
    50                  55                  60

Ser Ile Leu Ser Leu Val Met Arg Leu Arg Gly Asp Lys Pro
65                  70                  75

<210> SEQ ID NO 38
<211> LENGTH: 78
<212> TYPE: PRT
<213> ORGANISM: Artificial Sequence
<220> FEATURE:
<223> OTHER INFORMATION: Synthetic Construct

<400> SEQUENCE: 38

Met Pro Ile Ile Val Gly Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Asn Leu Glu Asp Gly Arg Thr Leu Ser Asp Tyr Asn Ile Gln Asn Glu
    50                  55                  60

Ser Ser Leu Thr Leu Val Leu Arg Arg His Val Val Arg Asn
65                  70                  75

<210> SEQ ID NO 39
<211> LENGTH: 78
<212> TYPE: PRT
<213> ORGANISM: Artificial Sequence
```

<220> FEATURE:
<223> OTHER INFORMATION: Synthetic Construct

<400> SEQUENCE: 39

Met Gln Ile Leu Val Lys Thr Pro Ala Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Thr Gly Lys
        35                  40                  45

Gln Leu Glu Asp Gly Arg Thr Leu Ser Asp Tyr Asn Ile Gln Lys Val
    50                  55                  60

Ser Thr Leu His Leu Val Lys Arg Leu Pro Pro Ser Val Val
65                  70                  75

<210> SEQ ID NO 40
<211> LENGTH: 78
<212> TYPE: PRT
<213> ORGANISM: Artificial Sequence
<220> FEATURE:
<223> OTHER INFORMATION: Synthetic Construct

<400> SEQUENCE: 40

Met Arg Ile Leu Val Lys Thr Pro Thr Arg Lys Thr Ile Asn Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Lys Leu Ile Phe Val Gly Lys
        35                  40                  45

Pro Leu Glu Asp Gly Arg Thr Leu Ser Asp Tyr Asn Ile Gln Lys Glu
    50                  55                  60

Ser Thr Leu Tyr Leu Val Phe Arg Leu Pro Val Pro Arg Lys
65                  70                  75

<210> SEQ ID NO 41
<211> LENGTH: 78
<212> TYPE: PRT
<213> ORGANISM: Artificial Sequence
<220> FEATURE:
<223> OTHER INFORMATION: Synthetic Construct

<400> SEQUENCE: 41

Met Gln Ile Ala Val Lys Thr Pro Thr Arg Gln Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Lys Arg Leu Pro Gly His Ser Asp
65                  70                  75

<210> SEQ ID NO 42
<211> LENGTH: 78
<212> TYPE: PRT
<213> ORGANISM: Artificial Sequence
<220> FEATURE:
<223> OTHER INFORMATION: Synthetic Construct

<400> SEQUENCE: 42

Met Gln Ile Phe Val Lys Thr Pro Thr Arg Lys Ser Ile Ser Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Pro Gly Thr Ile Lys
65                  70                  75

<210> SEQ ID NO 43
<211> LENGTH: 78
<212> TYPE: PRT
<213> ORGANISM: Artificial Sequence
<220> FEATURE:
<223> OTHER INFORMATION: Synthetic Construct

<400> SEQUENCE: 43

Met His Ile Phe Val Lys Thr Pro Thr Arg Lys Thr Ile Ile Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Thr
        35                  40                  45

Gln Leu Glu Asp Gly Arg Thr Leu Ser Asp Tyr Asn Ile Gln Asn Tyr
    50                  55                  60

Ser Thr Leu His Leu Val Arg Arg Leu Pro Gly Lys Ser Arg
65                  70                  75

<210> SEQ ID NO 44
<211> LENGTH: 78
<212> TYPE: PRT
<213> ORGANISM: Artificial Sequence
<220> FEATURE:
<223> OTHER INFORMATION: Synthetic Construct

<400> SEQUENCE: 44

Met Gln Ile Leu Val Lys Thr Pro Leu Ala Lys Asp Ile Arg Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Leu Gly Lys
        35                  40                  45

Gln Leu Glu Asp Gly Arg Thr Leu Ser Asp Tyr Asn Ile Gln Lys Ala
    50                  55                  60

Ser Asn Leu Tyr Leu Val Arg Arg Leu Pro Gly Met Lys Trp
65                  70                  75

<210> SEQ ID NO 45
<211> LENGTH: 78
<212> TYPE: PRT
<213> ORGANISM: Artificial Sequence
<220> FEATURE:
<223> OTHER INFORMATION: Synthetic Construct

<400> SEQUENCE: 45

Met Leu Ile Phe Val Asn Thr Phe Met Arg Tyr Pro Ile Thr Leu Glu
1               5                   10                  15

```
Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ser Gly Lys
        35                  40                  45

Gln Leu Glu Asp Gly Arg Thr Leu Ser Asp Tyr Asn Ile Lys Lys Glu
    50                  55                  60

Ser Thr Leu His Leu Val Leu Arg Leu Arg Gly Gly Gly
65                  70                  75

<210> SEQ ID NO 46
<211> LENGTH: 78
<212> TYPE: PRT
<213> ORGANISM: Artificial Sequence
<220> FEATURE:
<223> OTHER INFORMATION: Synthetic Construct

<400> SEQUENCE: 46

Met Gln Ile Leu Val Lys Thr Pro Met Arg Lys Ser Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile His Asn Lys
    50                  55                  60

Ser Thr Leu His Leu Val Ile Leu Arg Ala Trp Ser Thr
65                  70                  75

<210> SEQ ID NO 47
<211> LENGTH: 78
<212> TYPE: PRT
<213> ORGANISM: Artificial Sequence
<220> FEATURE:
<223> OTHER INFORMATION: Synthetic Construct

<400> SEQUENCE: 47

Met Gln Ile Arg Val Lys Thr Leu Thr Gly Asn Ser Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Trp Lys
        35                  40                  45

Glu Leu Glu Asp Gly Arg Thr Leu Ser Asp Tyr Asn Ile Lys Lys Trp
    50                  55                  60

Ser Phe Leu His Leu Val Leu Arg Leu Arg Gly Asn Gly Tyr
65                  70                  75

<210> SEQ ID NO 48
<211> LENGTH: 78
<212> TYPE: PRT
<213> ORGANISM: Artificial Sequence
<220> FEATURE:
<223> OTHER INFORMATION: Synthetic Construct

<400> SEQUENCE: 48

Met His Ile Phe Val Ser Thr Gly Ala Gly Val Ser Ile Ile Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Ser Leu Phe Phe Val Gly Asn
```

```
                35                  40                  45
Arg Leu Glu Asp Gly Arg Thr Leu Ser Asp Tyr Asn Ile Gln Lys Ala
    50                  55                  60

Ser Thr Leu His Leu Met Leu Arg Leu Leu Gly Met Gly Gln
65                  70                  75
```

<210> SEQ ID NO 49
<211> LENGTH: 78
<212> TYPE: PRT
<213> ORGANISM: Artificial Sequence
<220> FEATURE:
<223> OTHER INFORMATION: Synthetic Construct

<400> SEQUENCE: 49

```
Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Phe Ala Gly Lys
            35                  40                  45

Gln Leu Glu Asp Gly Arg Thr Leu Ser Asp Tyr Asn Ile Gln Lys Glu
    50                  55                  60

Ser Thr Leu His Leu Val Leu Arg Pro Ile Trp Ser Lys Tyr
65                  70                  75
```

<210> SEQ ID NO 50
<211> LENGTH: 78
<212> TYPE: PRT
<213> ORGANISM: Artificial Sequence
<220> FEATURE:
<223> OTHER INFORMATION: Synthetic Construct

<400> SEQUENCE: 50

```
Met Gln Ile Val Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Phe Ala Gly Lys
            35                  40                  45

Gln Leu Glu Asp Gly Arg Thr Leu Ser Asp Tyr Asn Ile Tyr Lys Asp
    50                  55                  60

Ser Thr Leu Tyr Leu Val Leu Arg Phe Pro Tyr Pro Lys Tyr
65                  70                  75
```

<210> SEQ ID NO 51
<211> LENGTH: 78
<212> TYPE: PRT
<213> ORGANISM: Artificial Sequence
<220> FEATURE:
<223> OTHER INFORMATION: Synthetic Construct

<400> SEQUENCE: 51

```
Met Asp Ile Ile Val Lys Thr Leu Asn Gly Lys Thr Ile Thr Leu Glu
1               5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Phe Ala Gly Lys
            35                  40                  45

Gln Leu Glu Asp Gly Arg Thr Leu Ser Asp Tyr Asn Ile His Lys Thr
    50                  55                  60
```

```
Ser Ile Leu His Leu Val Leu Arg Pro Pro Trp Ala Tyr Thr
65                  70                  75
```

<210> SEQ ID NO 52
<211> LENGTH: 78
<212> TYPE: PRT
<213> ORGANISM: Artificial Sequence
<220> FEATURE:
<223> OTHER INFORMATION: Synthetic Construct

<400> SEQUENCE: 52

```
Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Val
    50                  55                  60

Ser Ser Leu Tyr Leu Val Tyr Arg Pro Leu Trp Ser Thr Gln
65                  70                  75
```

<210> SEQ ID NO 53
<211> LENGTH: 78
<212> TYPE: PRT
<213> ORGANISM: Artificial Sequence
<220> FEATURE:
<223> OTHER INFORMATION: Synthetic Construct

<400> SEQUENCE: 53

```
Met Lys Ile Ser Val Glu Thr His Ser Asp Lys Thr Ile Ile Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Phe Phe Ser Gly Lys
        35                  40                  45

Gln Leu Glu Asp Gly Arg Thr Leu Ser Asp Tyr Asn Ile Gln Arg Val
    50                  55                  60

Ser Arg Leu His Leu Val Phe Arg Leu Arg Gly Gly Gly
65                  70                  75
```

<210> SEQ ID NO 54
<211> LENGTH: 78
<212> TYPE: PRT
<213> ORGANISM: Artificial Sequence
<220> FEATURE:
<223> OTHER INFORMATION: Synthetic Construct

<400> SEQUENCE: 54

```
Met Gln Ile Phe Val His Thr Leu Thr Gly Lys Ile Ile Arg Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Leu Phe Arg Ser Lys
        35                  40                  45

Gln Leu Glu Asp Gly Arg Thr Leu Ser Asp Tyr Asn Ile Leu Lys Glu
    50                  55                  60

Ser Trp Leu Arg Leu Ile Leu Arg Leu Arg Gly Gly Gly
65                  70                  75
```

<210> SEQ ID NO 55
<211> LENGTH: 78
<212> TYPE: PRT
<213> ORGANISM: Artificial Sequence
<220> FEATURE:
<223> OTHER INFORMATION: Synthetic Construct

<400> SEQUENCE: 55

```
Met Gln Ile Phe Val Lys Thr Ile Thr Trp His Pro Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln His Gly
    50                  55                  60

Ser Thr Leu Phe Leu Val Phe Thr Arg Arg Gly Arg Met Val
65                  70                  75
```

<210> SEQ ID NO 56
<211> LENGTH: 78
<212> TYPE: PRT
<213> ORGANISM: Artificial Sequence
<220> FEATURE:
<223> OTHER INFORMATION: Synthetic Construct

<400> SEQUENCE: 56

```
Met His Ile Phe Val Lys Thr Leu Lys Gly Met Gly Ile Ala Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Leu Gln Arg Leu Ile Phe Ala Gly Lys
        35                  40                  45

Gln Leu Glu Asp Gly Arg Thr Leu Ser Asp Tyr Asn Ile Gln Lys Gly
    50                  55                  60

Ser Ile Leu His Leu Arg Leu Ile Leu Arg Val Ser Arg Ser
65                  70                  75
```

<210> SEQ ID NO 57
<211> LENGTH: 78
<212> TYPE: PRT
<213> ORGANISM: Artificial Sequence
<220> FEATURE:
<223> OTHER INFORMATION: Synthetic Construct

<400> SEQUENCE: 57

```
Met Gln Ile Phe Val Val Thr Pro Gly Val Lys Ser Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Gln Lys
    50                  55                  60

Ser Thr Leu Phe Leu Leu Leu Arg Thr Leu Gly Ser Ile Ala
65                  70                  75
```

<210> SEQ ID NO 58
<211> LENGTH: 78
<212> TYPE: PRT

<213> ORGANISM: Artificial Sequence
<220> FEATURE:
<223> OTHER INFORMATION: Synthetic Construct

<400> SEQUENCE: 58

Met His Ile Phe Val Lys Thr Leu Pro Gly Lys Ile Ile Thr Leu Glu
1               5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Phe Ala Gly Lys
            35                  40                  45

Gln Leu Glu Asp Gly Arg Thr Leu Ser Asp Tyr Asn Ile Gln Lys Val
        50                  55                  60

Ser Asn Leu Asn Leu Trp Leu Arg Ile His Gly Asp Phe Lys
65                  70                  75

<210> SEQ ID NO 59
<211> LENGTH: 78
<212> TYPE: PRT
<213> ORGANISM: Artificial Sequence
<220> FEATURE:
<223> OTHER INFORMATION: Synthetic Construct

<400> SEQUENCE: 59

Met His Ile Phe Val Lys Thr Leu Ile Val Gln Ile Ile Pro Leu Glu
1               5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Phe Ala Gly Lys
            35                  40                  45

Ile Leu Glu Asp Gly Arg Thr Leu Ser Asp Tyr Asn Ile Leu Arg Asp
        50                  55                  60

Ser Thr Leu Tyr Leu Leu Phe Arg Leu Arg Gly Gly Gly
65                  70                  75

<210> SEQ ID NO 60
<211> LENGTH: 78
<212> TYPE: PRT
<213> ORGANISM: Artificial Sequence
<220> FEATURE:
<223> OTHER INFORMATION: Synthetic Construct

<400> SEQUENCE: 60

Met Asp Ile Phe Val Ser Thr Leu Thr Val Asn Thr Ile Pro Leu Glu
1               5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Phe Ala Gly Lys
            35                  40                  45

Gln Leu Glu Asp Gly Arg Thr Leu Ser Asp Tyr Asn Ile Gln Lys Trp
        50                  55                  60

Ser Arg Leu Leu Leu Val Leu Arg Leu Arg Gly Gly Gly
65                  70                  75

<210> SEQ ID NO 61
<211> LENGTH: 78
<212> TYPE: PRT
<213> ORGANISM: Artificial Sequence
<220> FEATURE:
<223> OTHER INFORMATION: Synthetic Construct

```
<400> SEQUENCE: 61

Met Leu Ile Cys Val Val Thr Val Thr Gly Leu Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Gly Leu Val Phe Ala Gly Met
        35                  40                  45

Lys Leu Glu Asp Gly Arg Thr Leu Ser Asp Tyr Asn Ile Gln Lys Glu
    50                  55                  60

Ser Ser Leu His Leu Val Val Ser Leu Pro Val Arg Ser Ser
65                  70                  75

<210> SEQ ID NO 62
<211> LENGTH: 78
<212> TYPE: PRT
<213> ORGANISM: Artificial Sequence
<220> FEATURE:
<223> OTHER INFORMATION: Synthetic Construct

<400> SEQUENCE: 62

Met Gln Ile Leu Val Arg Thr Leu Thr Gly Lys Thr Ile Arg Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Met
        35                  40                  45

Arg Leu Glu Asp Gly Arg Thr Leu Ser Asp Tyr Asn Ile Gln Gly Phe
    50                  55                  60

Ser Pro Leu Gly Leu Val Leu Arg Leu Leu Arg Val Glu Leu
65                  70                  75

<210> SEQ ID NO 63
<211> LENGTH: 78
<212> TYPE: PRT
<213> ORGANISM: Artificial Sequence
<220> FEATURE:
<223> OTHER INFORMATION: Synthetic Construct

<400> SEQUENCE: 63

Met Gln Ile Phe Val Lys Thr Val Ser Gly Lys Thr Ile Asn Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Gly Leu Ile Phe Ala Arg Lys
        35                  40                  45

Arg Leu Glu Asp Gly Arg Thr Leu Ser Asp Tyr Asn Ile Gln Asp Glu
    50                  55                  60

Ser Asn Leu His Leu Val Leu Thr Leu Val Gly Arg Asn Leu
65                  70                  75

<210> SEQ ID NO 64
<211> LENGTH: 78
<212> TYPE: PRT
<213> ORGANISM: Artificial Sequence
<220> FEATURE:
<223> OTHER INFORMATION: Synthetic Construct

<400> SEQUENCE: 64

Met Ala Ile Leu Val Lys Thr Val Thr Gly Asn Ser Ile Thr Leu Glu
1               5                   10                  15
```

```
Val Glu Pro Ser Asp Thr Ile Glu Asn Val Lys Ala Lys Ile Gln Asp
            20                  25                  30

Lys Glu Gly Ile Pro Pro Asp Gln Gln Gly Leu Leu Phe Ala Arg Thr
            35                  40                  45

Arg Leu Glu Asp Gly Arg Thr Leu Ser Asp Tyr Asn Ile Gln Lys Ala
        50                  55                  60

Ser Thr Leu His Leu Val Arg Thr Leu Arg Gly Thr Asp Thr
65                  70                  75
```

<210> SEQ ID NO 65
<211> LENGTH: 78
<212> TYPE: PRT
<213> ORGANISM: Artificial Sequence
<220> FEATURE:
<223> OTHER INFORMATION: Synthetic Construct

<400> SEQUENCE: 65

```
Met Ser Ile Phe Val Ile Thr Phe Thr Arg Lys Pro Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Ile Leu Ile Phe Ala Gly Lys
            35                  40                  45

Lys Leu Glu Asp Gly Arg Thr Leu Ser Asp Tyr Asn Ile Gln Lys Glu
        50                  55                  60

Ser Ser Leu Tyr Leu Phe Leu Arg Leu Arg Gly Ala Lys Val
65                  70                  75
```

<210> SEQ ID NO 66
<211> LENGTH: 78
<212> TYPE: PRT
<213> ORGANISM: Artificial Sequence
<220> FEATURE:
<223> OTHER INFORMATION: Synthetic Construct

<400> SEQUENCE: 66

```
Met Gln Ile Ser Val Val Thr Leu Thr Arg Pro Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Arg
            35                  40                  45

Asp Leu Glu Asp Gly Arg Thr Leu Ser Asp Tyr Asn Ile Gln Lys Gln
        50                  55                  60

Ser Ser Leu His Leu Phe Phe Arg Leu Arg Gly Ser Val Ser
65                  70                  75
```

<210> SEQ ID NO 67
<211> LENGTH: 78
<212> TYPE: PRT
<213> ORGANISM: Artificial Sequence
<220> FEATURE:
<223> OTHER INFORMATION: Synthetic Construct

<400> SEQUENCE: 67

```
Met Leu Ile Phe Val Asn Thr Arg Pro Trp Lys Thr Ile Ser Leu Glu
1               5                   10                  15

Val Glu Pro Ser Asp Thr Ile Glu Asn Val Lys Ala Lys Ile Gln Asp
            20                  25                  30
```

```
Lys Glu Gly Ile Pro Pro Asp Gln Gln Ile Leu Phe Phe Gly Gly Lys
            35                  40                  45

Gln Leu Glu Asp Gly Arg Thr Leu Ser Asp Tyr Asn Ile Pro Asn Lys
 50                  55                  60

Ser Ile Leu His Leu Arg Leu Arg Pro Arg Ile Lys Arg Gln
 65                  70                  75
```

<210> SEQ ID NO 68
<211> LENGTH: 78
<212> TYPE: PRT
<213> ORGANISM: Artificial Sequence
<220> FEATURE:
<223> OTHER INFORMATION: Synthetic Construct

<400> SEQUENCE: 68

```
Met Gln Ile Phe Val Gln Thr Leu Met Gly Asp Asn Ile Ser Leu Glu
 1               5                  10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Asp Asn
            35                  40                  45

Gln Leu Glu Asp Gly Arg Thr Leu Ser Asp Tyr Asn Ile Lys Lys Lys
 50                  55                  60

Ser His Leu Leu Leu Leu Leu Arg Pro Arg Gly Tyr Arg Ser
 65                  70                  75
```

<210> SEQ ID NO 69
<211> LENGTH: 78
<212> TYPE: PRT
<213> ORGANISM: Artificial Sequence
<220> FEATURE:
<223> OTHER INFORMATION: Synthetic Construct

<400> SEQUENCE: 69

```
Met Gln Ile Phe Val Lys Thr Leu Ile Gly Tyr Thr Ile Pro Leu Glu
 1               5                  10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
            35                  40                  45

Gln Leu Glu Asp Gly Arg Thr Leu Ser Asp Tyr Asn Ile Cys Gln Glu
 50                  55                  60

Ser Asn Leu His Leu Ala Phe Pro Leu Pro Gly Asp Glu Glu
 65                  70                  75
```

<210> SEQ ID NO 70
<211> LENGTH: 78
<212> TYPE: PRT
<213> ORGANISM: Artificial Sequence
<220> FEATURE:
<223> OTHER INFORMATION: Synthetic Construct

<400> SEQUENCE: 70

```
Met Gln Ile Phe Val Lys Thr Phe Ser Gly Lys Tyr Ile Thr Leu Glu
 1               5                  10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Thr Phe Val Ala Lys
            35                  40                  45

Gln Leu Glu Asp Gly Arg Thr Leu Ser Asp Tyr Asn Ile Gln Lys Gly
```

```
                50                  55                  60
Ser Ala Leu Arg Leu Ile Leu Gln Arg Arg Gly Asn His Asp
65                  70                  75

<210> SEQ ID NO 71
<211> LENGTH: 21
<212> TYPE: DNA
<213> ORGANISM: Artificial Sequence
<220> FEATURE:
<223> OTHER INFORMATION: Synthetic Construct

<400> SEQUENCE: 71
ctaatgatgc tggaccacac c                                               21

<210> SEQ ID NO 72
<211> LENGTH: 21
<212> TYPE: DNA
<213> ORGANISM: Artificial Sequence
<220> FEATURE:
<223> OTHER INFORMATION: Synthetic Construct

<400> SEQUENCE: 72
aaagcgtctg ctccgtgatg c                                               21

<210> SEQ ID NO 73
<211> LENGTH: 20
<212> TYPE: DNA
<213> ORGANISM: Artificial Sequence
<220> FEATURE:
<223> OTHER INFORMATION: Synthetic Construct

<400> SEQUENCE: 73
gccagtgaag aagtacctgc                                                 20

<210> SEQ ID NO 74
<211> LENGTH: 19
<212> TYPE: DNA
<213> ORGANISM: Artificial Sequence
<220> FEATURE:
<223> OTHER INFORMATION: Synthetic Construct

<400> SEQUENCE: 74
cctgggtggc actggtgaa                                                  19

<210> SEQ ID NO 75
<211> LENGTH: 21
<212> TYPE: DNA
<213> ORGANISM: Artificial Sequence
<220> FEATURE:
<223> OTHER INFORMATION: Synthetic Construct

<400> SEQUENCE: 75
aagaatctgc cggttcgagg c                                               21

<210> SEQ ID NO 76
<211> LENGTH: 21
<212> TYPE: DNA
<213> ORGANISM: Artificial Sequence
<220> FEATURE:
<223> OTHER INFORMATION: Synthetic Construct

<400> SEQUENCE: 76
taccactcct ggatggcatt g                                               21

<210> SEQ ID NO 77
```

```
<211> LENGTH: 20
<212> TYPE: DNA
<213> ORGANISM: Artificial Sequence
<220> FEATURE:
<223> OTHER INFORMATION: Synthetic Construct

<400> SEQUENCE: 77
cgtcttcacc accatggaga                                                    20

<210> SEQ ID NO 78
<211> LENGTH: 20
<212> TYPE: DNA
<213> ORGANISM: Artificial Sequence
<220> FEATURE:
<223> OTHER INFORMATION: Synthetic Construct

<400> SEQUENCE: 78
cggccatcac gccacagttt                                                    20

<210> SEQ ID NO 79
<211> LENGTH: 78
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is Ala, Asp, Glu, His, Lys, Leu, Pro, Gln,
      Arg, Ser, Thr, or Tyr.
<220> FEATURE:
<221> NAME/KEY: MISC_FEATURE
<222> LOCATION: (4)..(4)
<223> OTHER INFORMATION: Xaa is Ala, Cys, Phe, Ile, Leu, Arg, Ser, Val,
      or Tyr.
<220> FEATURE:
<221> NAME/KEY: MISC_FEATURE
<222> LOCATION: (6)..(6)
<223> OTHER INFORMATION: Xaa is Glu, Gly, His, Ile, Lys, Asn, Gln, Arg,
      Ser, Val, Trp, or Tyr.
<220> FEATURE:
<221> NAME/KEY: MISC_FEATURE
<222> LOCATION: (8)..(8)
<223> OTHER INFORMATION: Xaa is Phe, Gly, His, Ile, Leu, Met, Pro, Arg,
      Val, or Tyr.
<220> FEATURE:
<221> NAME/KEY: MISC_FEATURE
<222> LOCATION: (9)..(9)
<223> OTHER INFORMATION: Xaa is Ala, Phe, Gly, Ile, Lys, Leu, Met, Asn,
      Pro, Arg, Ser, or Thr.
<220> FEATURE:
<221> NAME/KEY: MISC_FEATURE
<222> LOCATION: (10)..(10)
<223> OTHER INFORMATION: Xaa is Ala, Asp, Gly, Leu, Arg, Val, or Trp.
<220> FEATURE:
<221> NAME/KEY: MISC_FEATURE
<222> LOCATION: (11)..(11)
<223> OTHER INFORMATION: Xaa is Asp, Glu, His, Ile, Lys, Leu, Met, Asn,
      Pro, Gln, Arg, Thr, Val, Trp, or Tyr.
<220> FEATURE:
<221> NAME/KEY: MISC_FEATURE
<222> LOCATION: (12)..(12)
<223> OTHER INFORMATION: Xaa is Asp, Gly, Ile, Leu, Asn, Pro, Ser, Thr,
      Val, or Tyr.
<220> FEATURE:
<221> NAME/KEY: MISC_FEATURE
<222> LOCATION: (14)..(14)
<223> OTHER INFORMATION: Xaa is Ala, Cys, Phe, Ile, Lys, Asn, Pro, Arg,
      Ser, or Thr.
<220> FEATURE:
<221> NAME/KEY: MISC_FEATURE
<222> LOCATION: (42)..(42)
<223> OTHER INFORMATION: Xaa is Phe, Gly, Ile, Lys, Leu, Gln, Arg, Ser,
      Thr, or Val.
<220> FEATURE:
<221> NAME/KEY: MISC_FEATURE
<222> LOCATION: (44)..(44)
```

```
<223> OTHER INFORMATION: Xaa is Phe, Ile, Leu, Thr, or Val.
<220> FEATURE:
<221> NAME/KEY: MISC_FEATURE
<222> LOCATION: (46)..(46)
<223> OTHER INFORMATION: Xaa is Ala, Gly, His, Leu, Arg, Ser, Thr, or
      Val.
<220> FEATURE:
<221> NAME/KEY: MISC_FEATURE
<222> LOCATION: (47)..(47)
<223> OTHER INFORMATION: Xaa is Ala, Asp, Gly, Arg, Ser, or Trp.
<220> FEATURE:
<221> NAME/KEY: MISC_FEATURE
<222> LOCATION: (48)..(48)
<223> OTHER INFORMATION: Xaa is Lys, Met, Asn, Gln, Arg, or Thr.
<220> FEATURE:
<221> NAME/KEY: MISC_FEATURE
<222> LOCATION: (49)..(49)
<223> OTHER INFORMATION: Xaa is Asp, Glu, His, Ile, Lys, Asn, Pro, Gln,
      Arg, or Ser.
<220> FEATURE:
<221> NAME/KEY: MISC_FEATURE
<222> LOCATION: (62)..(62)
<223> OTHER INFORMATION: Xaa is Cys, His, Lys, Leu, Pro, Gln, Arg, or
      Tyr.
<220> FEATURE:
<221> NAME/KEY: MISC_FEATURE
<222> LOCATION: (63)..(63)
<223> OTHER INFORMATION: Xaa is Asp, Glu, Gly, His, Lys, Met, Asn, Gln,
      Arg, or Tyr.
<220> FEATURE:
<221> NAME/KEY: MISC_FEATURE
<222> LOCATION: (64)..(64)
<223> OTHER INFORMATION: Xaa is Ala, Asp, Glu, Phe, Gly,  Lys, Gln, Arg,
      Thr, Val, Trp, or Tyr.
<220> FEATURE:
<221> NAME/KEY: MISC_FEATURE
<222> LOCATION: (66)..(66)
<223> OTHER INFORMATION: Xaa is Ala, Phe, His, Ile, Leu, Asn, Pro, Gln,
      Arg, Ser, Thr, or Trp.
<220> FEATURE:
<221> NAME/KEY: MISC_FEATURE
<222> LOCATION: (68)..(68)
<223> OTHER INFORMATION: Xaa is Gly, Phe, His, Leu, Asn, Arg, Ser, Thr,
      Trp, or Tyr.
<220> FEATURE:
<221> NAME/KEY: MISC_FEATURE
<222> LOCATION: (70)..(70)
<223> OTHER INFORMATION: Xaa is Ala, Ile, Phe, Lys, Leu, Met, Arg, Val,
      or Trp.
<220> FEATURE:
<221> NAME/KEY: MISC_FEATURE
<222> LOCATION: (71)..(71)
<223> OTHER INFORMATION: Xaa is Phe, Gly, Lys, Leu, Met, Arg, Val, or
      Tyr.
<220> FEATURE:
<221> NAME/KEY: MISC_FEATURE
<222> LOCATION: (72)..(72)
<223> OTHER INFORMATION: Xaa is Gly, Ile, Lys, Pro, Gln, Arg, Ser, or
      Thr.
<220> FEATURE:
<221> NAME/KEY: MISC_FEATURE
<222> LOCATION: (73)..(73)
<223> OTHER INFORMATION: Xaa is Phe, Ile, Leu, Pro, Arg, or Thr.
<220> FEATURE:
<221> NAME/KEY: MISC_FEATURE
<222> LOCATION: (74)..(74)
<223> OTHER INFORMATION: Xaa is Leu, His, Ile, Pro, Arg, or Val.
<220> FEATURE:
<221> NAME/KEY: MISC_FEATURE
<222> LOCATION: (75)..(75)
<223> OTHER INFORMATION: Xaa is Ala, Asp, Gly, Ile, Pro, Arg, Val, Trp,
      or Tyr
<220> FEATURE:
<221> NAME/KEY: MISC_FEATURE
<222> LOCATION: (76)..(76)
<223> OTHER INFORMATION: Xaa is Ala, Asp, Phe, Gly, His, Lys, Leu, Met,
      Asn, Pro, Gln, Arg, Ser, Thr, Val, Trp, or Tyr.
<220> FEATURE:
<221> NAME/KEY: MISC_FEATURE
```

```
<222> LOCATION: (77)..(77)
<223> OTHER INFORMATION: Xaa is Ala, Asp, Glu, Phe, His, Ile, Lys, Met,
      Asn, Pro, Gln, Arg, Ser, Thr, Val, or Tyr.
<220> FEATURE:
<221> NAME/KEY: MISC_FEATURE
<222> LOCATION: (78)..(78)
<223> OTHER INFORMATION: Xaa is Ala, Asp, Glu, Phe, His, Ile, Lys, Leu,
      Asn, Pro, Gln, Arg, Ser, Thr, Val, Trp, or Tyr.

<400> SEQUENCE: 79

Met Xaa Ile Xaa Val Xaa Thr Xaa Xaa Xaa Xaa Ile Xaa Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Xaa Leu Xaa Phe Xaa Xaa Xaa
                35                  40                  45

Xaa Leu Glu Asp Gly Arg Thr Leu Ser Asp Tyr Asn Ile Xaa Xaa Xaa
50                  55                  60

Ser Xaa Leu Xaa Leu Xaa Xaa Xaa Xaa Xaa Xaa Xaa Xaa
65                  70                  75

<210> SEQ ID NO 80
<211> LENGTH: 158
<212> TYPE: PRT
<213> ORGANISM: Artificial Sequence
<220> FEATURE:
<223> OTHER INFORMATION: Synthetic Construct

<400> SEQUENCE: 80

Glu Met Phe Asn Pro Tyr Tyr Gly Leu Phe Glu Tyr Ser Ala Thr Asp
1               5                   10                  15

Asn Tyr Thr Leu Gln Ile Asn Pro Asn Ser Gly Leu Cys Asn Glu Asp
            20                  25                  30

His Leu Ser Tyr Phe Lys Phe Ile Gly Arg Val Ala Gly Met Ala Val
                35                  40                  45

Tyr His Gly Lys Leu Leu Asp Gly Phe Phe Ile Arg Pro Phe Tyr Lys
50                  55                  60

Met Met Leu His Lys Pro Ile Thr Leu His Asp Met Glu Ser Val Asp
65                  70                  75                  80

Ser Glu Tyr Tyr Asn Ser Leu Arg Trp Ile Leu Glu Asn Asp Pro Thr
                85                  90                  95

Glu Leu Asp Leu Arg Phe Ile Ile Asp Glu Glu Leu Phe Gly Gln Thr
            100                 105                 110

His Gln His Glu Leu Lys Asp Gly Gly Ser Glu Ile Val Val Thr Asn
            115                 120                 125

Lys Asn Lys Lys Glu Tyr Ile Tyr Leu Val Ile Gln Trp Arg Phe Val
    130                 135                 140

Asn Arg Ile Gln Lys Gln Met Ala Ala Phe Lys Glu Gly Phe
145                 150                 155

<210> SEQ ID NO 81
<211> LENGTH: 158
<212> TYPE: PRT
<213> ORGANISM: Artificial Sequence
<220> FEATURE:
<223> OTHER INFORMATION: Synthetic Construct

<400> SEQUENCE: 81

Glu Met Phe Asn Pro Tyr Tyr Gly Leu Phe Glu Tyr Ser Ala Thr Asp
1               5                   10                  15
```

```
Asn Tyr Thr Leu Gln Ile Asn Pro Asn Ser Gly Leu Cys Asn Glu Asp
                20                  25                  30

His Leu Ser Tyr Phe Thr Phe Ile Gly Arg Val Ala Gly Leu Ala Val
            35                  40                  45

Phe His Gly Lys Leu Leu Asp Gly Phe Phe Ile Arg Pro Phe Tyr Lys
        50                  55                  60

Met Met Leu Gly Lys Gln Ile Thr Leu Asn Asp Met Glu Ser Val Asp
65                  70                  75                  80

Ser Glu Tyr Tyr Asn Ser Leu Lys Trp Ile Leu Glu Asn Asp Pro Thr
                85                  90                  95

Glu Leu Asp Leu Met Phe Cys Ile Asp Glu Glu Asn Phe Gly Gln Thr
            100                 105                 110

Tyr Gln Val Asp Leu Lys Pro Asn Gly Ser Glu Ile Met Val Thr Asn
        115                 120                 125

Glu Asn Lys Arg Glu Tyr Ile Asp Leu Val Ile Gln Trp Arg Phe Val
130                 135                 140

Asn Arg Val Gln Lys Gln Met Asn Ala Phe Leu Glu Gly Phe
145                 150                 155

<210> SEQ ID NO 82
<211> LENGTH: 158
<212> TYPE: PRT
<213> ORGANISM: Artificial Sequence
<220> FEATURE:
<223> OTHER INFORMATION: Synthetic Construct

<400> SEQUENCE: 82

Glu Met Leu Asn Pro Tyr Tyr Gly Leu Phe Gln Tyr Ser Thr Asp Asn
1               5                   10                  15

Ile Tyr Met Leu Gln Ile Asn Pro Asp Ser Ser Ile Asn Pro Asp His
                20                  25                  30

Leu Ser Tyr Phe His Phe Val Gly Arg Ile Met Gly Leu Ala Val Phe
            35                  40                  45

His Gly His Tyr Ile Asn Gly Gly Phe Thr Val Pro Phe Tyr Lys Gln
        50                  55                  60

Leu Leu Gly Lys Pro Ile Gln Leu Ser Asp Leu Glu Ser Val Asp Pro
65                  70                  75                  80

Glu Leu His Lys Ser Leu Val Trp Ile Leu Glu Asn Asp Ile Thr Pro
                85                  90                  95

Val Leu Asp His Thr Phe Cys Val Glu His Asn Ala Phe Gly Arg Ile
            100                 105                 110

Leu Gln His Glu Leu Lys Pro Asn Gly Arg Asn Val Pro Val Thr Glu
        115                 120                 125

Glu Asn Lys Lys Glu Tyr Val Arg Leu Tyr Val Asn Trp Arg Phe Met
130                 135                 140

Arg Gly Ile Glu Ala Gln Phe Leu Ala Leu Gln Lys Gly Phe
145                 150                 155

<210> SEQ ID NO 83
<211> LENGTH: 158
<212> TYPE: PRT
<213> ORGANISM: Artificial Sequence
<220> FEATURE:
<223> OTHER INFORMATION: Synthetic Construct

<400> SEQUENCE: 83

Glu Met Leu Asn Pro Tyr Tyr Gly Leu Phe Gln Tyr Ser Arg Asp Asp
1               5                   10                  15
```

Ile Tyr Thr Leu Gln Ile Asn Pro Asp Ser Ala Val Asn Pro Glu His
            20                  25                  30

Leu Ser Tyr Phe His Phe Val Gly Arg Ile Met Gly Met Ala Val Phe
            35                  40                  45

His Gly His Tyr Ile Asp Gly Gly Phe Thr Leu Pro Phe Tyr Lys Gln
            50                  55                  60

Leu Leu Gly Lys Ser Ile Thr Leu Asp Met Glu Leu Val Asp Pro
65                  70                  75                  80

Asp Leu His Asn Ser Leu Val Trp Ile Leu Glu Asn Asp Ile Thr Gly
                85                  90                  95

Val Leu Asp His Thr Phe Cys Val Glu His Asn Ala Tyr Gly Glu Ile
            100                 105                 110

Ile Gln His Glu Leu Lys Pro Asn Gly Lys Ser Ile Pro Val Asn Glu
            115                 120                 125

Glu Asn Lys Lys Glu Tyr Val Arg Leu Tyr Val Asn Trp Arg Phe Leu
130                 135                 140

Arg Gly Ile Glu Ala Gln Phe Leu Ala Leu Gln Lys Gly Phe
145                 150                 155

<210> SEQ ID NO 84
<211> LENGTH: 159
<212> TYPE: PRT
<213> ORGANISM: Artificial Sequence
<220> FEATURE:
<223> OTHER INFORMATION: Synthetic Construct

<400> SEQUENCE: 84

Glu Val Leu Asn Pro Met Tyr Cys Leu Phe Glu Tyr Ala Gly Lys Asn
1               5                   10                  15

Asn Tyr Cys Leu Gln Ile Asn Pro Ala Ser Thr Ile Asn Pro Asp His
            20                  25                  30

Leu Ser Tyr Phe Cys Phe Ile Gly Arg Phe Ile Ala Met Ala Leu Phe
            35                  40                  45

His Gly Lys Phe Ile Asp Thr Gly Phe Ser Leu Pro Phe Tyr Lys Arg
            50                  55                  60

Met Leu Ser Lys Lys Leu Thr Ile Lys Asp Leu Glu Ser Ile Asp Thr
65                  70                  75                  80

Glu Phe Tyr Asn Ser Leu Ile Trp Ile Arg Asp Asn Asn Ile Glu Glu
                85                  90                  95

Cys Gly Leu Glu Met Tyr Phe Ser Val Asp Met Glu Ile Leu Gly Lys
            100                 105                 110

Val Thr Ser Met Asp Leu Lys Leu Gly Gly Ser Asn Ile Leu Val Thr
            115                 120                 125

Glu Glu Asn Lys Asp Glu Tyr Ile Gly Leu Met Thr Glu Trp Arg Phe
            130                 135                 140

Ser Arg Gly Val Gln Glu Gln Thr Lys Ala Phe Leu Asp Gly Phe
145                 150                 155

<210> SEQ ID NO 85
<211> LENGTH: 159
<212> TYPE: PRT
<213> ORGANISM: Artificial Sequence
<220> FEATURE:
<223> OTHER INFORMATION: Synthetic Construct

<400> SEQUENCE: 85

Glu Val Leu Asn Pro Met Tyr Cys Leu Phe Glu Tyr Ala Gly Lys Asn

```
                1               5                   10                  15
Asn Tyr Cys Leu Gln Ile Asn Pro Ala Ser Ser Ile Asn Pro Asp His
            20                  25                  30

Leu Thr Tyr Phe Arg Phe Ile Gly Arg Phe Ile Ala Met Ala Leu Tyr
            35                  40                  45

His Gly Lys Phe Ile Asp Thr Gly Phe Thr Leu Pro Phe Tyr Lys Arg
 50                  55                  60

Met Leu Asn Lys Arg Pro Thr Leu Lys Asp Leu Glu Ser Ile Asp Pro
 65                  70                  75                  80

Glu Phe Tyr Asn Ser Ile Val Trp Ile Lys Glu Asn Asn Leu Glu Glu
                85                  90                  95

Cys Gly Leu Glu Leu Tyr Phe Ile Gln Asp Met Glu Ile Leu Gly Lys
            100                 105                 110

Val Thr Thr His Glu Leu Lys Glu Gly Gly Ser Ile Arg Val Thr
            115                 120                 125

Glu Glu Asn Lys Glu Glu Tyr Ile Met Leu Leu Thr Asp Trp Arg Phe
            130                 135                 140

Thr Arg Gly Val Glu Glu Gln Thr Lys Ala Phe Leu Asp Gly Phe
145                 150                 155

<210> SEQ ID NO 86
<211> LENGTH: 156
<212> TYPE: PRT
<213> ORGANISM: Artificial Sequence
<220> FEATURE:
<223> OTHER INFORMATION: Synthetic Construct

<400> SEQUENCE: 86

Glu Val Leu Asn Pro Met Tyr Cys Leu Phe Glu Tyr Ala Gly Lys Cys
1               5                   10                  15

Leu Gln Ile Asn Pro Ala Ser Tyr Ile Asn Pro Asp His Leu Lys Tyr
            20                  25                  30

Phe Arg Phe Ile Gly Arg Phe Ile Ala Met Ala Leu His Gly Lys
            35                  40                  45

Phe Ile Asp Thr Gly Phe Ser Leu Pro Phe Tyr Lys Arg Ile Leu Asn
 50                  55                  60

Lys Pro Val Gly Leu Lys Asp Leu Glu Ser Ile Asp Pro Glu Phe Tyr
 65                  70                  75                  80

Asn Ser Leu Ile Trp Val Lys Glu Asn Asn Ile Glu Glu Cys Asp Leu
                85                  90                  95

Glu Met Tyr Phe Ser Val Asp Lys Glu Ile Leu Gly Ile Lys Ser
            100                 105                 110

His Asp Leu Lys Pro Asn Gly Gly Asn Ile Leu Val Thr Glu Glu Asn
            115                 120                 125

Lys Glu Glu Tyr Ile Arg Met Val Ala Glu Trp Arg Leu Ser Arg Gly
            130                 135                 140

Val Glu Glu Gln Thr Gln Ala Phe Phe Glu Gly Phe
145                 150                 155

<210> SEQ ID NO 87
<211> LENGTH: 158
<212> TYPE: PRT
<213> ORGANISM: Artificial Sequence
<220> FEATURE:
<223> OTHER INFORMATION: Synthetic Construct

<400> SEQUENCE: 87
```

```
Glu Met Phe Asn Pro Phe Tyr Cys Leu Phe Glu Tyr Ser Ala Tyr Asp
1               5                   10                  15

Asn Tyr Thr Ile Gln Ile Asn Pro Asn Ser Gly Ile Asn Pro Glu His
            20                  25                  30

Leu Asn Tyr Phe Lys Phe Ile Gly Arg Val Val Gly Leu Gly Val Phe
            35                  40                  45

His Arg Arg Phe Leu Asp Ala Phe Phe Val Gly Ala Leu Tyr Lys Met
            50                  55                  60

Met Leu Arg Lys Lys Val Val Leu Gln Asp Met Glu Gly Val Asp Ala
65                  70                  75                  80

Glu Val Tyr Asn Ser Leu Asn Trp Met Leu Glu Asn Ser Ile Asp Gly
                85                  90                  95

Val Leu Asp Leu Thr Phe Ser Ala Asp Asp Glu Arg Phe Gly Glu Val
            100                 105                 110

Val Thr Val Asp Leu Lys Pro Asp Gly Arg Asn Ile Glu Val Thr Asp
            115                 120                 125

Gly Asn Lys Lys Glu Tyr Val Glu Leu Tyr Thr Gln Trp Arg Ile Val
    130                 135                 140

Asp Arg Val Gln Glu Gln Phe Lys Ala Phe Met Asp Gly Phe
145                 150                 155
```